US011938196B2

(12) United States Patent
Heppenstall

(10) Patent No.: US 11,938,196 B2
(45) Date of Patent: Mar. 26, 2024

(54) MODIFIED VIRAL PARTICLES FOR GENE THERAPY

(71) Applicants: EUROPEAN MOLECULAR BIOLOGY LABORATORY, Heidelberg (DE); BOREA THERAPEUTICS S.R.L., Milan (IT)

(72) Inventor: Paul Alexander Heppenstall, Heidelberg (DE)

(73) Assignee: BOREA THERAPEUTICS S.R.L., Milan (IT)

( * ) Notice: Subject to any disclaimer, the term of this patent is extended or adjusted under 35 U.S.C. 154(b) by 0 days.

(21) Appl. No.: 18/316,191

(22) Filed: May 11, 2023

(65) Prior Publication Data

US 2023/0338578 A1    Oct. 26, 2023

Related U.S. Application Data

(63) Continuation of application No. PCT/EP2021/081424, filed on Nov. 11, 2021.

(60) Provisional application No. 63/112,457, filed on Nov. 11, 2020.

(51) Int. Cl.
| | |
|---|---|
| *A61K 35/76* | (2015.01) |
| *A61K 31/4192* | (2006.01) |
| *A61K 38/00* | (2006.01) |
| *A61K 39/00* | (2006.01) |
| *A61K 47/54* | (2017.01) |
| *A61K 48/00* | (2006.01) |
| *A61P 25/00* | (2006.01) |
| *C12N 15/86* | (2006.01) |
| *A61K 47/60* | (2017.01) |
| *A61K 47/62* | (2017.01) |
| *C07K 14/005* | (2006.01) |

(52) U.S. Cl.
CPC ...... *A61K 48/0033* (2013.01); *A61K 31/4192* (2013.01); *A61K 35/76* (2013.01); *C12N 15/86* (2013.01); *A61K 47/545* (2017.08); *A61K 47/60* (2017.08); *A61K 47/62* (2017.08); *C07K 14/005* (2013.01); *C12N 2750/14143* (2013.01); *C12N 2750/14145* (2013.01)

(58) Field of Classification Search
CPC ............. A61K 2039/505; A61K 35/76; A61K 38/00; A61P 25/00; C07K 14/005
See application file for complete search history.

(56) References Cited

U.S. PATENT DOCUMENTS

2022/0288234 A1    9/2022   Heppenstall

FOREIGN PATENT DOCUMENTS

| | | |
|---|---|---|
| EP | 3070095 A1 | 9/2016 |
| EP | 3461836 A1 | 4/2019 |
| WO | WO 2010/127097 A1 | 11/2010 |
| WO | WO 2014/193716 A2 | 12/2014 |
| WO | WO 2015/112016 A1 | 7/2015 |
| WO | WO 2017/189963 A1 | 11/2017 |
| WO | WO 2017/197355 A2 | 11/2017 |
| WO | WO 2019/006043 A1 | 1/2019 |
| WO | WO 2020/225363 A2 | 11/2020 |

OTHER PUBLICATIONS

Debets et al., "Azide: A Unique Dipole for Metal-Free Bioorthogonal Ligations," ChemBioChem, vol. 11, Issue 9, 2010, pp. 1168-1184.
Extended European Search Report, European Patent Application No. 19173365.8, dated Jan. 21, 2020, 14 pages.
International Preliminary Report on Patentability Chapter 1, Patent Cooperation Treaty Application No. PCT/EP2020/062713, dated Nov. 18, 2021, 18 pages.
International Preliminary Report on Patentability Chapter 1, Patent Cooperation Treaty Application No. PCT/EP2021/081424, dated May 25, 2023, 8 pages.
International Search Report and Written Opinion, Patent Cooperation Treaty Application No. PCT/EP2020/062713, dated Nov. 20, 2020, 25 pages.
International Search Report and Written Opinion, Patent Cooperation Treaty Application No. PCT/EP2021/081424, dated Mar. 4, 2022, 15 pages.
Katrekar et al., "Oligonucleotide conjugated multi-functional adeno-associated viruses" with Supplemmentary Information, *Scientific Reports*, vol. 8, Article No. 3589, Feb. 2018, 17 pages.
Kelemen et al., "A Precise Chemical Strategy to Alter the Receptor Specificity of the Adeno-Associated Virus," Angewandte Chemie, vol. 55, Issue 36, Aug. 2016, pp. 10645-10649.
Lallana et al., "Click Chemistry for Drug Delivery Nanosystems," Pharmaceutical Research, vol. 29, 2012, pp. 1-34.
Li, et al., "Development and Applications of the Copper-Catalyzed Azide-Alkyne Cycloaddition (CuAAC) as a Bioorthogonal Reaction," Molecules, 2016, vol. 21, No. 10, 1393, 22 pages.
Liu et al., "Site-Specific Modification of Adeno-Associated Viruses via a Genetically Engineered Aldehyde Tag," Small, vol. 9, Issue 3, 2013, pp. 421-429.
McKay et al., "Click Chemistry in Complex Mixtures: Bioorthogonal Bioconjugation," Chemistry & Biology, vol. 21, Issue 9, 2014, pp. 1075-1101.
Partial European Search Report, European Patent Application No. 19173365.8, dated Sep. 19, 2019, 17 pages.
Shi, "Insertional Mutagenesis at Positions 520 and 584 of Adeno-Associated Virus Type 2 (AAV2) Capsid Gene and Generation of AAV2 Vectors with Eliminated Heparin-Binding Ability and Introduced Novel Tropism," Human Gene Therapy, vol. 17, Issue 3, Mar. 2006, p. 353-361.

(Continued)

*Primary Examiner* — Barry A Chestnut
(74) *Attorney, Agent, or Firm* — Fenwick & West LLP

(57) ABSTRACT

This invention relates to novel surface modified viral capsids and recombinant virions comprising the same. Furthermore, this invention concerns intermediates for the preparation of surface modified viral capsids. The surface modified viral capsids are designed to selectively and/or more efficiently deliver gene therapy. The surface modified viral capsids, when incorporated into a recombinant virion, can be used to treat an illness that is characterized by genetic abnormality.

24 Claims, 77 Drawing Sheets

Specification includes a Sequence Listing.

(56) References Cited

OTHER PUBLICATIONS

Spicer et al., "Selective chemical protein modification," Nature Communications, vol. 5, Article No. 4740, 2014, pp. 1-14.
Stachler et al., "Site-specific Modification of AAV Vector Particles with Biophysical Probes and Targeting Ligands Using Biotin Ligase," *Molecular Therapy*, vol. 16, Issue 8, Aug. 2008, pp. 1467-1473.
Wang et al., "Bioconjugation by Copper(I)-Catalyzed Azide-Alkyne [3+2] Cycloaddition," Journal of the American Chemical Society, vol. 125, No. 11, 2003, pp. 3192-3193.
Wu et al., "Mutational Analysis of the Adeno-Associated Virus Type 2 (AAV2) Capsid Gene and Construction of AAV2 Vectors with Altered Tropism," *Journal of Virology*, vol. 74, No. 18, Sep. 2000, pp. 8635-8647.
Yao et al., "Site-Specific PEGylated Adeno-Associated Viruses with Increased Serum Stability and Reduced Immunogenicity," Molecules, 2017, vol. 22, No. 7, 1155, 15 pages.
Zhang et al., "Development of next generation adeno-associated viral vectors capable of selective tropism and efficient gene delivery," *Biomaterials*, vol. 80, Feb. 2016, pp. 134-145.
Koniev, O., et al., "Developments and recent advancements in the field of endogenous amino acid selective bond forming reactions for bioconjugation," Chemical Society Reviews, May 22, 2015, vol. 2015, No. 44, pp. 5495-5551, https://doi.org/10.1039/c5cs00048c, PMID:26000775.

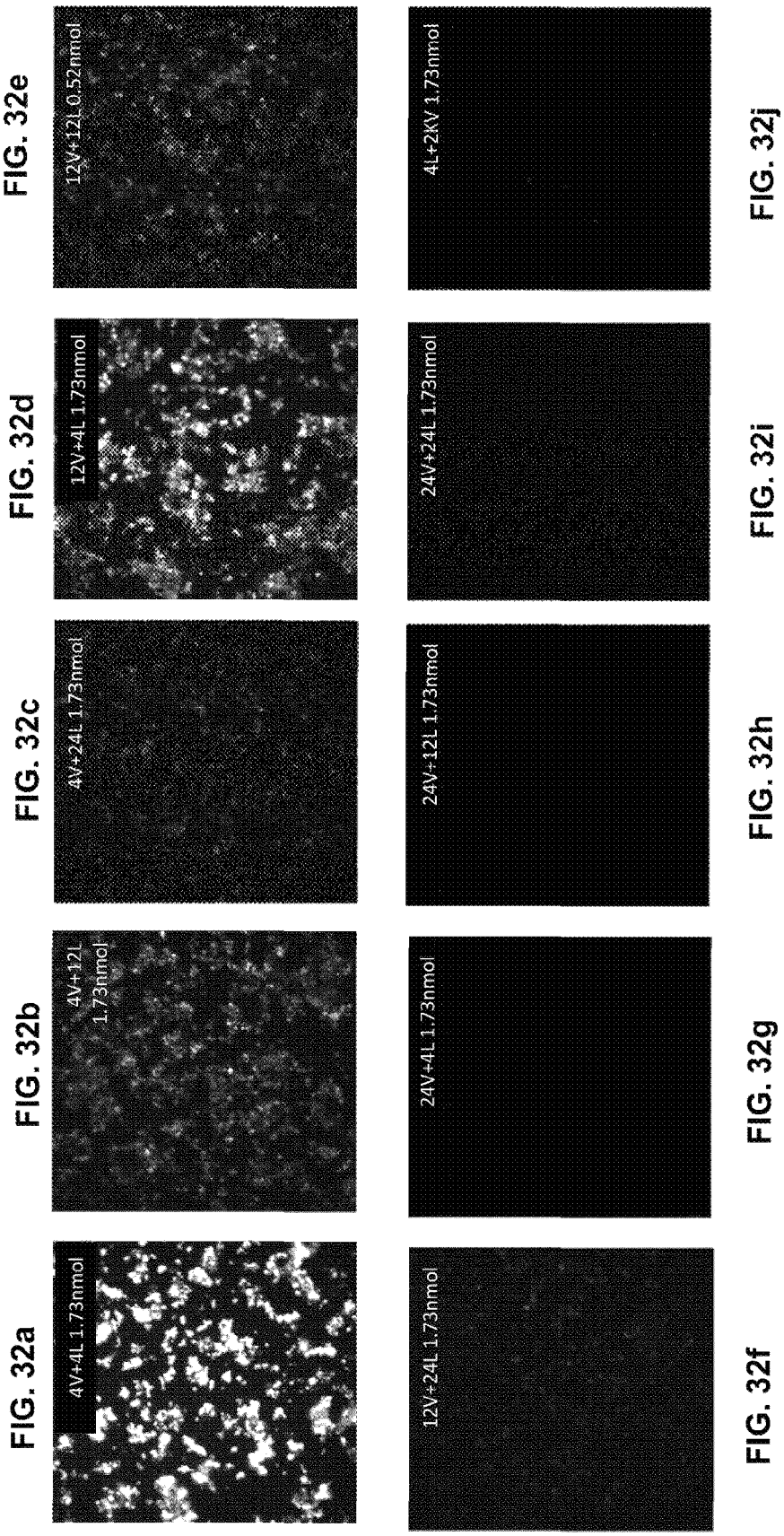

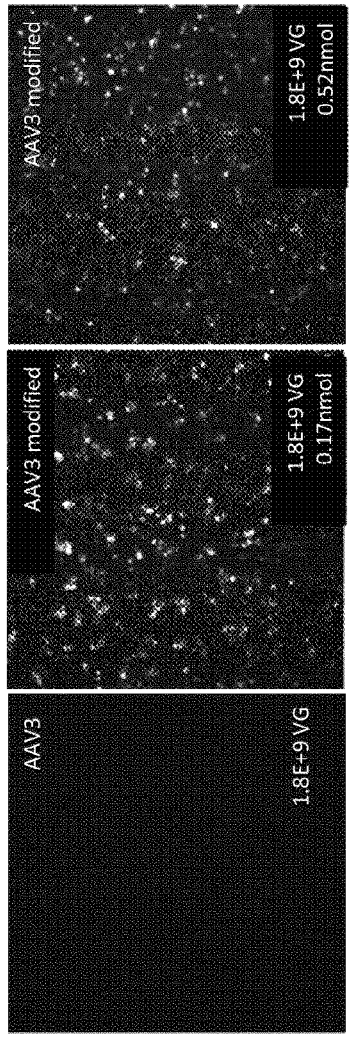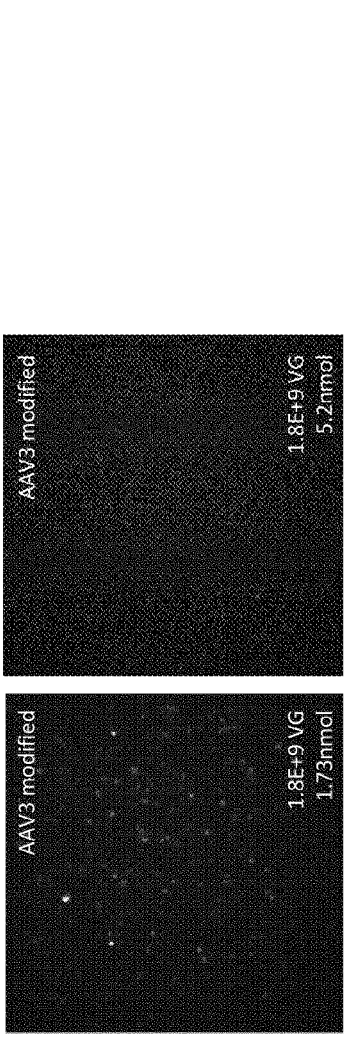

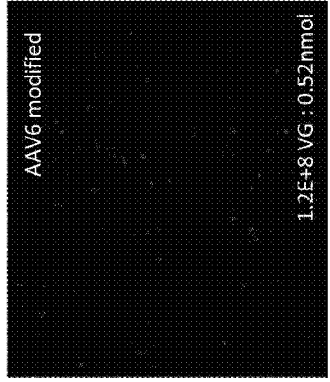
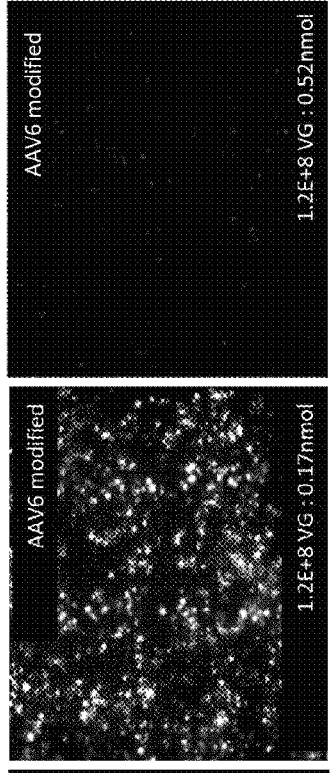
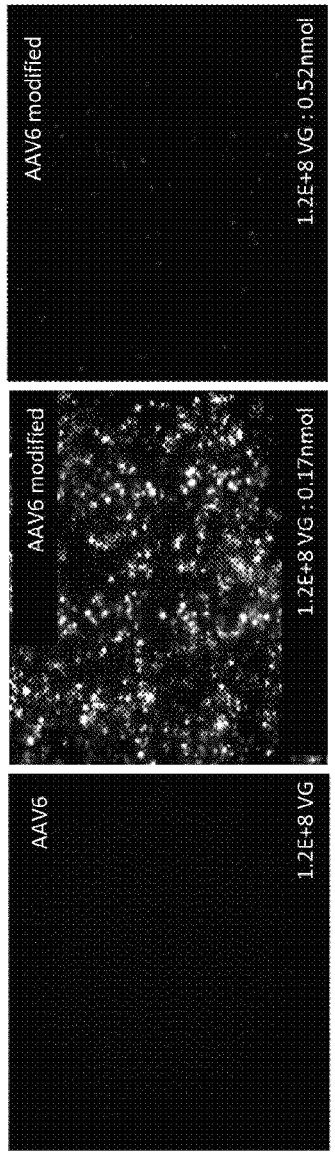
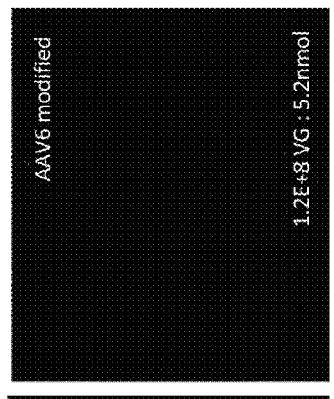
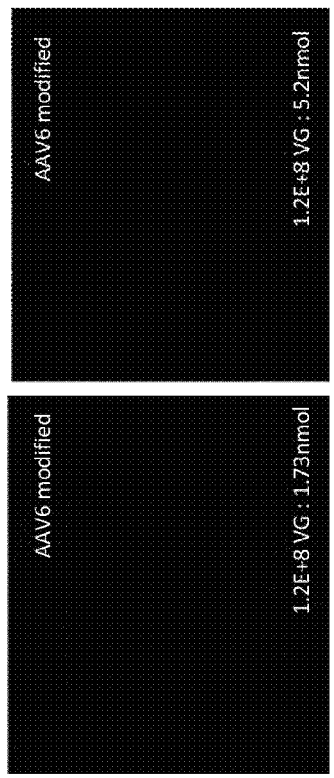

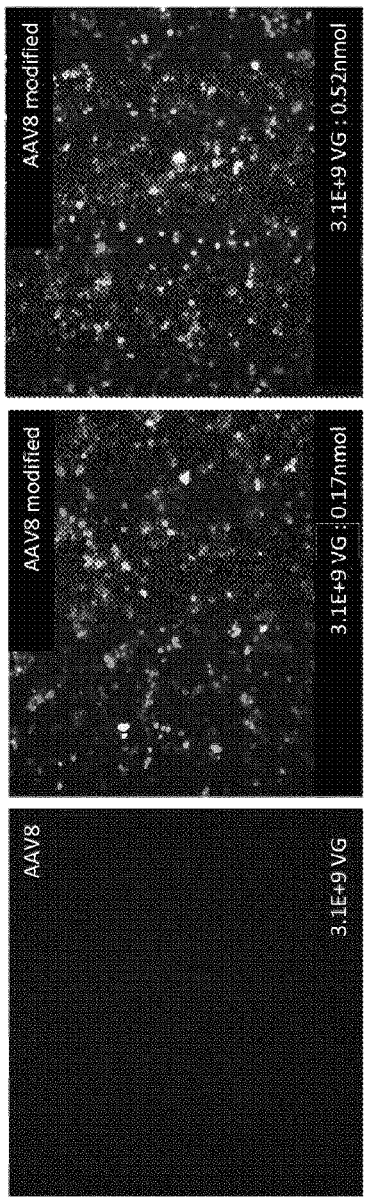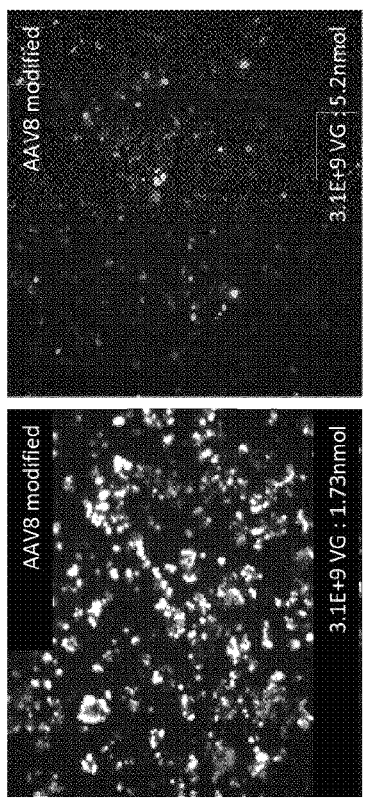

MVSAIVLYVLLAAAAHSAFAQVQLVQSGAEVKKPGASVKVSCKASGYTFTG
YIMNWVRQAPGQGLEWMGLINPYNGGTDYNPQFQDRVTITADKSTSTAY
MELSSLRSEDTAVYYCARDGYDDGPYTLETWGQGTLVTVSSGGGGSGGGG
SGGGGSDIQMTQSPSSLSASVGDRVTITCQASEDIYSFVAWYQQKPGKAP
KLLIYNAQTEAQGVPSRFSGSGSGTDFTLTISSLQPEDFATYYCQHHYDSPLT
FGGGTKVEIKSSSSGSSSSGSAALPETGGTMDKDCEMKRTTLDSPLGKLELSG
CEQGLHEIKLLGKGTSAADAVEVPAPAAVLGGPEPLMQATAVVLNAYFHQPEA
IEEFPVPALHHPVFQQESFTRQVVLWKLLKVVKFGEVISYQQLAALAGNPAATA
AVKTALSGNPVPILIPCHRVVSSSGAVGGYEGGLAVKEWLLAHEGHRLGKPGL
CTHHHHHH*

FIG. 61

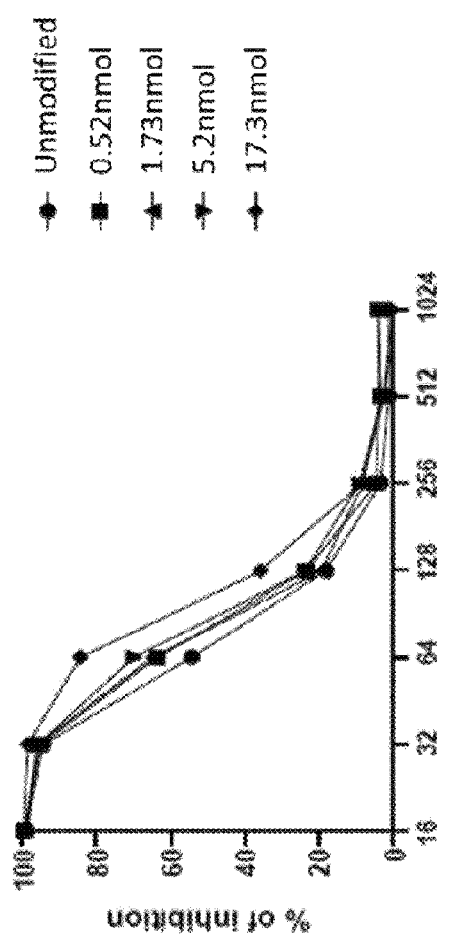
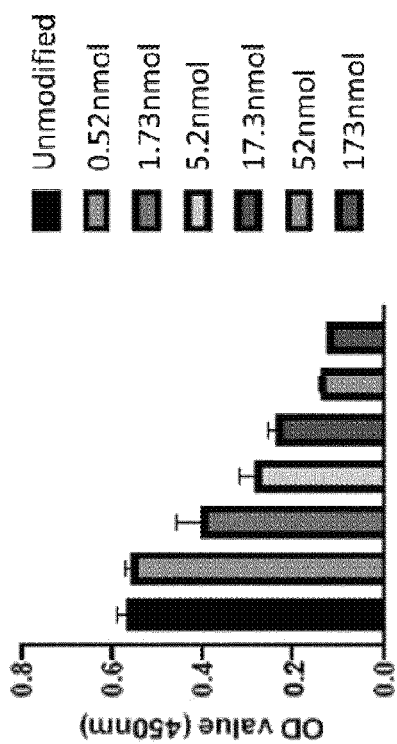
FIG. 63b
FIG. 63a

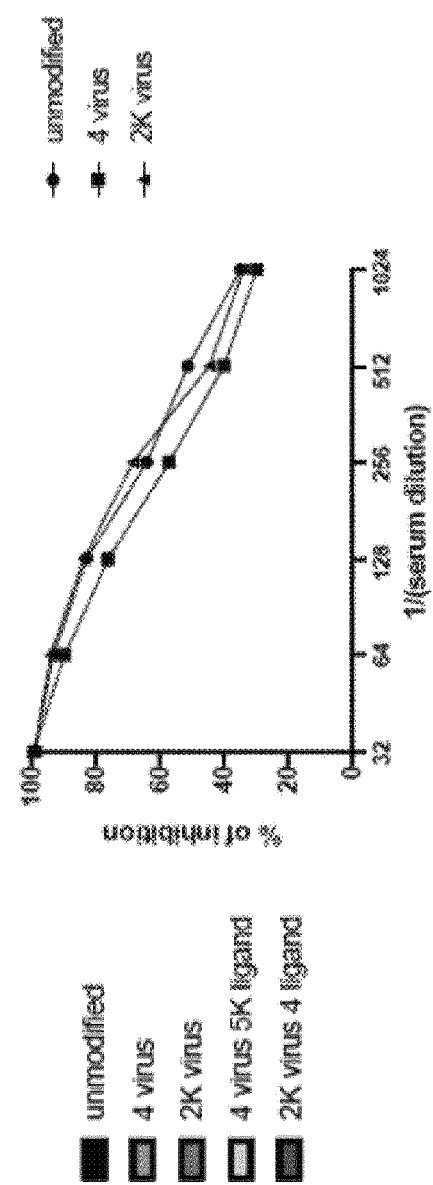
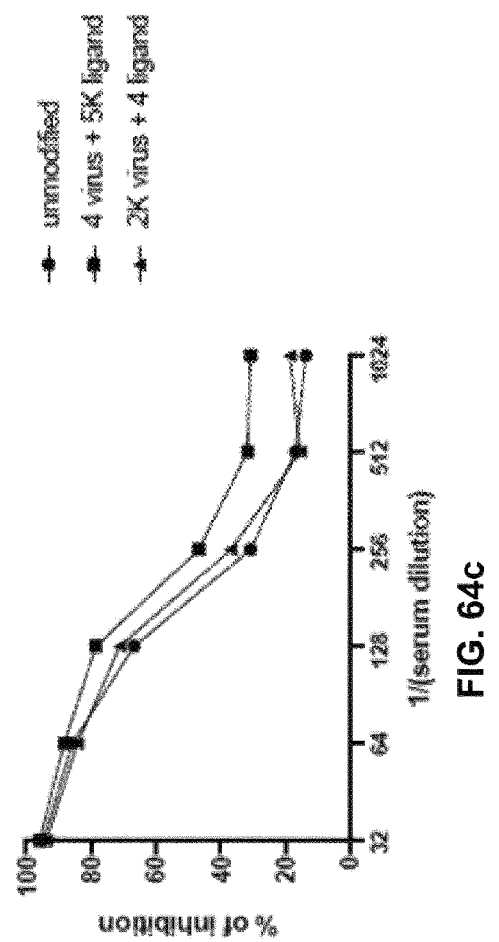
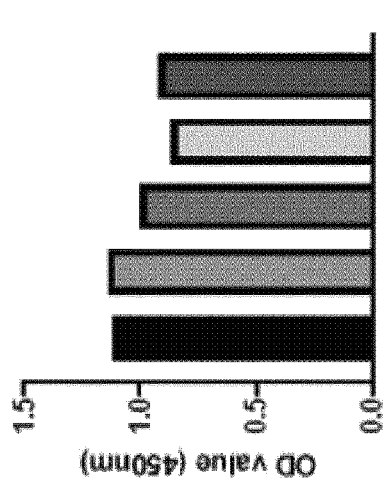
FIG. 64a
FIG. 64b
FIG. 64c

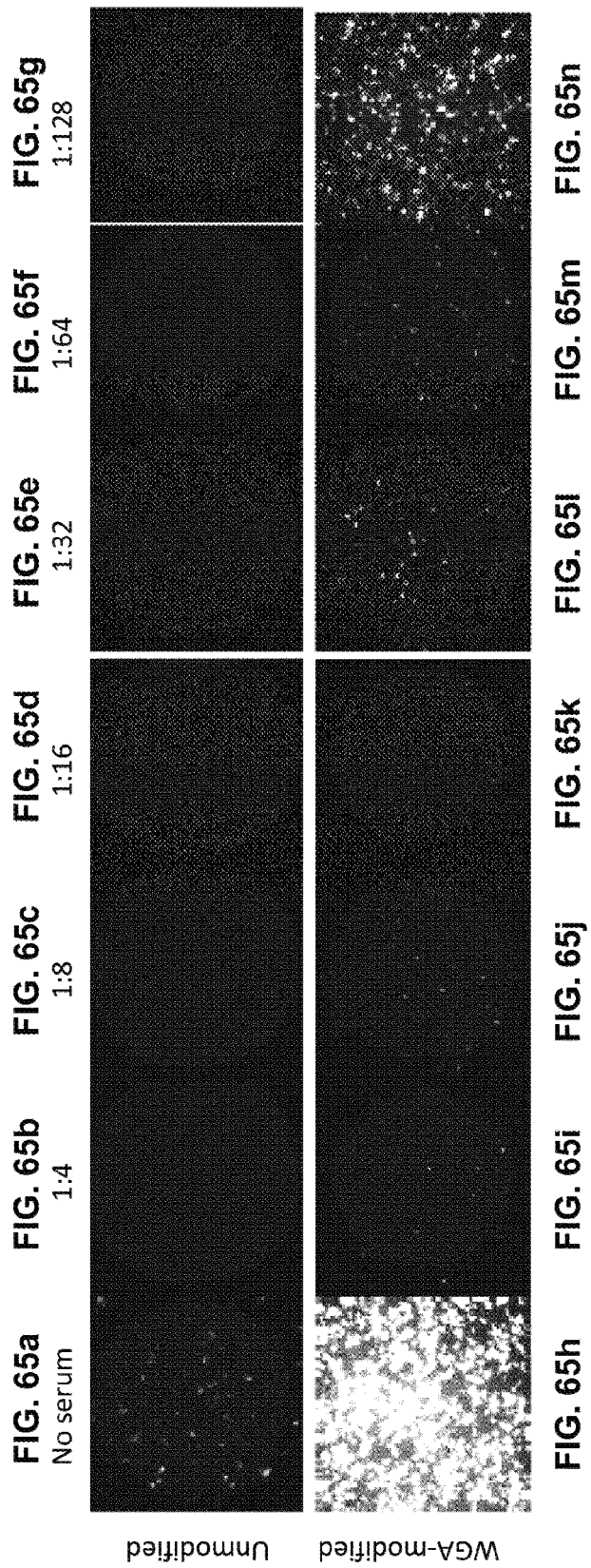

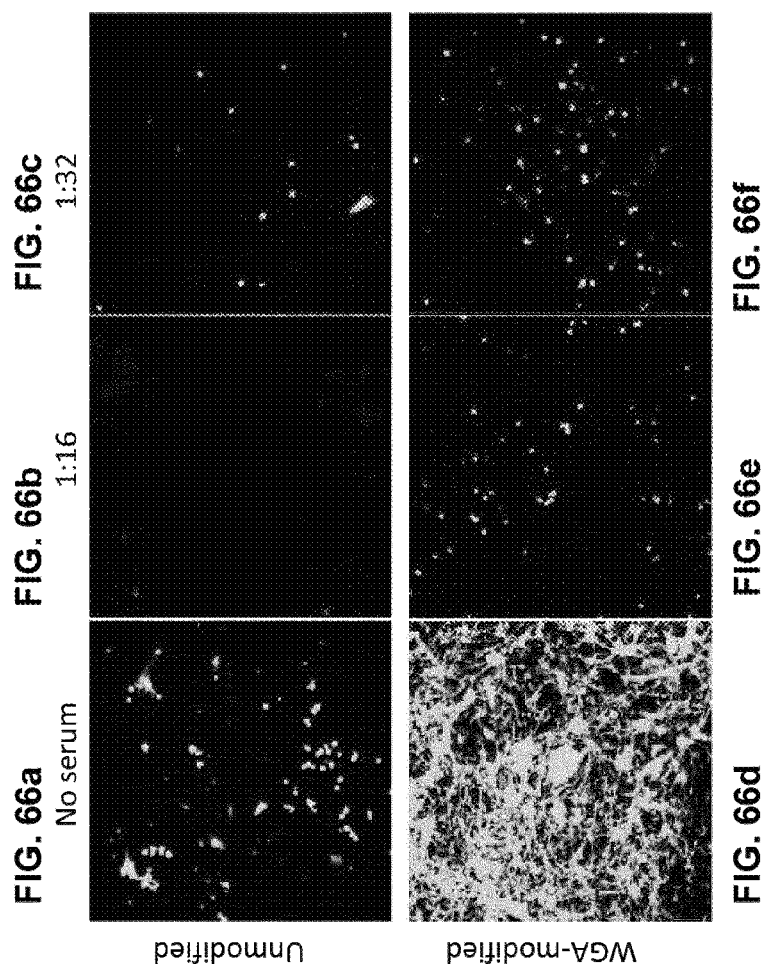

MODIFIED VIRAL PARTICLES FOR GENE THERAPY

1. CROSS-REFERENCE TO RELATED APPLICATIONS

This application is a continuation of PCT/EP2021/081424, filed Nov. 11, 2021, which claims priority to U.S. Provisional Application No. 63/112,457, filed Nov. 11, 2020, which are hereby incorporated in their entirety.

2. SEQUENCE LISTING

The instant application contains a Sequence Listing which has been submitted via Patent Center and is hereby incorporated by reference in its entirety. Said XML copy, created on May 11, 2023, is named 55167US_CRF_sequence-listing.xml, and is 7,340 bytes in size.

3. FIELD OF THE INVENTION

The present invention relates to improved surface modified viral capsids for gene delivery and gene therapy. Provided are adeno associated virus (AAV) particles that comprise a modified capsid protein. The present invention further relates, in certain embodiments, to methods for producing the improved surface modified viral capsid of this invention by removing natural binding sites in adeno associated virus (AAV) capsids and introducing ligands into said capsid to provide AAVs with enhanced transduction efficiency and/or that selectively transduce targeted cells. An additional aspect of the present invention relates to surface modified viral capsids for use in the treatment of a disease and methods for treating a disease, comprising administering the surface modified viral capsids to a subject in need thereof. Yet a further aspect of this invention relates to the surface modified viral capsids of this invention for the transfection of cells, for example as a gene delivery tool n basic research.

4. BACKGROUND OF THE INVENTION

Introduction of molecules carrying genetic information into cells is a useful tool in modern medicine and in basic research. Preferred methods include the use of gene delivery vehicles derived from viruses, including adenoviruses, retroviruses, lentiviruses, vaccinia viruses, and adeno associated viruses. Among these, recombinant adeno-associated viruses (AAV) have become the preferred viruses for in vivo gene therapy due to lack of pathogenicity, replication incompetence, and stable expression. More than 100 clinical trials are underway using AAV-based vectors, and two AAV gene therapy products have recently been approved by FDA, namely Voretigene neparvovec-rzyl (LUXTURNA) for the treatment of an inherited retinal disease and onasemnogene abeparvovec-xioi (ZOLGENSMA) for the treatment of spinal muscular atrophy.

Adeno-associated viruses are members of the genus Dependovirus of the Parvoviridae family. These viruses are non-enveloped; the viral genome is contained within an icosahedral protein capsid. Interaction of the protein capsid with mammalian cell surface polysaccharides, proteins, and glycoproteins triggers internalization of the virion by the mammalian target cell. Differences in the amino acid sequence of the protein capsid among natural AAV isolates drive different patterns of binding to mammalian cell surface proteins, and thus different patterns of cell infectivity, or tropism.

Kern et al. *J. Virology* 77 (20):11072-11081, 2003) disclose that infection of cells with adeno-associated virus (AAV) type 2 (AAV-2) is mediated by binding to heparan sulfate proteoglycan and can be competed by heparin. Mutational analysis of AAV-2 capsid proteins showed that a group of basic amino acids (arginines 484, 487, 585, and 588 and lysine 532) contribute to heparin and HeLa cell binding. These amino acids are positioned in three clusters at the threefold spike region of the AAV-2 capsid. The tissue distribution in mice of recombinant AAV-2 mutated in R484 and R585 indicated markedly reduced infection of the liver, compared to infection with wild-type recombinant AAV, but continued infection of the heart. They suggested that although heparin binding influences the infectivity of AAV-2, it seems not to be necessary. Afione et al. (J. Virology 89(3):1660-1672, 2014) conducted a similar analysis to identify the capsid residues that contribute to mammalian cell binding by AAV5.

Capsids used in current AAV gene therapies have limited utility. Poor transduction efficiency of desired tissues drives administration of high titers of recombinant virus, leading to off-target transduction and toxicity, notably liver toxicity. Another limitation of current approaches is that many current AAV capsids are ineffective at transducing specific cell types to which the genetic cargo must be delivered for effective therapy.

A variety of approaches are being employed to engineer modified capsids that alter the cell binding specificity of recombinant AAV for use in gene therapy.

One approach is to search for new natural isolates in humans, non-human primates, and other mammals See, e.g., WO 2018/160582; WO 2015/121501; WO 2020/223232. These approaches provide no certainty that a capsid will be discovered that has the desired tropism.

Another approach is to mutate the primary amino acid sequence of the capsid proteins via substitutions without peptide insertion. Typically, libraries are constructed with random amino acid mutations clustered in a desired region of the capsid surface. The library is then screened in vivo and capsids capable of transducing specific tissues and cells identified by recovery from specific tissues. A related approach is to apply in silico methods to extrapolate from capsid sequences of known AAV isolates to predict new functional capsids that may have altered tissue and cell-type tropism. These predicted capsids are then synthesized and screened in vivo for patterns of tissue transduction. See, e.g., U.S. Pat. Nos. 9,695,220; 10,738,087; and WO 2019/217911. These empirical approaches rely on manufacture of high complexity libraries and empirical assessment. As a consequence, identification of desired tropism relies on serendipity.

A more directed approach is to alter the amino acid sequence of the capsid proteins by insertion of a peptide known to bind to a specific cell type, via in-frame insertion of the cell-targeting peptide coding region into the capsid (CAP) gene. See, e.g., WO 2019/207132; WO 2021/077000; WO 2017/100671; and WO 2020/068990. This approach has limitations, however: the insertions must be positioned so as to not interfere significantly with virion assembly during production of the recombinant product and must be so located on the viral capsid as to drive productive interaction with the mammalian cell surface target and subsequent internalization.

In addition, all of these approaches to capsid engineering generate entirely new protein capsids that cannot be deployed in gene therapy without extensive preclinical and clinical characterization.

There is a need for new methods of altering the tissue specificity of AAV capsids that does not rely on serendipitous discovery and that does not reduce efficiency of production or, upon administration, reduce transduction efficiency.

WO 2020/225363 discloses methods for post-assembly modification of AAV capsids of intact virions using chemical conjugation of ligands with known cell-targeting specificity, and discloses surface-modified capsids prepared by these methods. There is a need to expand and optimize such post-assembly modification approaches.

5. SUMMARY OF THE INVENTION

In view of the above limitations, there remains a need to develop new viral platforms with a higher transduction efficiency and specificity for relevant target tissues that would improve transduction of specific cells of interest and/or that can be efficacious when delivered at a lower titer.

One aspect of the present invention is the chemical modification of a virus capsid to accept a ligand attachment and attaching a ligand of interest to said capsid. In some embodiments, natural binding sites in the AAV capsid are removed prior to modifying the virus to accept the ligand attachment.

In an aspect of the present disclosure, a surface modified viral capsid is provided, comprising one or more of: a ligand covalently conjugated to a viral capsid protein via a linker, the linker comprising: a crosslinked moiety, wherein the crosslinked moiety is formed by a reaction between first and second members of a crosslinker reactive pair; and one or more optional spacers.

In some embodiments, the first and second members of the crosslinker reactive pair participate in a reaction selected from: a Cu(I)-catalyzed azide-alkyne cycloaddition (CuAAC) reaction, a strain-promoted alkyne-azide cycloaddition (SPAAC) reaction, a strain-promoted alkyne-nitrone cycloaddition (SPANC) reaction, an inverse electron demand Diels-Alder (IEEDD) reaction, and a Staudinger ligation and a [4+1] cycloaddition reaction.

In some embodiments, the crosslinked moiety comprises at least one of: an eight membered ring and a triazole ring. In certain embodiments, the crosslinked moiety comprises both an eight membered ring and a triazole ring fused to form a bicyclic moiety.

In some embodiments, the reaction is a strain-promoted alkyne-azide cycloaddition (SPAAC) reaction. In certain of these embodiments, the crosslinker reactive pair comprise a cyclooctyne and an azide. In certain embodiments, the cyclooctyne is selected from dibenzylcyclooctyne (DIBO), dibenzoazacyclooctyne (DBCO), and biarylazacyclooctynone (BARAC), or a derivative thereof. In certain embodiments, the cyclooctyne is a DBCO.

In some embodiments, the crosslinked moiety comprises the following structure:

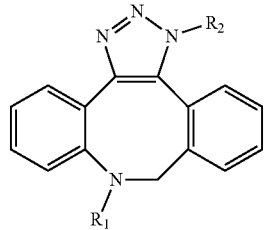

wherein $R_1$ and $R_2$ indicate the points of attachment to the linker.

In some embodiments, the reaction is an inverse electron demand Diels-Alder (IEEDD) reaction. In certain of these embodiments, the crosslinker reactive pair comprise a transcyclooctene and a tetrazine.

In some embodiments, the crosslinked moiety comprises the following structure

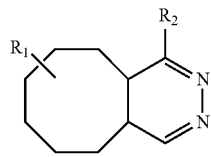

wherein $R_1$ and $R_2$ indicate the points of attachment to the linker.

In some embodiments, the linker comprises one or more spacers. In certain embodiments, the one or more spacers are ethylene glycol monomers and the total number of ethylene monomers in the linker between the virus and the ligand sum to less than 50 monomers. In certain embodiments, the total number of ethylene monomers in the linker between the virus and the ligand sum to less than 25 monomers. In alternative embodiments, the one or more spacers comprise from 1 to 20 monomers of ethylene glycol. In certain embodiments, each one of the one or more spacers comprise from 2 to 8 monomers of ethylene glycol. In certain embodiments, each one of the one or more spacers comprise 4 monomers of ethylene glycol. In certain embodiments, the linker comprises at least two spacers that comprise 4 monomers of polyethylene glycol, each.

In some embodiments, the ligand is a cell-type specific ligand. In certain embodiments, the ligand is selected from cytokines, growth factors, lectins, toxins, single chain antibodies, peptides and combinations thereof.

In some embodiments, the linker is covalently attached to a primary amino group of the capsid protein primary sequence. In certain embodiments, the primary amino group is selected from an N-terminal amino group, a lysine amino acid residue and an arginine amino acid residue. In certain embodiments, the primary amino group is a side chain of a lysine amino acid residue.

In some embodiments, the linker is covalently attached to the ligand via a primary amino group of the ligand.

In some embodiments, the linker is covalently attached to the ligand via a non-natural amino acid residue of the primary sequence of the ligand. In certain embodiments, the non-natural amino acid residue comprises a member of the crosslinker reactive pair that participates in a reaction selected from: a Cu(I)-catalyzed azide-alkyne cycloaddition (CuAAC) reaction, a strain-promoted alkyne-azide cycloaddition (SPARC) reaction, a strain-promoted alkyne-nitrone cycloaddition (SPANC) reaction, an inverse electron demand Diels-Alder (IEEDD) reaction, a Staudinger ligation and a [4+1] cycloaddition reaction. In certain embodiments, the crosslinker reactive pair comprises an azide, cyclooctyne, cyclooctene or 1,2,4,5 tetrazine moiety.

In alternative embodiments, the linker is part of a fusion protein of the ligand and linker.

In some embodiments, the surface modified viral capsid comprises one or more native polysaccharide binding sites. In some embodiments, the viral capsid has not been modified to remove a native polysaccharide binding site. In certain embodiments, the surface modified viral capsid is characterized by increased infectivity compared to an unmodified viral capsid of the same serotype.

In some embodiments, the viral capsid has been modified to remove one or more native polysaccharide binding sites. In certain embodiments, removal is via mutation of amino acids known to mediate binding of heparin sulfate. In certain embodiments, the surface modified viral capsid is characterized by altered tropism compared to an unmodified viral capsid. In certain embodiments, the surface modified viral capsid is characterized by improved transduction efficiency compared to an unmodified viral capsid.

In some embodiments, the viral capsid is selected from an adenovirus capsid, adeno-associated virus capsid, retro virus capsid, lentivirus capsid, herpes simplex virus capsid, and a baculovirus capsid.

In some embodiments, the viral capsid is an adeno-associated virus (AAV) capsid. In certain embodiments, at least one of the arginine residues at 585 and 588 of VP1, or analogous positions in VP2 or VP3, have been mutated. In certain embodiments, the arginine residues at 585 and 588 of VP1, have been mutated to alanine residues.

In some embodiments, the surface modified viral capsid, further comprises dispersed PEG oligomers or PEG polymers linked to the surface of the capsid. In some embodiments, the surface modified viral capsid demonstrates evasion of pre-existing neutralizing antibodies, lower immunogenicity and immune stealth.

In an aspect of the present disclosure, a surface modified viral capsid is provided comprising a viral capsid protein linked to a ligand according to Formula I:

$$\blacksquare\!\!-\!\!\left(Y\!-\!\left[PEG\right]_{n}\!-\!Sp\!-\!Q\!-\!Sp'\!-\!\left[PEG\right]_{n'}\!-\!Y'\!-\!L\right)_{x} \quad (I)$$

wherein:

■ is a viral capsid;
Y and Y' are independently an attachment moiety;
n and n' are independently 0 or an integer from 1 to 50,
Sp and Sp' are independently an optional spacer;
L is a ligand;
x is the ratio of ligand to viral capsid and is in a range from 50 to 250; and
Q is selected from:

wherein, Z is a 7 or 8 membered cyclic or heterocyclic structure. In certain embodiments, x ranges from 80 to 120.

In an aspect of the present disclosure, a surface modified viral capsid is provided, comprising a viral capsid protein linked to a ligand according to Formula I-1:

(I-1)

wherein:

⬢ is a viral capsid;
n and n' are independently an integer from 0 to 30;
L is a ligand; and
x is an integer from 1 to 300.

In an aspect of the present disclosure, a composition is provided comprising a surface modified viral capsid as provided herein, wherein the average ligand to viral capsid ratio is from 50 to 250.

In an aspect of the present disclosure, a pharmaceutical composition is provided comprising a virion, the virion comprising a surface modified viral capsid as provided herein, further comprising a pharmaceutically acceptable carrier.

In an aspect of the present disclosure a method of treating a patient having a genetic abnormality, the method comprising administering the pharmaceutical composition comprising a virion, the virion comprising a surface modified viral capsid as provided herein, further comprising a pharmaceutically acceptable carrier.

In an aspect of the present disclosure, a surface functionalized viral capsid is provided comprising a member of a crosslinker reactive pair and optionally one or more of a spacer, wherein the surface functionalized viral capsid is suitable for reaction with a functionalized ligand, the ligand comprising a member of the crosslinker reactive pair, wherein the members of the crosslinker reactive pair participate in a reaction selected from: a Cu(I)-catalyzed azide-alkyne cycloaddition (CuAAC) reaction, a strain-promoted alkyne-azide cycloaddition (SPAAC) reaction, a strain-promoted alkyne-nitrone cycloaddition (SPANC) reaction, an inverse electron demand Diels-Alder (IEEDD) reaction, and a Staudinger ligation and a [4+1] cycloaddition reaction.

An aspect of the present disclosure provides a method of a making a surface modified viral capsid described herein, the method comprising the steps:
  i) obtaining a surface functionalized viral capsid by reacting a viral capsid protein with a capsid-reactive linker comprising a first member of a crosslinker reactive pair and optionally one or more of a spacer;
  ii) conjugating the surface functionalized viral capsid with a functionalized ligand comprising a second member of the crosslinker reactive pair and optionally one or more of a spacer,
  wherein the first and second members of the crosslinker reactive pair react to form a crosslinked moiety, Q; and
  iii) obtaining the surface modified viral capsid.

Preferred features of each aspect of the invention are as for each of the other aspects mutatis mutandis. The cited documents mentioned herein are incorporated to the fullest extent permitted by law. Although the present invention and its advantages have been described in detail, it should be understood that various changes, substitutions and alterations can be made herein without departing from the spirit and scope of the invention as defined in the appended claims.

6. BRIEF DESCRIPTION OF THE SEVERAL VIEWS OF THE DRAWINGS

A better understanding of the features, aspects, and advantages of the present disclosure will become better understood with regard to the following detailed description that sets forth illustrative embodiments, in which the principles of the invention are utilized, and accompanying drawings of which:

Figure 4C:
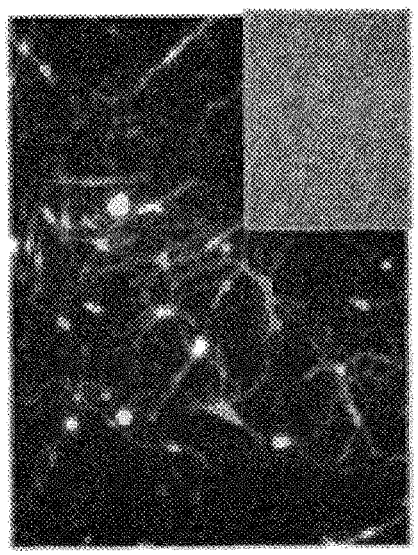
Figure 4B:
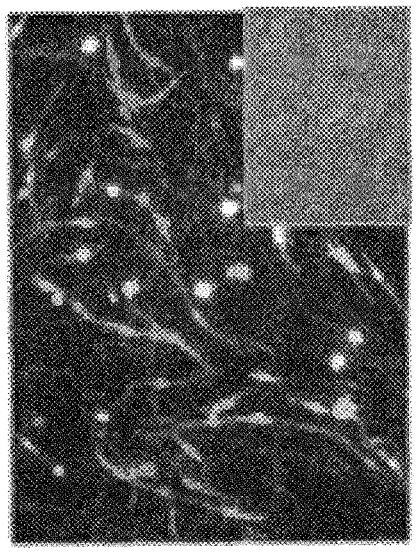
Figure 4A:
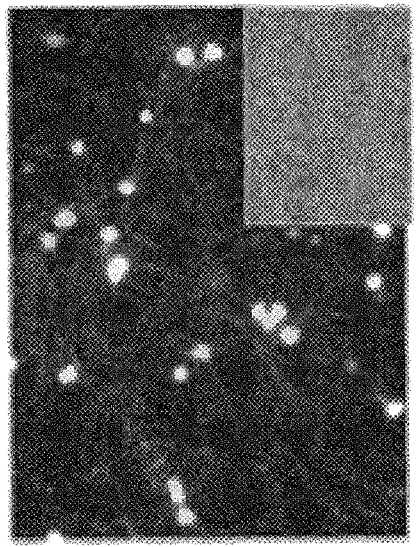

FIGS. 4a-4c show that neurotrophic factors NGF (FIG. 4a), NT3 (FIG. 4b) and BDNF (FIG. 4c) deliver virus to different neuronal populations when conjugated to the capsid surface. The insets show the phase contrast microscopic image of the cells. The constructs were tested on sensory neurons in a fluorescent reporter mouse model in analogy to FIG. 2.

Figure 5:
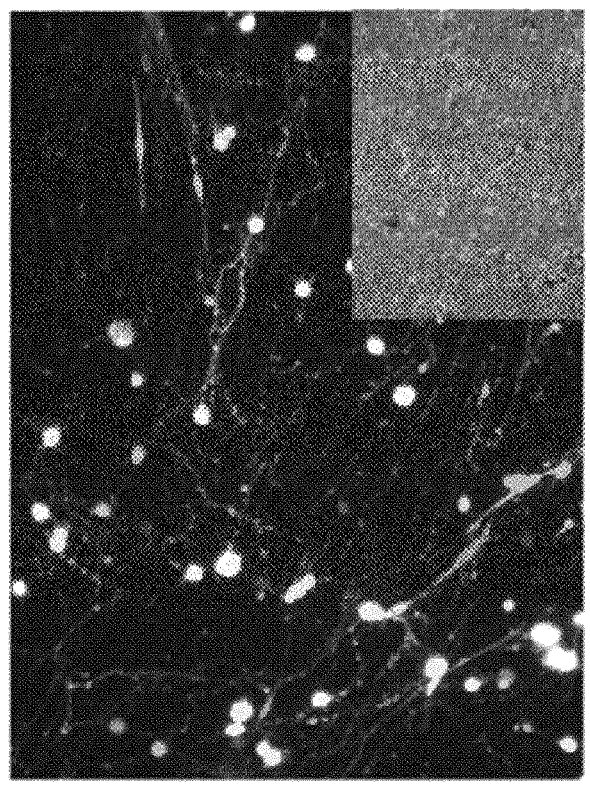

FIG. 5 shows that the capsid surface modified with a cholera toxin B subunit transported virus retrogradely to neuronal cell bodies when injected into the skin. The inset shows the microscopic image of the cells. The construct was tested on sensory neurons in a fluorescent reporter mouse model in analogy to FIG. 2.

Figure 6C:
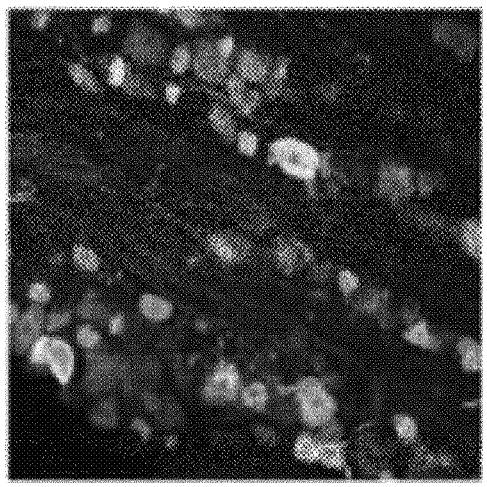
Figure 6B:
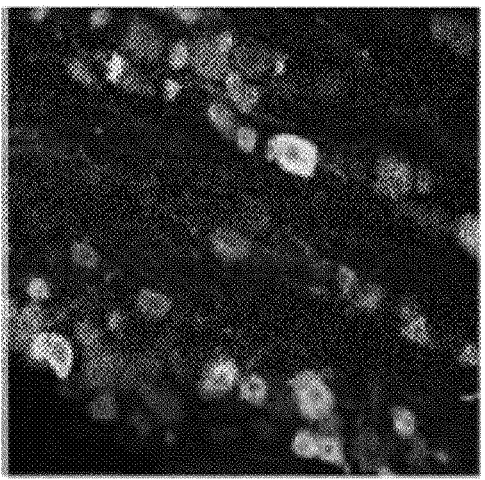
Figure 6A:
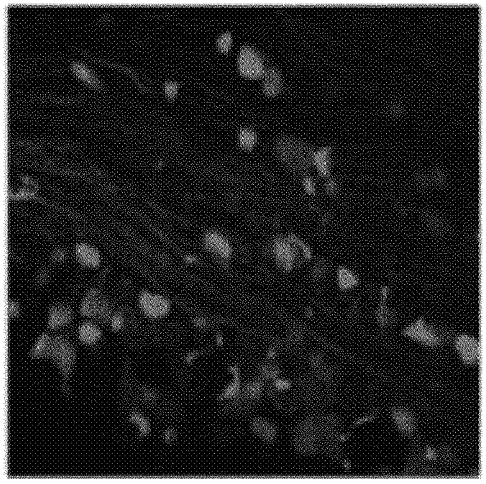

FIGS. 6a-6c show sensory neuron tissue in the trigeminal ganglia three weeks after injection with a virus with NGF ligand IV according to the invention (FIG. 6a), stained with an antibody against TrkA (the receptor for NGF, FIG. 6b). An overlap of at least 80% can be seen (FIG. 6c).

Figure 7:

FIG. 7 shows a staining of the sections from FIG. 6a with antibodies against NF200 and IB4, which mainly mark other neurons (mechanoreceptors (green/grey) and non-peptidergic nociceptors, respectively (blue/dark grey)). The red (light grey) infected cells are mainly different from the green and blue cells.

Figure 8B:
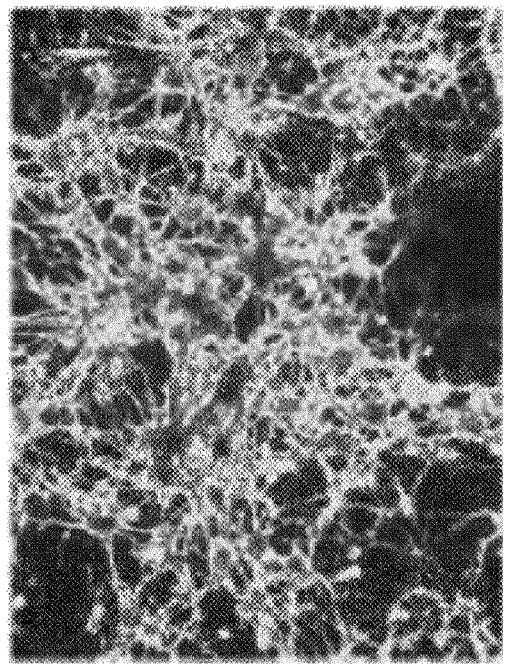
Figure 8A:
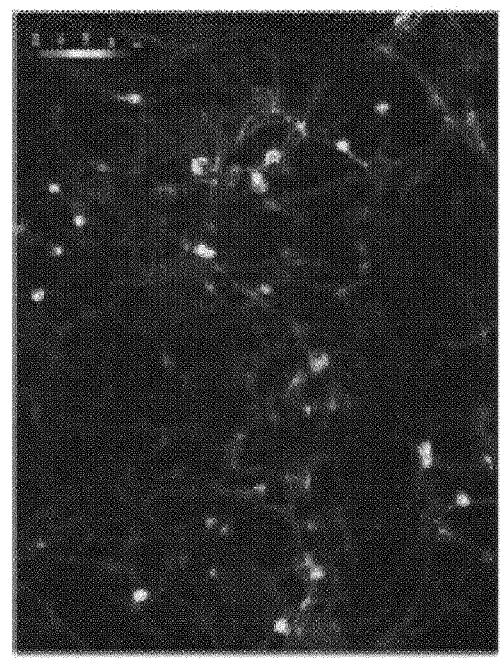
Figure 9C:
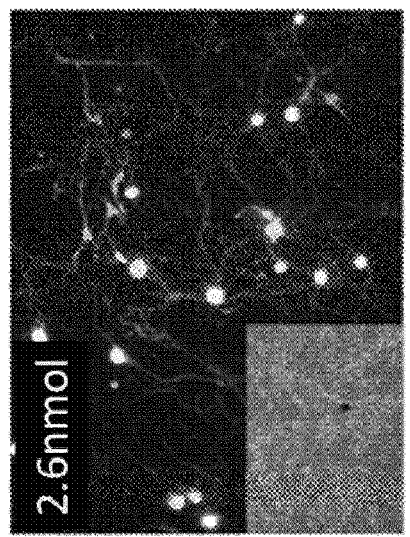
Figure 9B:
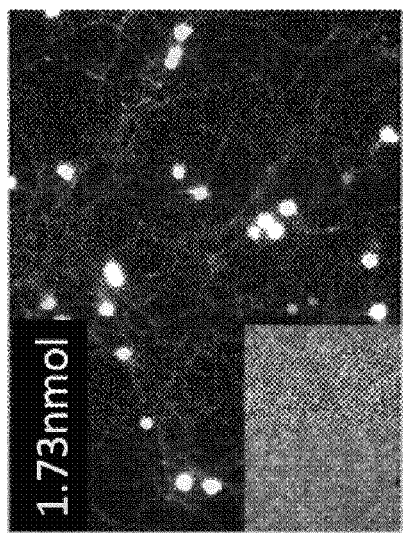
Figure 9A:
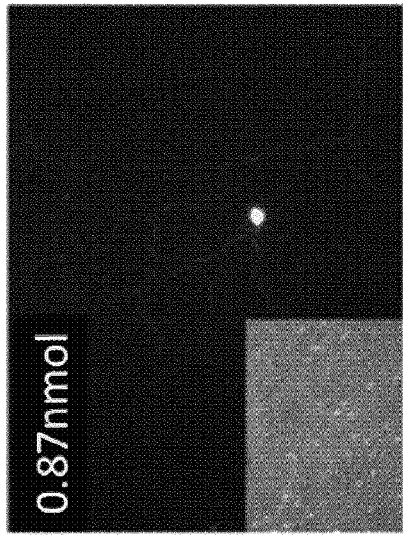
Figure 9F:
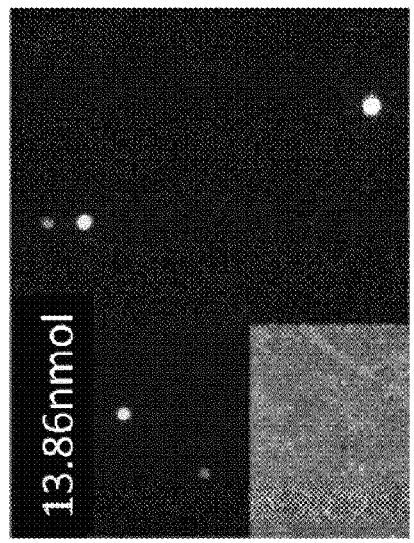
Figure 9E:
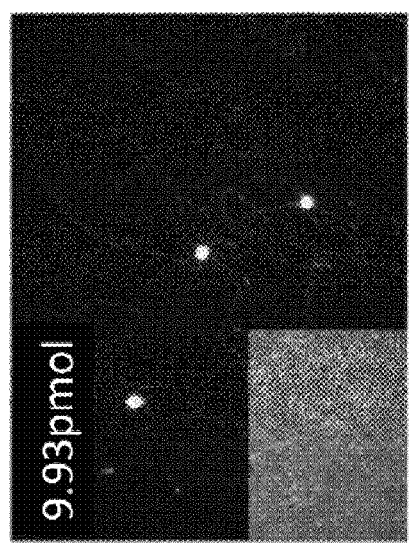
Figure 9D:
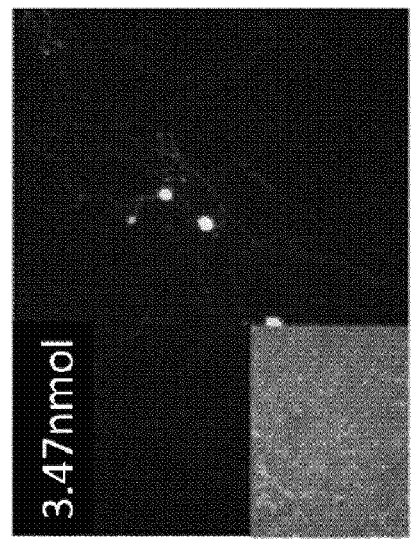

FIGS. 8a-8b shows that gene delivery is more efficient with liganded viruses. FIG. 8a shows normal AAV9 variant PHP.S; FIG. 8b shows the PHP.S variant of FIG. 8a further modified with WGA. WGA modified construct resulted in a strong increase of delivery.

FIGS. 9a-9f show $NGF^{R121W}$-SNAP::AAV2-• HSPG transduction of DRG neurons at different modification ratios. Inset shows phase contrast image.

Figure 10C:
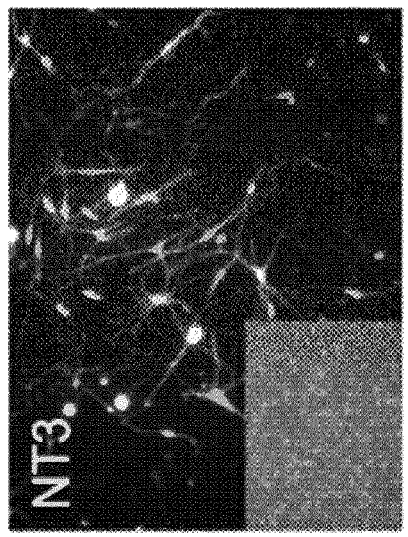
Figure 10B:
Figure 10A:
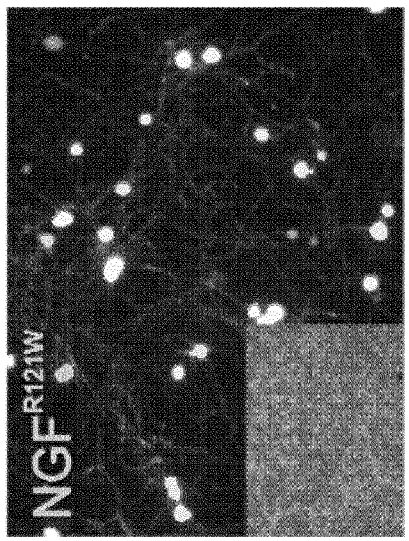

FIGS. 10a-10c show neurotrophin-AAV2-• HSPG transduction of DRG neurons. FIGS. 10a-10c show $NGF^{R121W}$, BDNF and NT3 (respectively) coupled AAV2-• HSPG targets morphologically distinct subtypes of cell.

Figure 11C:
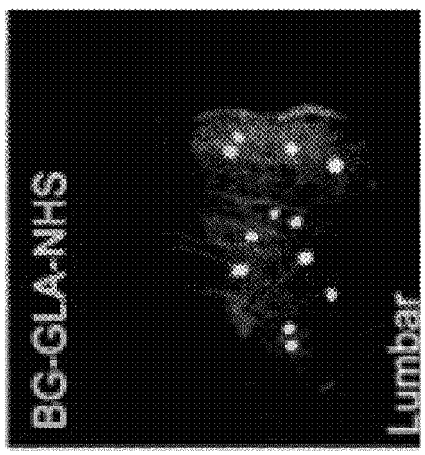
Figure 11B:
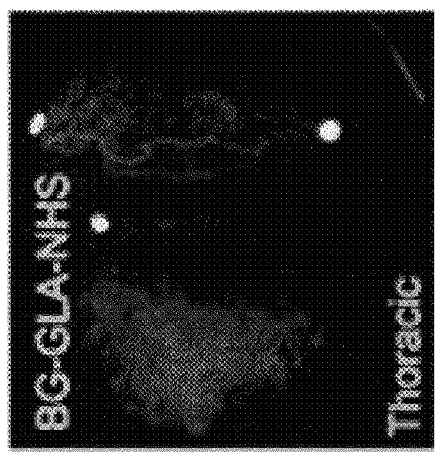
Figure 11A:
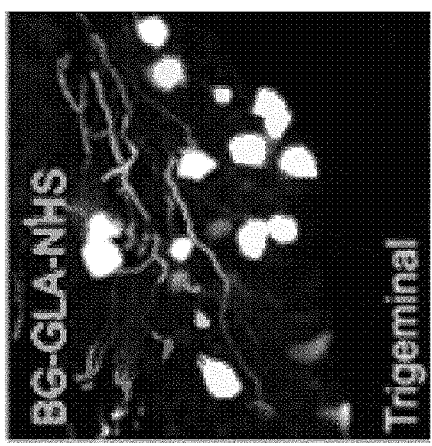
Figure 11F:
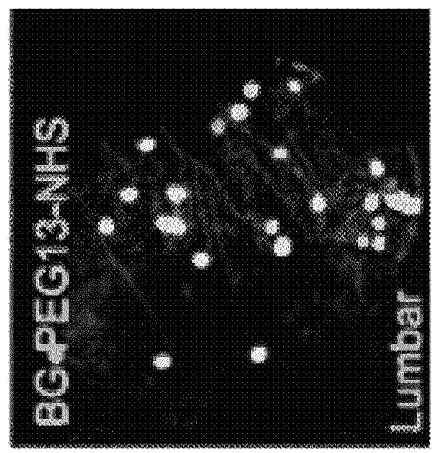
Figure 11E:
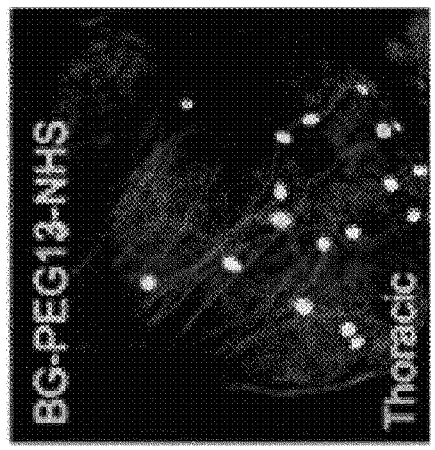
Figure 11D:
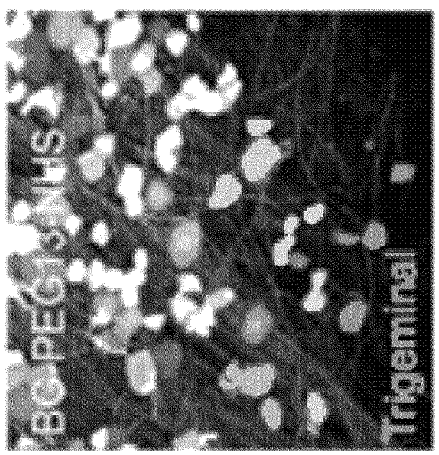

FIGS. 11a-11f show the influence of linker length on transduction efficiency of $NGF^{R121W}$-SNAP::AAV2-• HSPG across different sensory ganglia. 3E+10 viral genomes (VG) injected retro orbital. FIGS. 11a-11c show the results for the shorter BG-GLA linker, FIGS. 11d-11f show results for the longer BG-PEG13 linker.

Figure 12D:
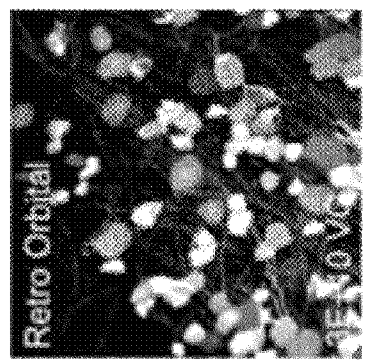
Figure 12C:
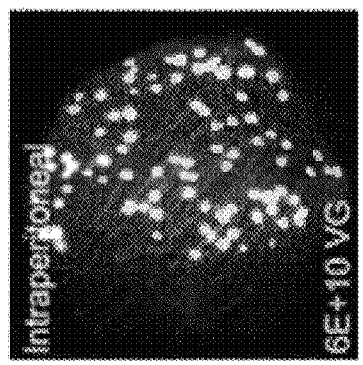
Figure 12B:
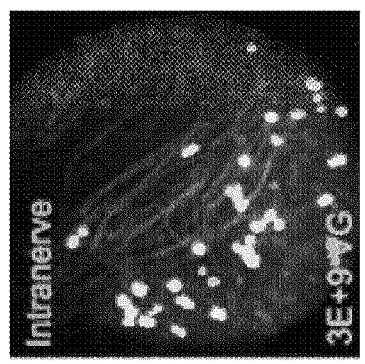
Figure 12A:
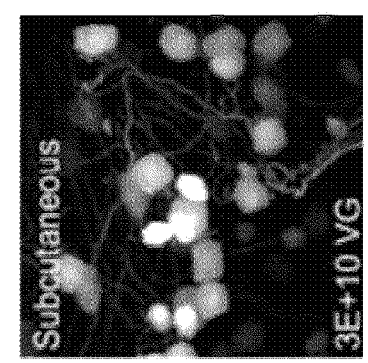

FIGS. 12a-12d show the influence of injection route on transduction efficiency in the DRG. Histological analysis of transduction efficiency in the DRG for different injection routes. Local injection in the skin (FIG. 12a) or nerve (FIG. 12b). Systemic injection IP (FIG. 12c) or IV (FIG. 12d).

Figure 13C:
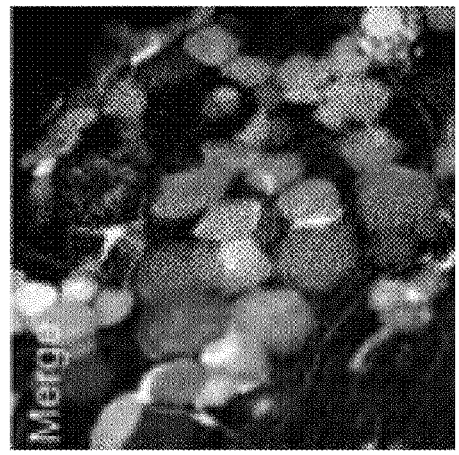
Figure 13B:
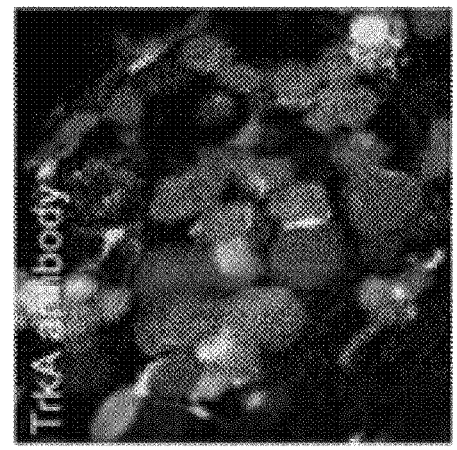
Figure 13A:
Figure 13D:
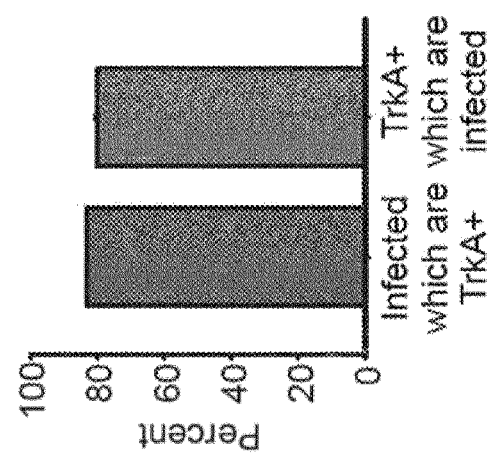

FIGS. 13a-13d confirm the selectivity of NGF$^{R121W}$-SNAP::AAV2-• HSPG for TrkA+ cells in the DRG. Histological analysis of transduction selectivity in the DRG following retroorbital injection of 3E+10 VG particles: FIG. 13a shows fluorescent tdTomato signal from NGF$^{R121W}$-SNAP::AAV2-• HSPG (red); FIG. 13b shows TrkA+ cells in green identified using an antibody against TrkA (green); FIG. 13c is the merged image (orange). FIG. 13d quantifies the of number of infected cells that are TrkA positive cells and the number of TrkA positive cells that are infected.

Figure 14C:
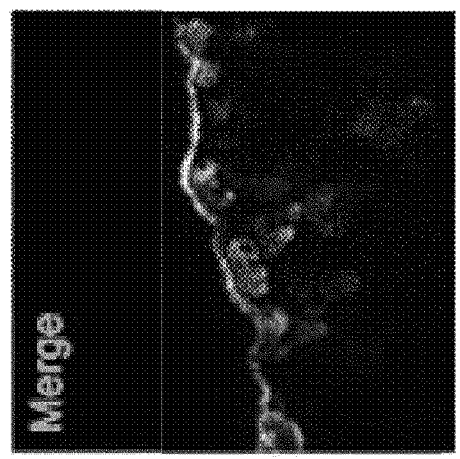
Figure 14B:
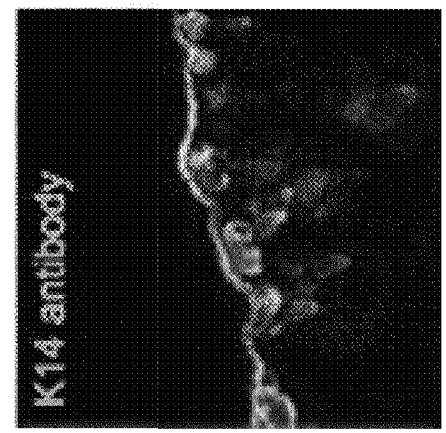
Figure 14A:
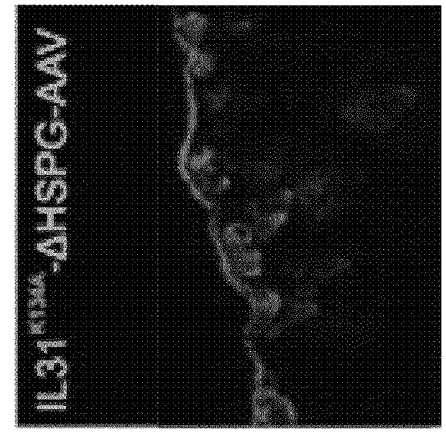

FIGS. 14a-14c show IL31$^{K134A}$-AAV2-• HSPG infection of wildtype mouse keratinoyctes in vivo. Histological analysis of transduction selectivity in the skin of wildtype mice following subcutaneous injection of 3E+10 VG particles: FIG. 14a shows fluorescent tdTomato signal from IL31$^{K134A}$ SNAP::AAV2-• HSPG (red). FIG. 14b shows keratinocytes identified using an antibody against K14 (green). FIG. 14c shows the merged image (orange).

Figure 15C:
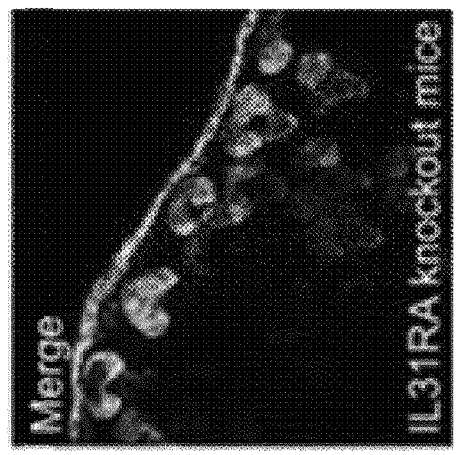
Figure 15B:
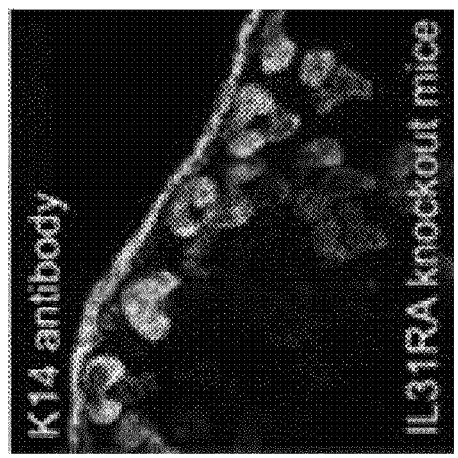
Figure 15A:
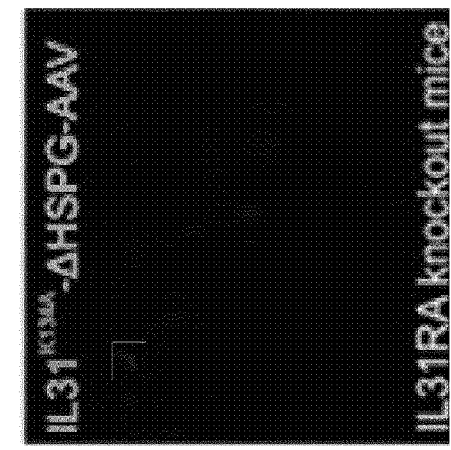

FIGS. 15a-15c show that IL31$^{K134A}$-AAV2-• HSPG does not infect keratinoyctes in the absence of the Il31RA receptor. Histological analysis of transduction selectivity in the skin of IL31RA−/− mice following subcutaneous injection of 3E+10 VG particles: FIG. 15a shows the absence of fluorescent signal from IL31$^{K134A}$::AAV2-• HSPG. FIG. 15b shows keratinocytes identified using an antibody against K14 (green). FIG. 15c shows the merged image (orange).

Figure 16C:
Figure 16B:
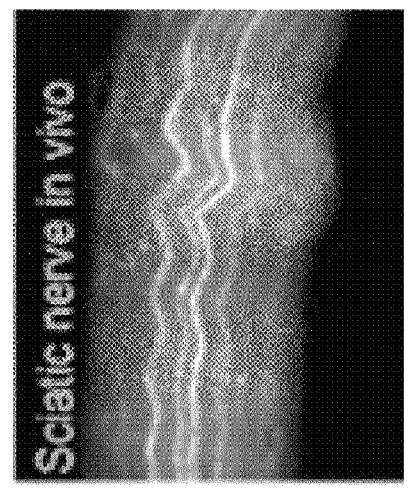
Figure 16A:

FIGS. 16a-16c show CTB-• HSPG-AAV transduction in vitro and in vivo.

Figure 17B:
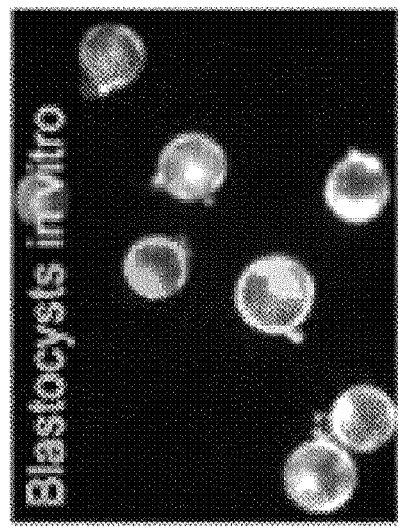
Figure 17A:
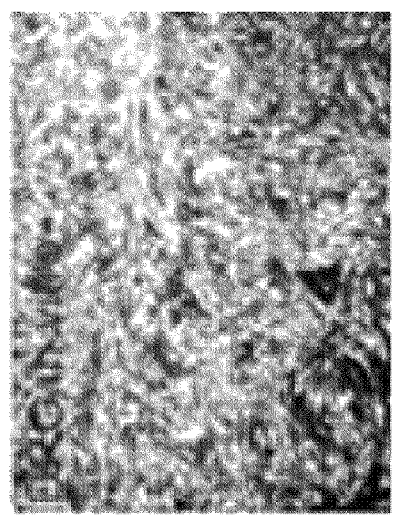

FIGS. 17a-17b show WGA-• HSPG-AAV transduction in vitro.

Figure 18C:
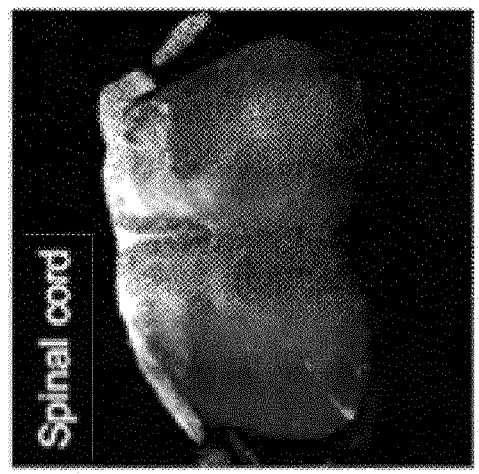
Figure 18B:
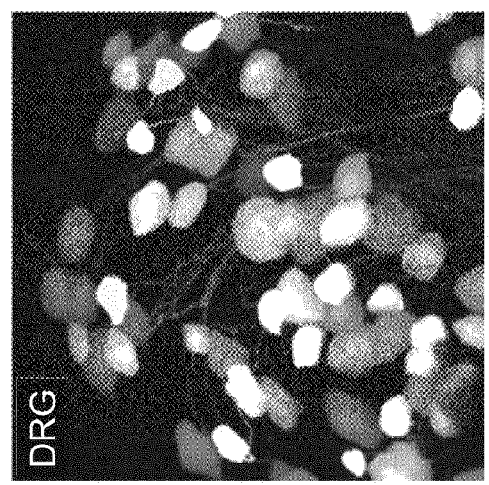
Figure 18A:
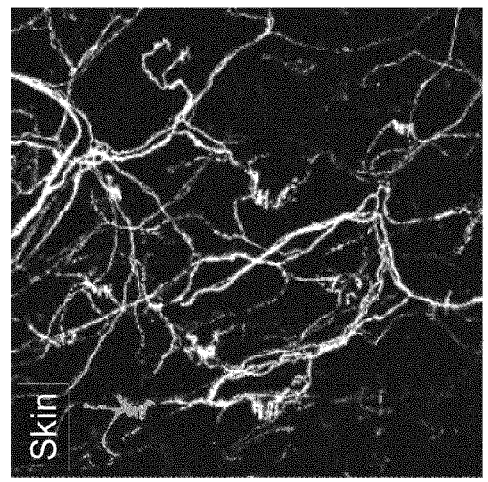

FIGS. 18a-18c show neonatal IV injection of WGA::AAV2-• HSPG. 1E+9 VG of WGA::AAV2-• HSPG was injected in IV in neonatal mice. Robust tdTomato fluorescence was observed in neurons in the skin (FIG. 18a), DRG (FIG. 18b) and spinal cord (FIG. 18c).

Figure 19C:
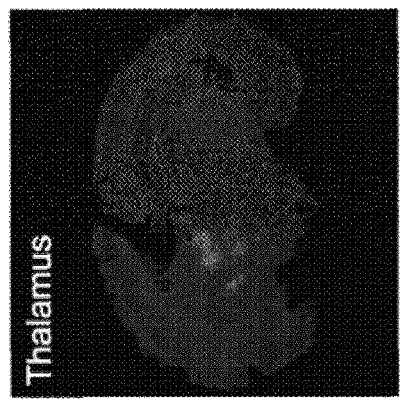
Figure 19B:
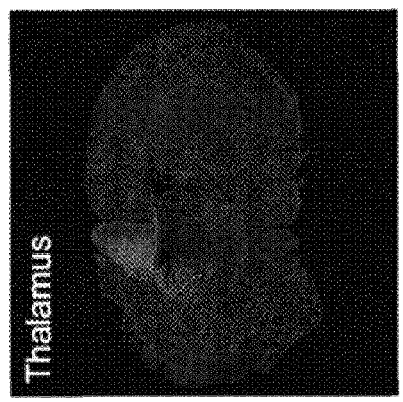
Figure 19A:
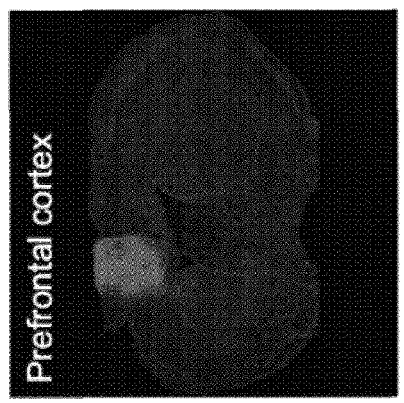
Figure 20C:
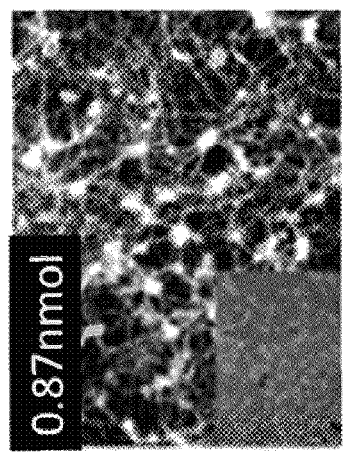
Figure 20B:
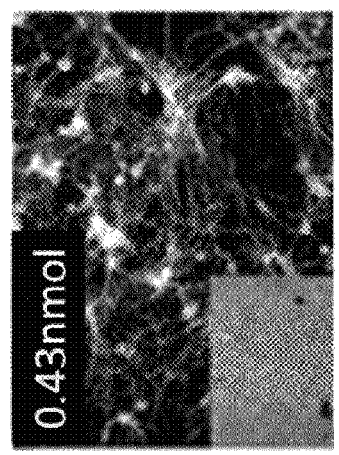
Figure 20A:
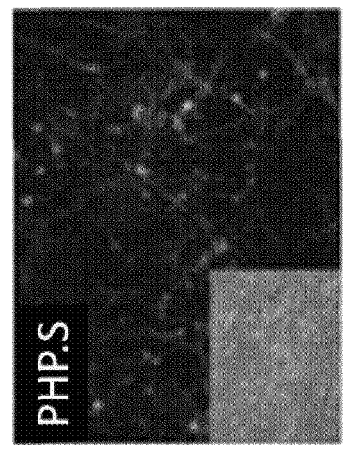
Figure 20F:
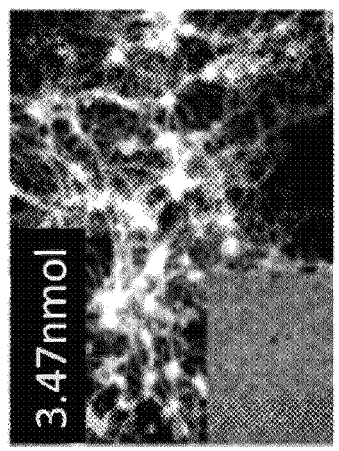
Figure 20E:
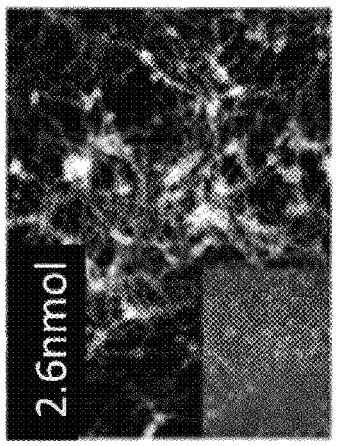
Figure 20D:
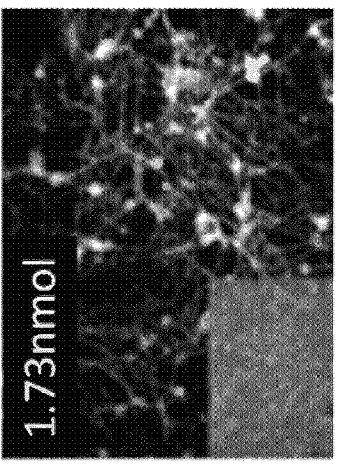

FIG. 19a-19c show retrograde transport of WGA::AAV2-• HSPG in mouse brain. 6E+8 VG of WGA::AAV2-• HSPG was injected into the prefrontal cortex of adult mice. Robust tdTomato fluorescence was observed at the injection site (FIG. 19a) and in the thalamus (FIGS. 19b-19c), indicating retrograde transport from terminals to cell bodies.

FIG. 20a-20f show boosting of PHP.S transduction efficiency in DRG using WGA-• HSPG-AAV at different virus:ligand ratios.

Figure 21:
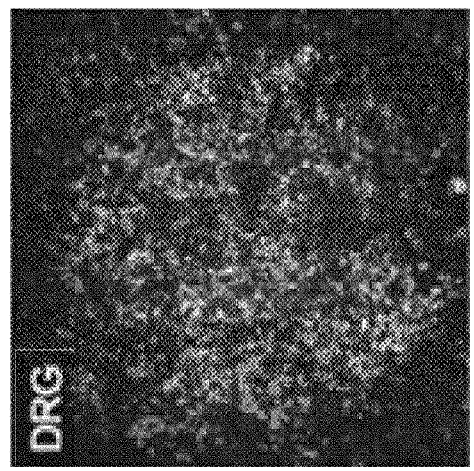

FIG. 21 shows the application of 1B4::AAV2-• HSPG to DRG neurons in culture. 1E+9 VG of IB4::AAV2-• HSPG was applied to DRG neurons in culture. Robust tdTomato fluorescence was observed in the majority of small sized neurons.

FIGS. 22a-22d show in vivo injection of IB4::AAV2-• HSPG in adult mouse. Injection of IB4::AAV2-• HSPG via subcutaneous, intranerve and intraspinal injections routes. (FIG. 22a) Vasculature labelling of IB4::AAV2-• HSPG following subcutaneous injection. (FIG. 22b) Whole mount DRG from a mouse injected with IB4::AAV2-• HSPG in the sciatic nerve. (FIG. 22c) Spinal cord section from a mouse injected with IB4::AAV2-• HSPG in the left sciatic nerve and stained with IB4-488. The overlap of signal in the ipsilateral side. (FIG. 22d) Labelled microglia from a mouse injected with IB4::AAV2-• HSPG in the spinal cord.

Figure 23:
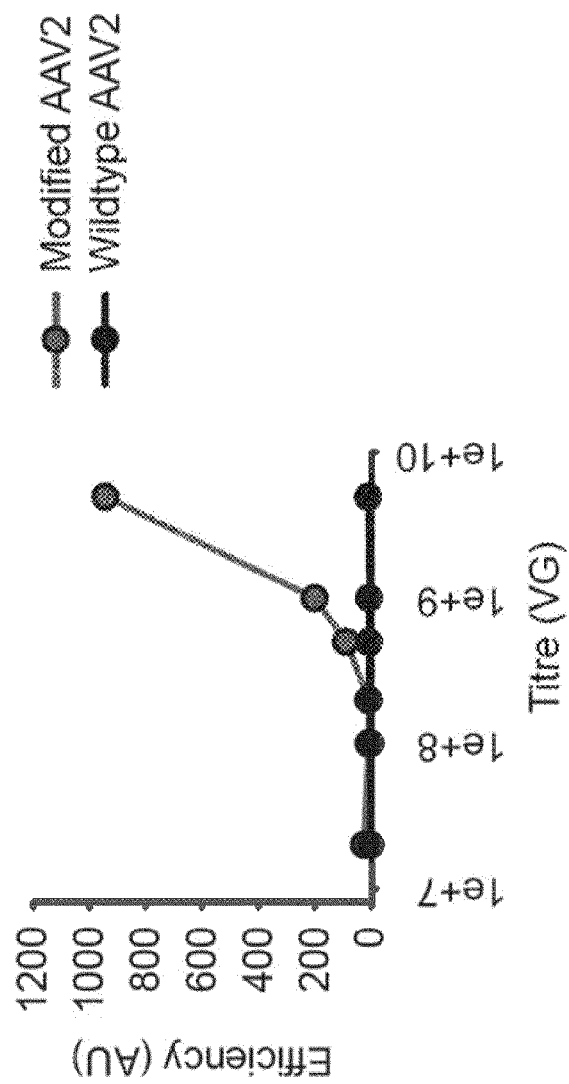
Figure 24C:
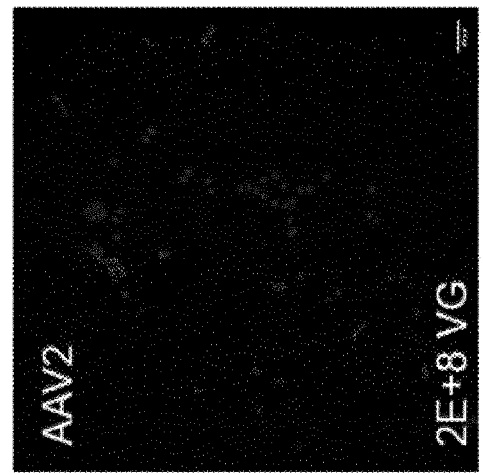
Figure 24B:
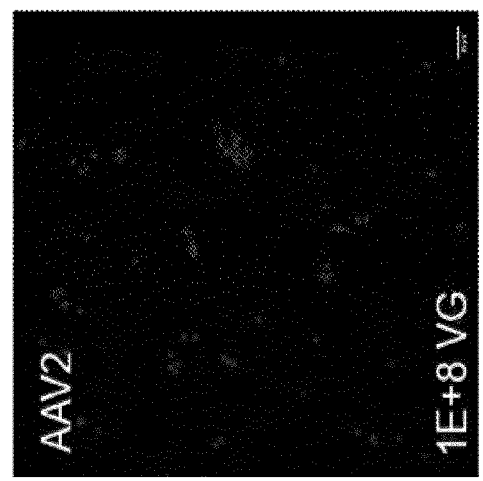
Figure 24A:
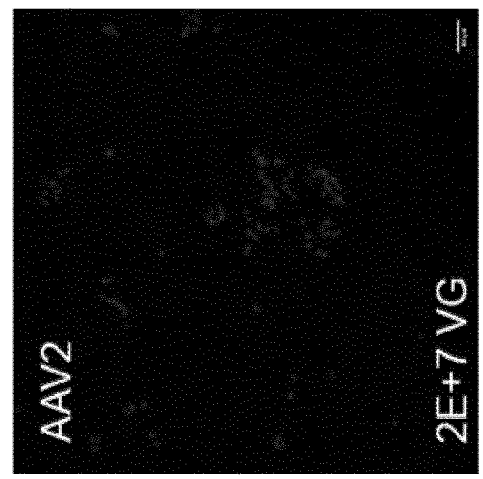
Figure 24F:
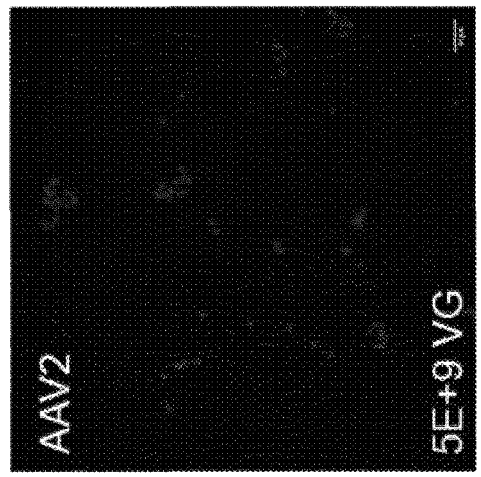
Figure 24E:
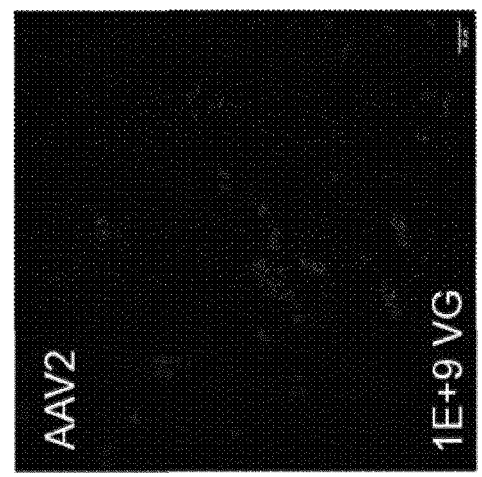
Figure 24D:
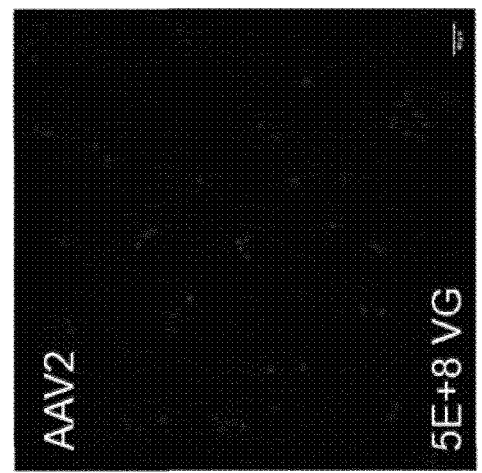
Figure 24I:
Figure 24H:
Figure 24G:
Figure 24L:
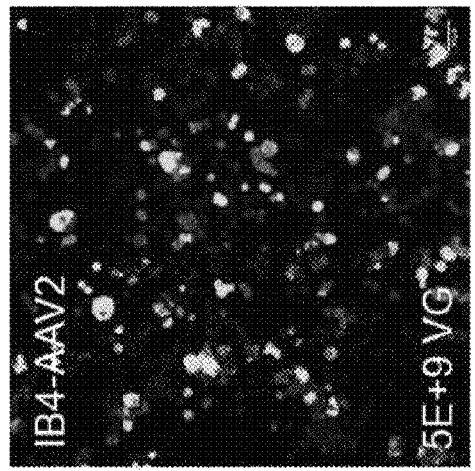
Figure 24K:
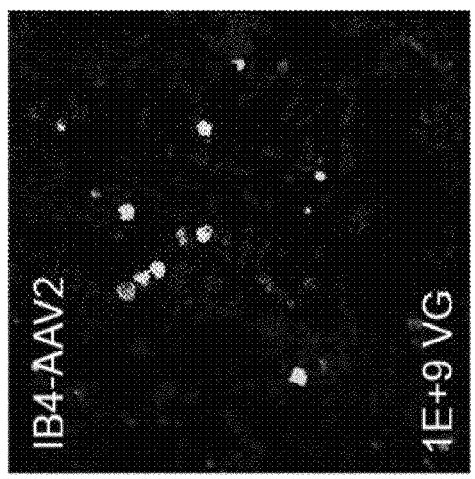
Figure 24J:
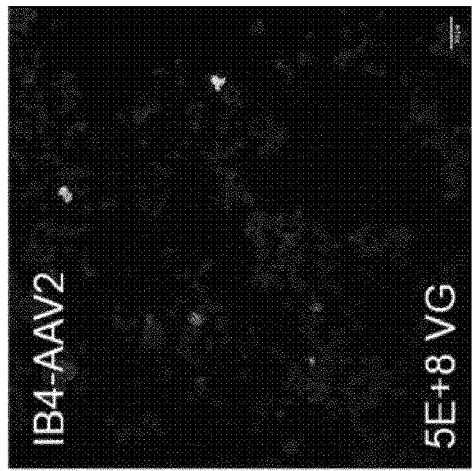

FIG. 23 shows a plot of transduction efficiency with increasing concentrations of wildtype AAV2 (corresponding to images in FIGS. 24a-24l) and IB4-AAV2 (corresponding images in FIGS. 24g-24l) applied to PC12 cells.

FIGS. 24a-24l show the GFP fluorescence of PC12 cells treated at each concentration of wildtype AAV2 (FIGS. 24a-24f) and IB4-AAV2 (FIGS. 24g-24l).

Figure 25:
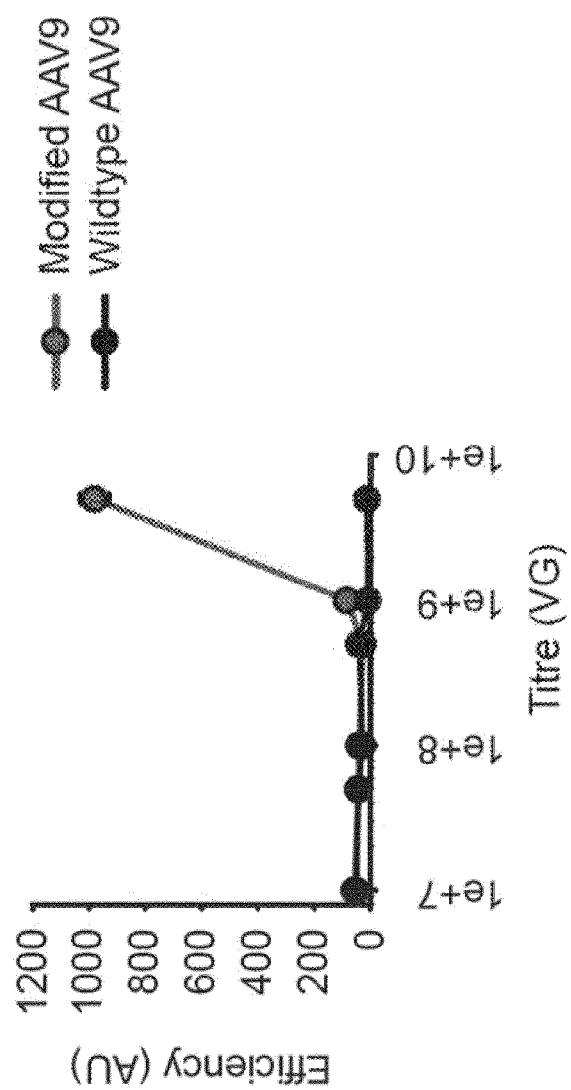
Figure 26C:
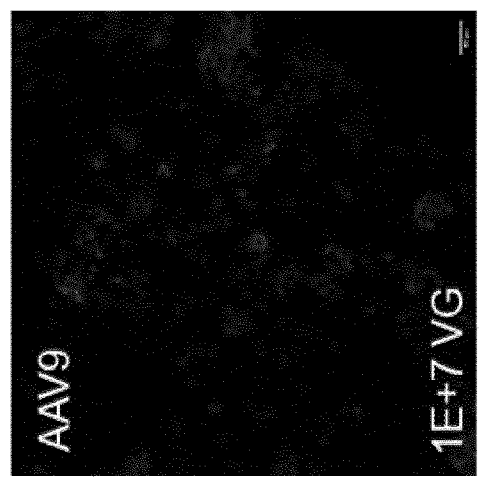
Figure 26B:
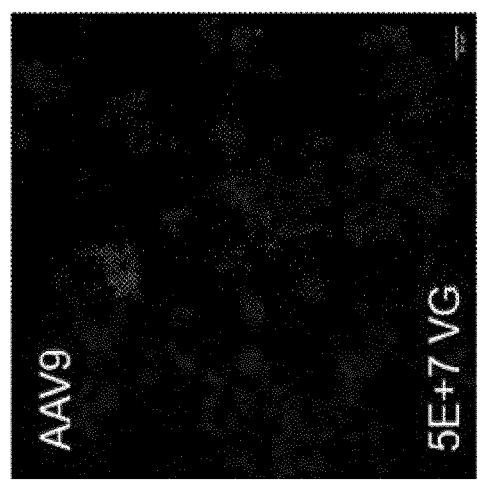
Figure 26A:
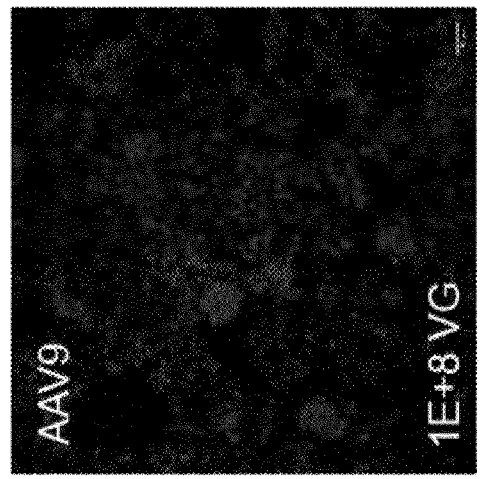
Figure 26F:
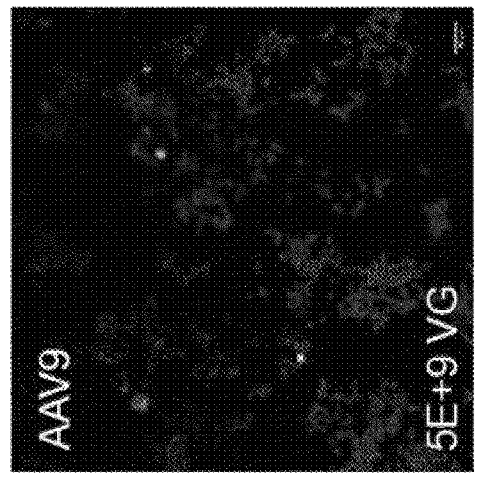
Figure 26E:
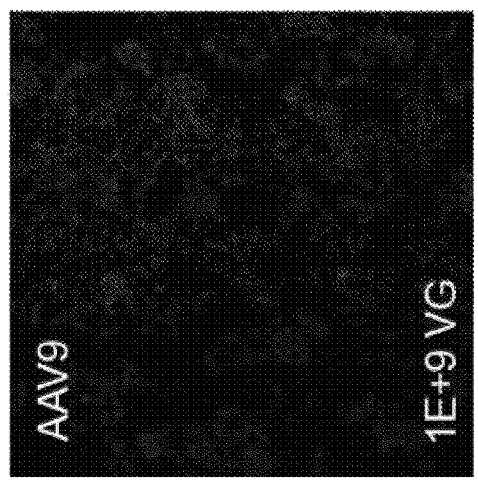
Figure 26D:
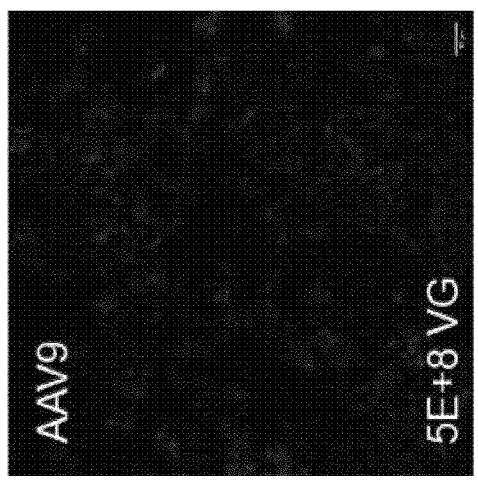
Figure 26I:
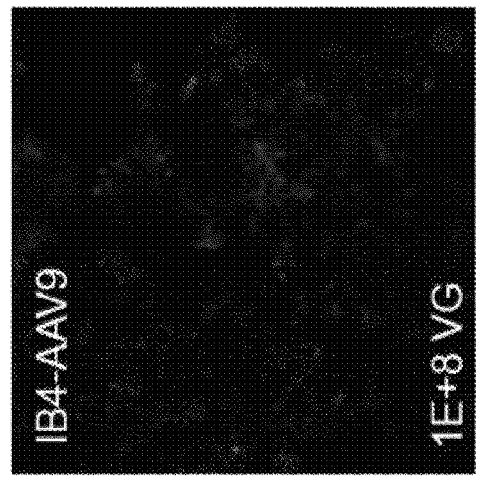
Figure 26H:
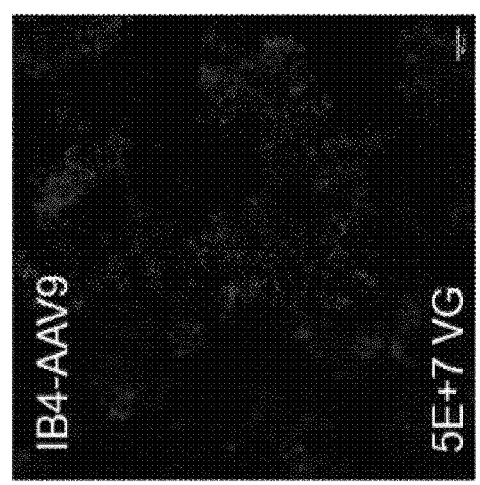
Figure 26G:
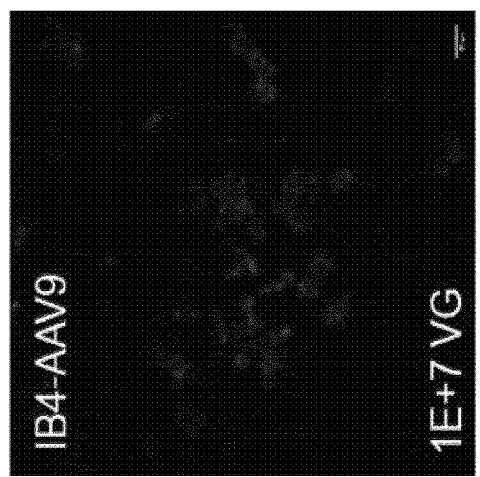
Figure 26I:
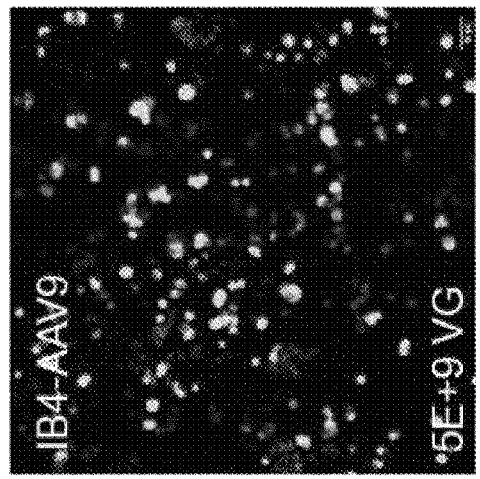
Figure 26K:
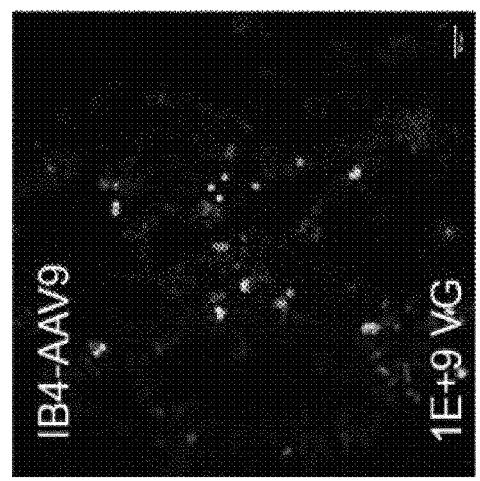
Figure 26J:
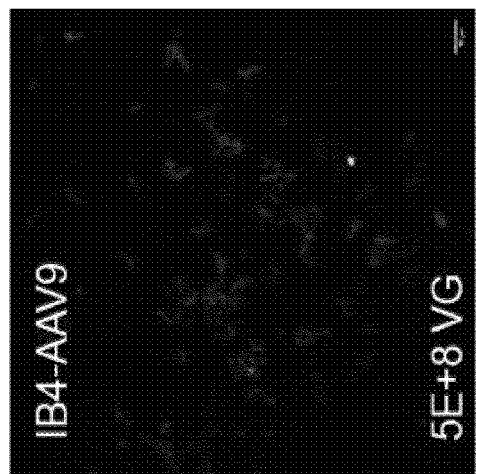
Figure 27D:
Figure 27C:
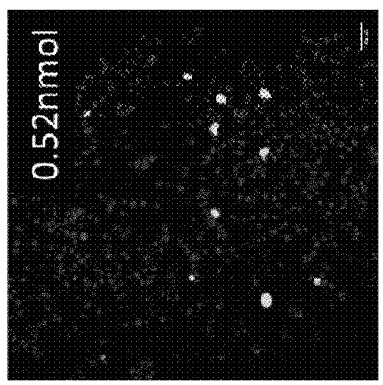
Figure 27B:
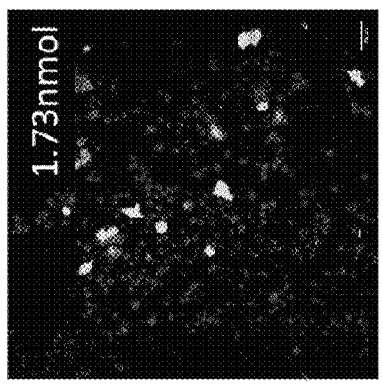
Figure 27A:
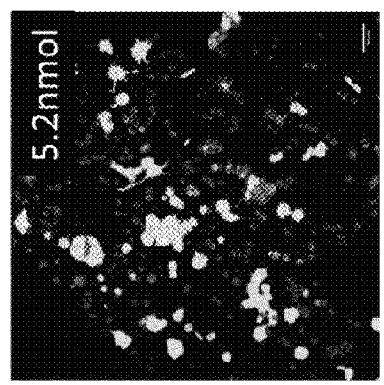
Figure 28D:
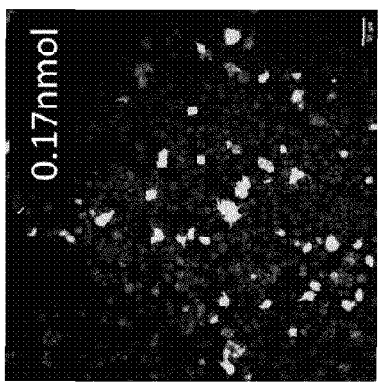
Figure 28C:
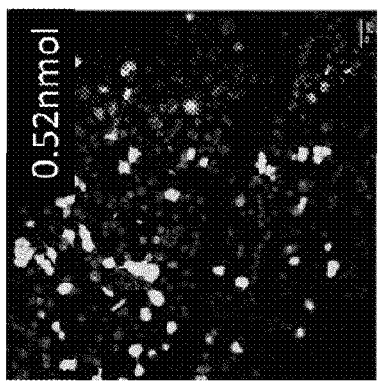
Figure 28B:
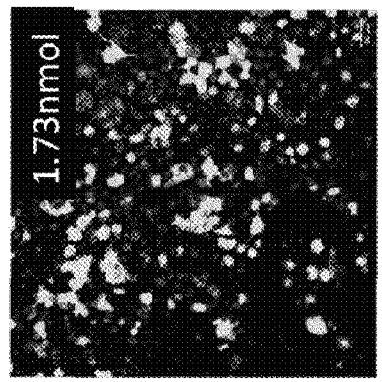
Figure 28A:
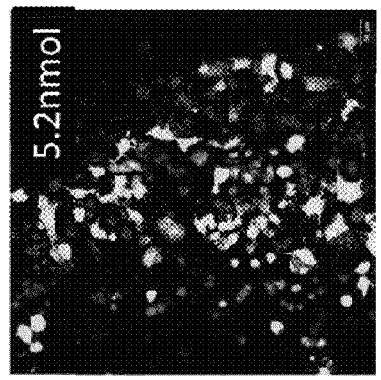
Figure 29A:
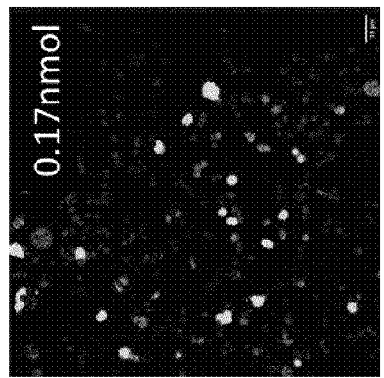
Figure 29B:
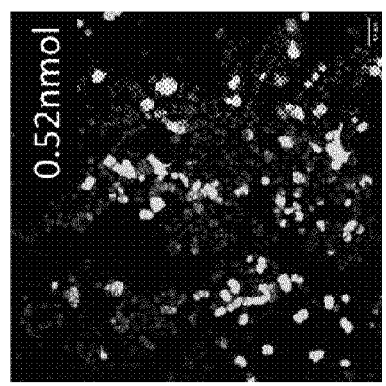
Figure 29C:
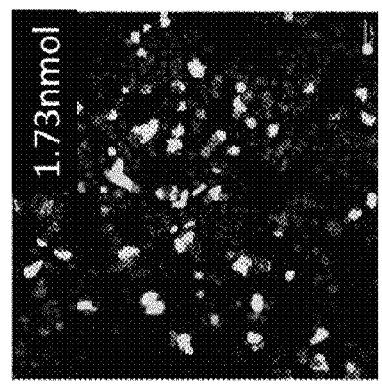
Figure 29D:
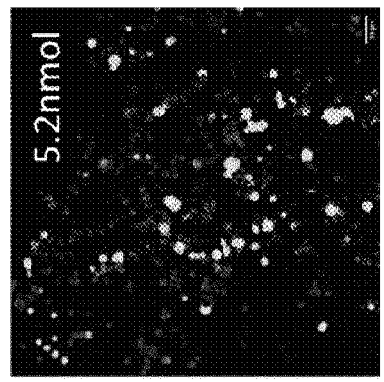
Figure 30D:
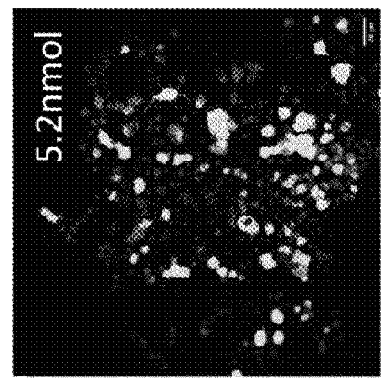
Figure 30C:
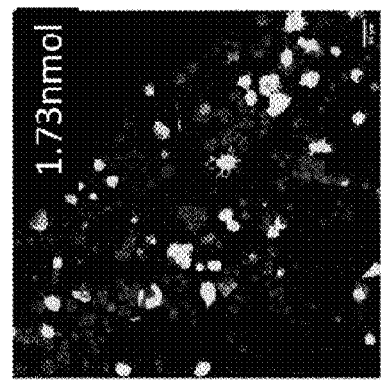
Figure 30B:
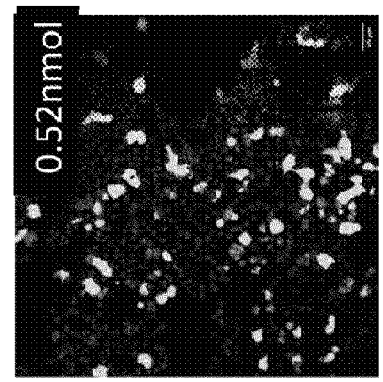
Figure 30A:
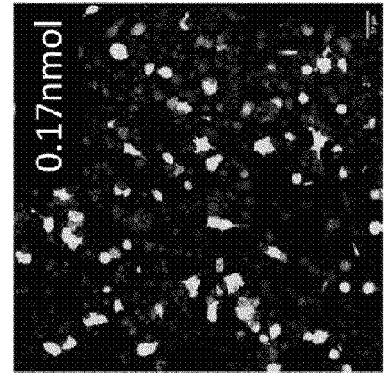

FIG. 25 shows a plot of transduction efficiency with increasing concentrations of wildtype AAV9 (corresponding to images in FIGS. 26a-26f) and IB4-AAV9 (corresponding images in FIGS. 26g-26l) applied to PC12 cells.

FIGS. 26a-26l show the GFP fluorescence of PC12 cells treated at each concentration of wildtype AAV9 (FIGS. 26a-26f) or IB4-AAV9 (FIGS. 26g-26l).

FIGS. 27a-27d show representative GFP fluorescence images for IB4 conjugated to • HSPG-AAV2 at increasing molar ratios with no spacer and applied to PC12 cells.

FIGS. 28a-28d show representative images are for IB4: • HSPG-AAV2 constructs prepared at increasing amounts of reactive linker with Short n=3 PEG spacer and applied to PC12 cells.

FIGS. 29a-29d show representative images for IB4: • HSPG-AAV2 constructs prepared at increasing amounts of capsid reactive linker with Medium n=8 PEG spacer and applied to PC12 cells.

FIGS. 30a-30d show representative images for IB4: • HSPG-AAV2 constructs prepared at increasing amounts of capsid reactive linker with Long PEG=16 spacer and applied to PC12 cells.

Figure 31:
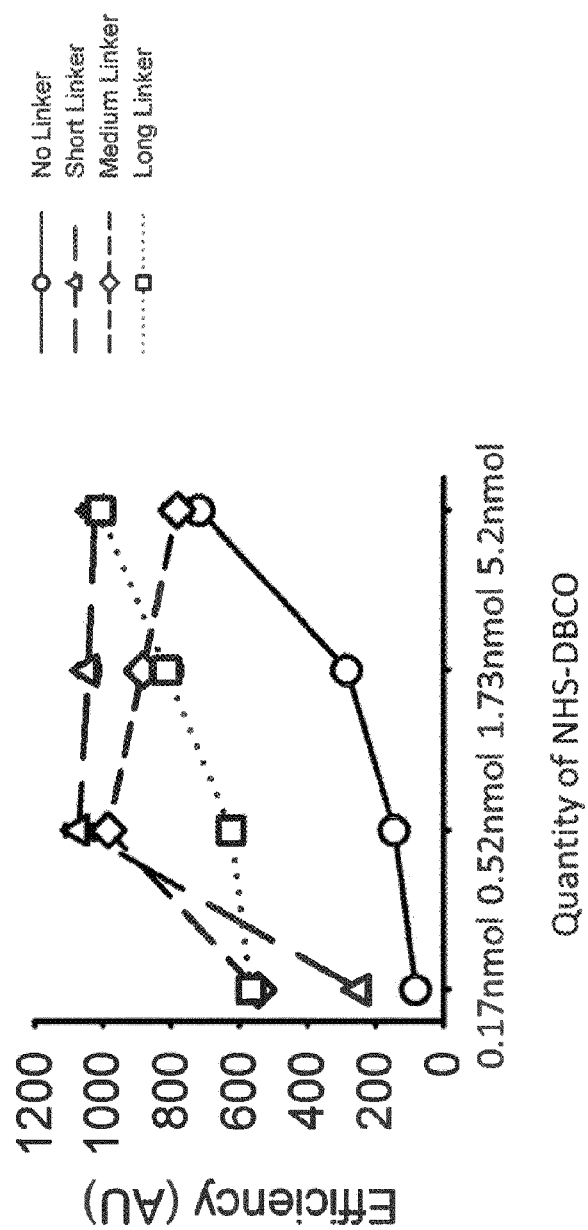

FIG. 31 shows quantification of average GFP fluorescent intensity in each cell for at increasing ligand to virus molar ratios with different linker lengths (n=3, mean+/−SEM).

Figure 32O:
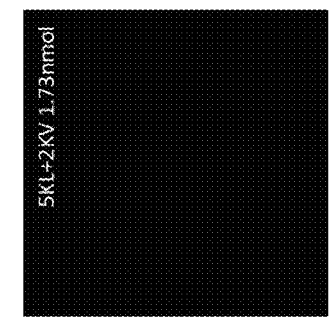
Figure 32N:
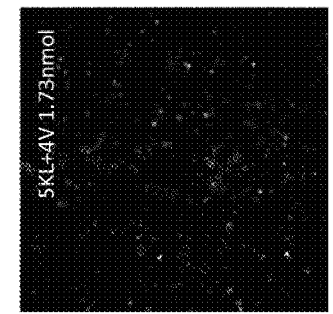
Figure 32M:
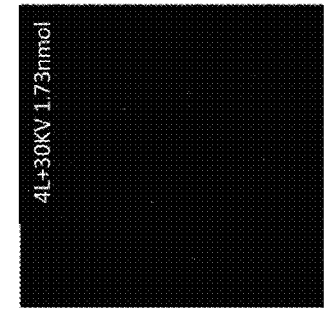
Figure 32L:
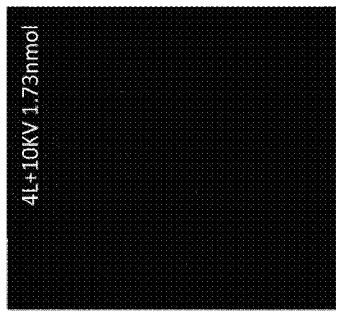
Figure 32K:
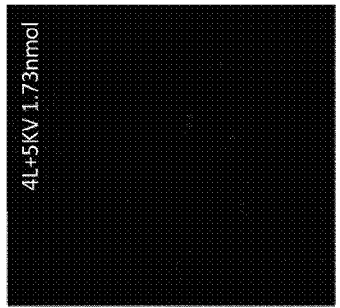
Figure 32S:
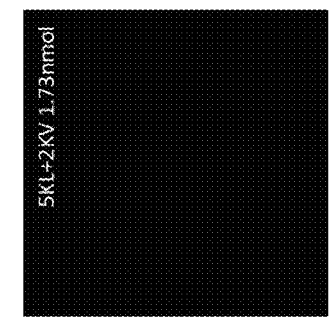
Figure 32R:
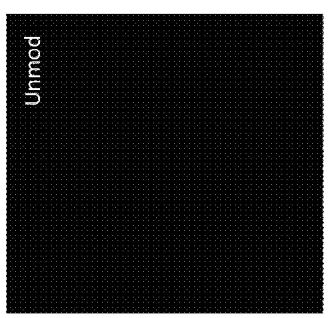
Figure 32Q:
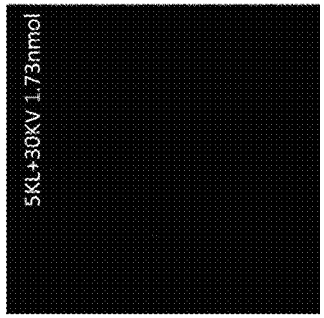
Figure 32P:
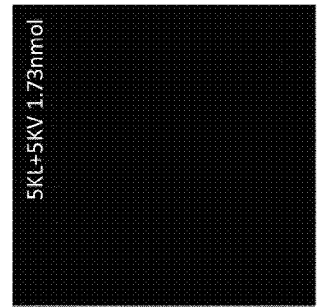

FIGS. 32a-32s show the GFP fluorescence images corresponding to transduction efficiency in PC12 cells of an WGA:AAV2ΔHSPG virus construct comprising linkers with different spacer lengths, i.e., (n) of PEGn (units of ethylene glycol) on the virus side (V) and the WGA ligand side (L), with virus being functionalized with various molar amounts of linker.

Figure 33:
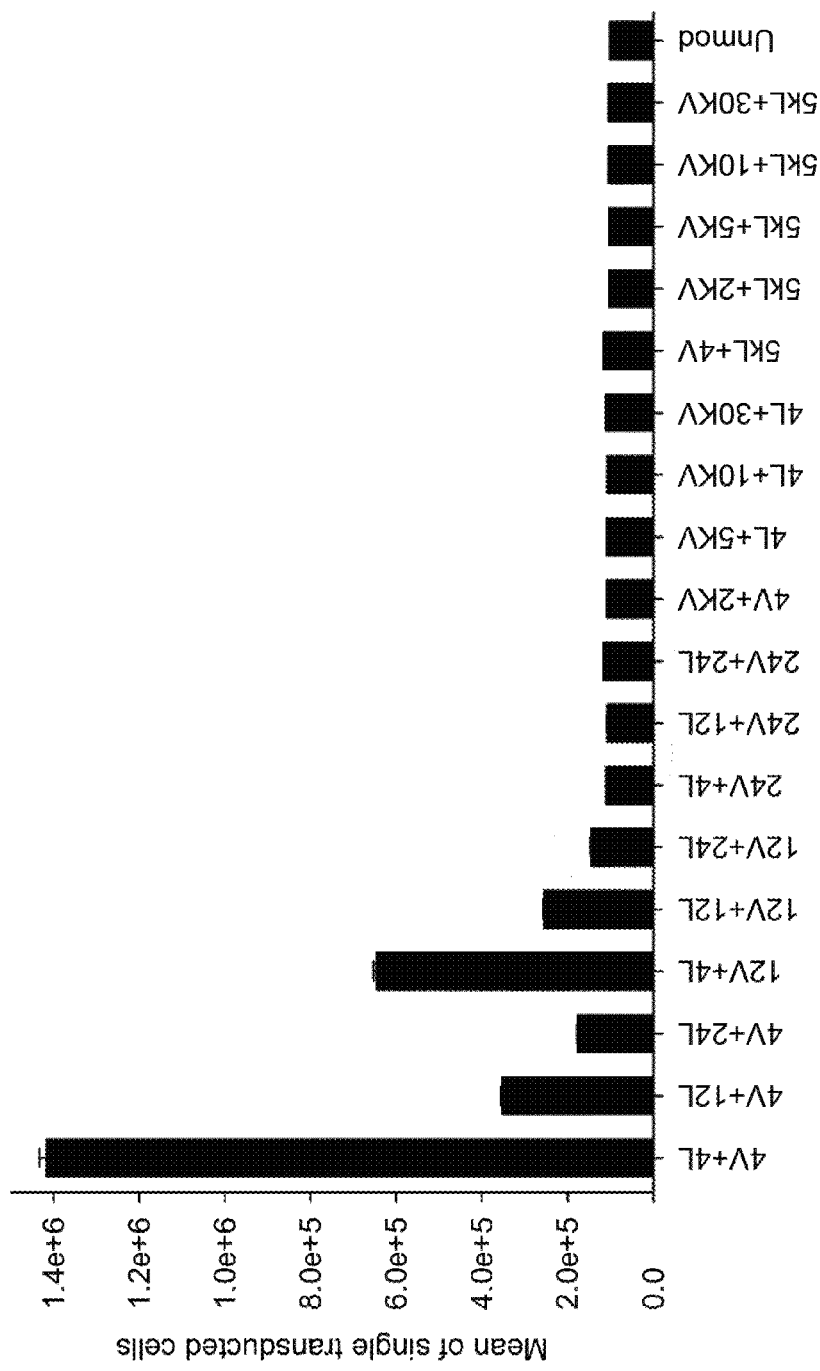

FIG. 33 shows a chart of the mean GFP fluorescence intensity of PC12 cells transduced with AAV2ΔHSPG virus modified with WGA having different linker spacers. The data plotted corresponds to the mean transduction efficiency.

Figure 34:
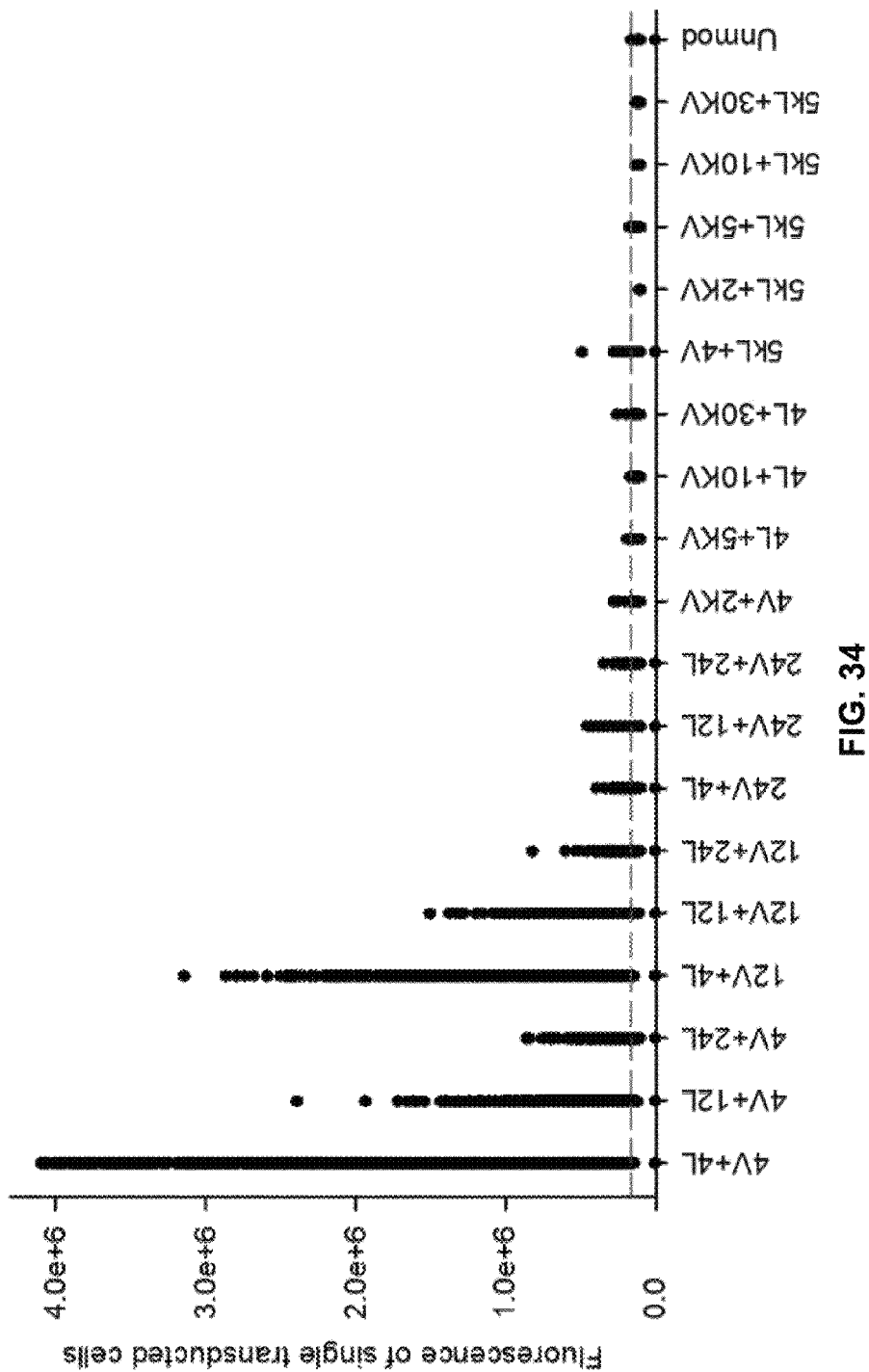

FIG. 34 shows a chart of the individual cell transduction efficiency of PC12 cells treated with AAV2ΔHSPG virus constructs surface modified with WGA having different linker spacers compared to unmodified virus (red dotted line).

Figure 35:
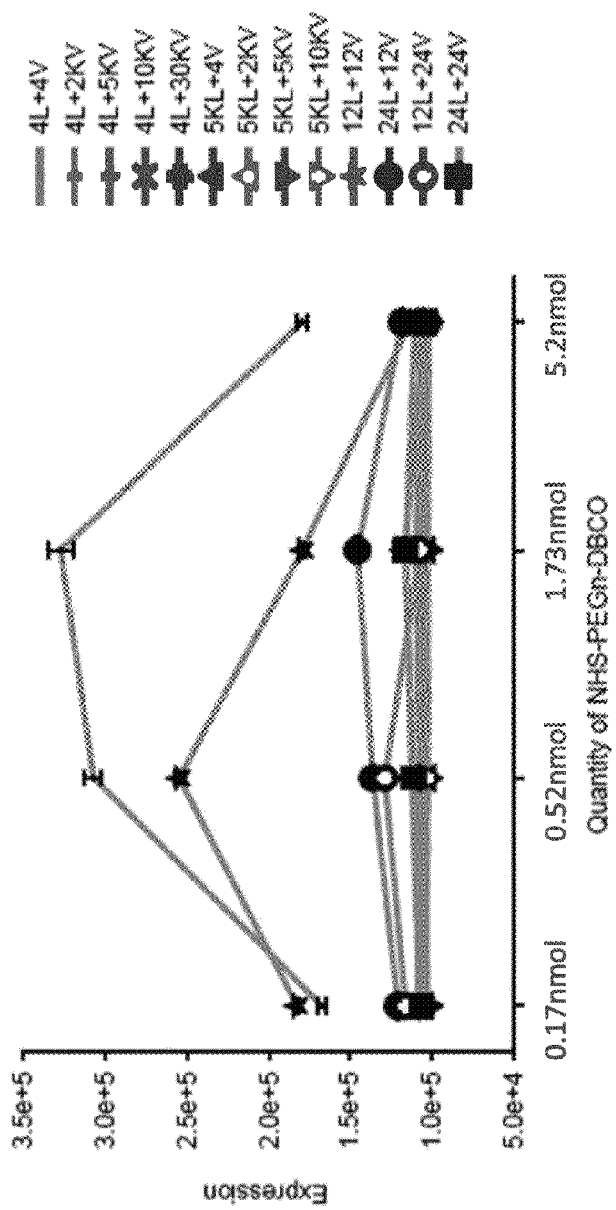

FIG. 35 shows the mean transduction efficiency of the of PC12 cells treated with AAV2ΔHSPG virus constructs surface modified with WGA having different linker spacers compared to unmodified virus.

Figure 36:
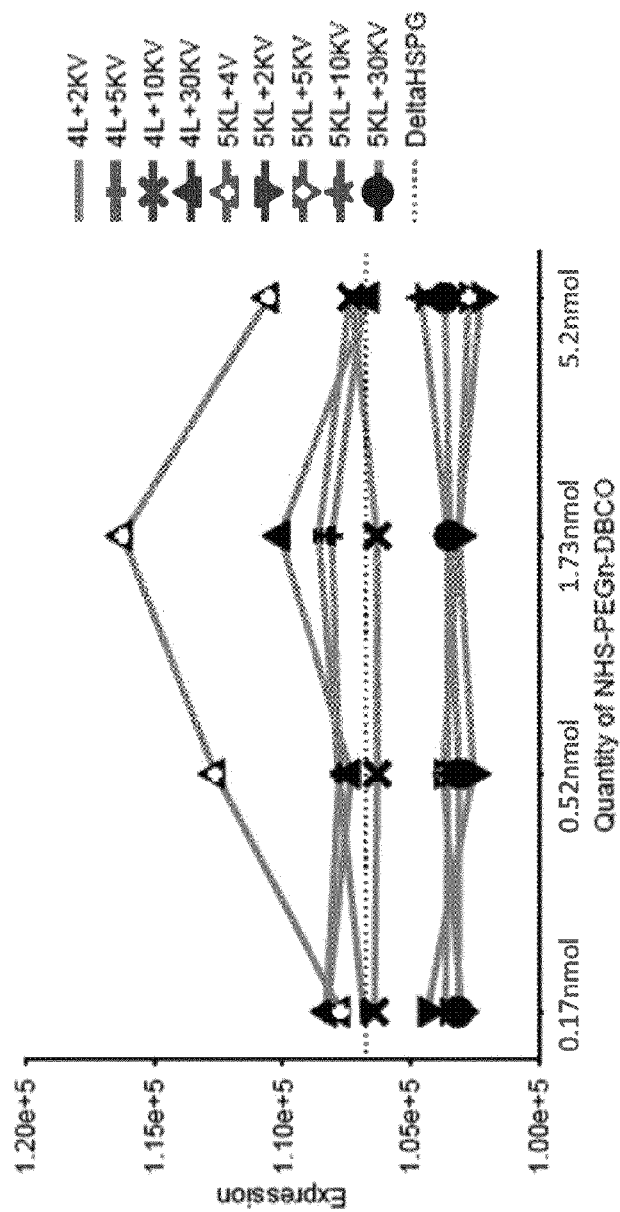

FIG. 36 shows quantification of expression displaying only the worse performing discrete and dispersed PEG combinations.

FIGS. 37a-37d show tdTomato fluorescence images in PC12cells treated with the AAV2• HSPG-WGA constructs prepared using TCO/Tetrazine ligation with virus being functionalized with various molar amounts of linker. FIG. 37e shows unmodified virus; FIG. 37f show tdTomato fluorescence images in PC12cells treated with the AAV2• HSPG-WGA prepared using DBCO/Azide crosslinker reactive pairs at a 3E+9 VG: 1.73 nmol virus:linker ratio.

Figure 38:
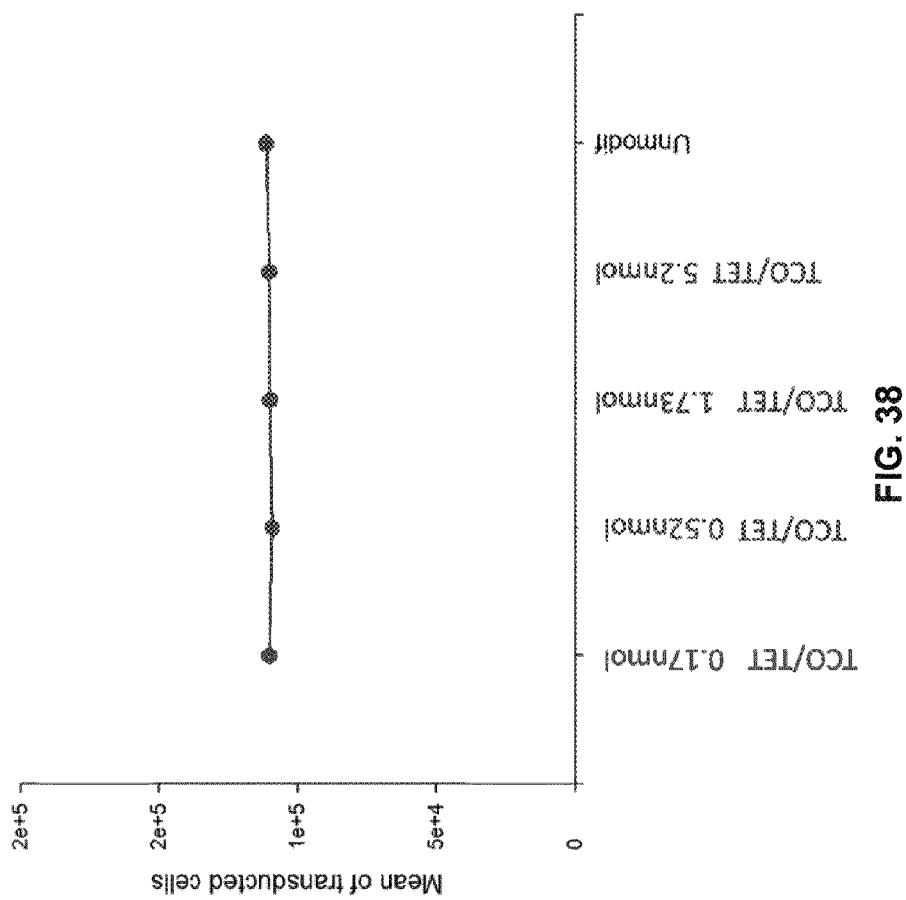
Figure 39:
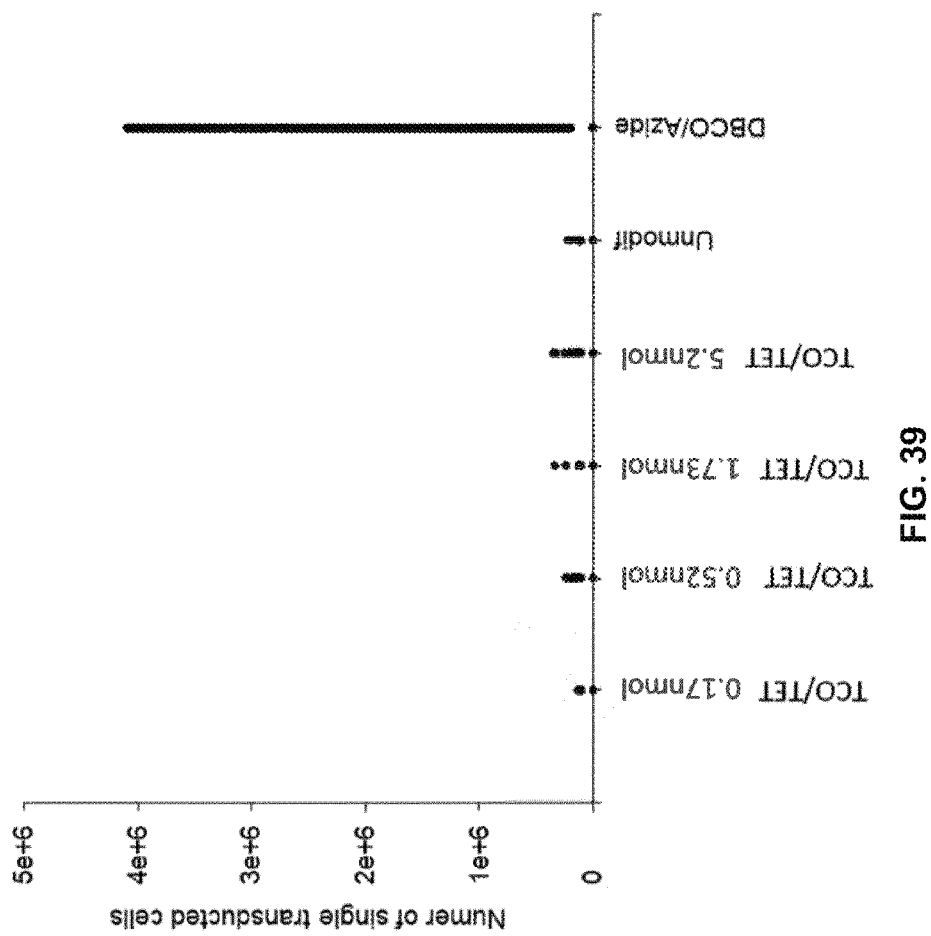

FIGS. 38 and 39 show quantification of the tdTomato fluorescence images to provide the mean transduction efficiency and individual cell transduction efficiency, respectively, in PC12cells treated with the AAV2• HSPG-WGA constructs prepared using TCO/Tetrazine ligation at different virus to linker ratios, compared to that obtained for the AAV2• HSPG-WGA prepared using DBCO/Azide at a 3E+9 VG: 1.73 nmol virus:linker ratio.

FIGS. 40a-40d show tdTomato fluorescence images in PC12cells treated with the AAV2• HSPG-WGA constructs prepared using Phosphine-NHS/Azide ligation at different ratios virus to linker ratios. FIG. 40e shows unmodified virus; FIG. 40f show tdTomato fluorescence images in PC12cells treated with the AAV• HSPG-WGA prepared using DBCO/Azide crosslinker reactive pairs at a 3E+9 VG: 1.73 nmol virus:linker ratio.

Figure 41:
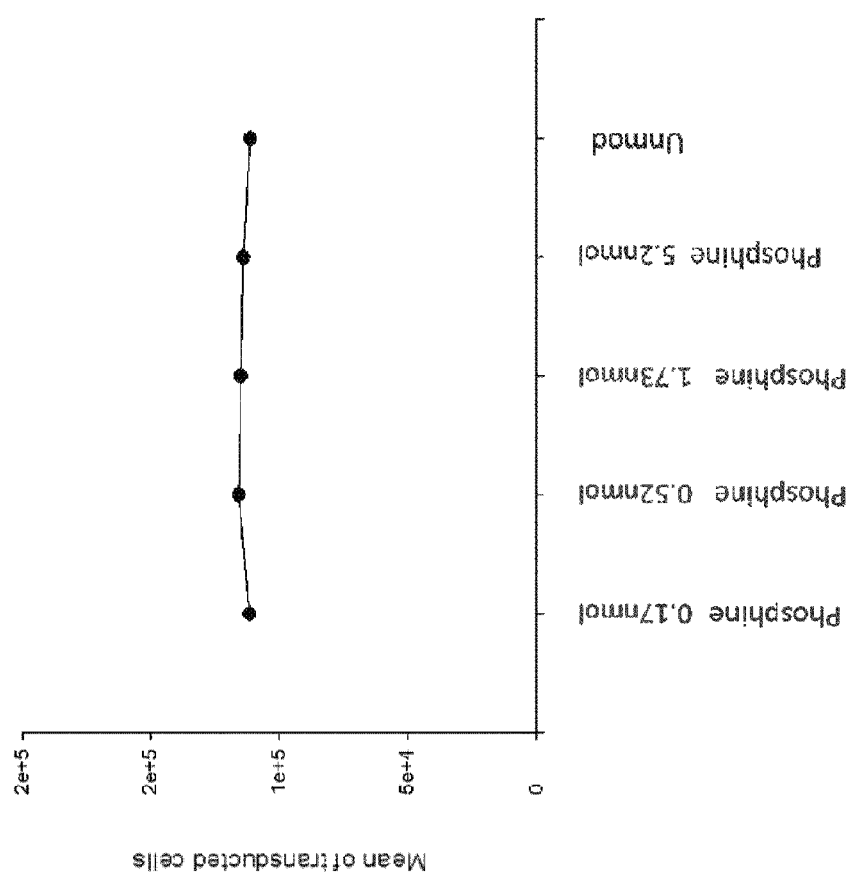
Figure 42:
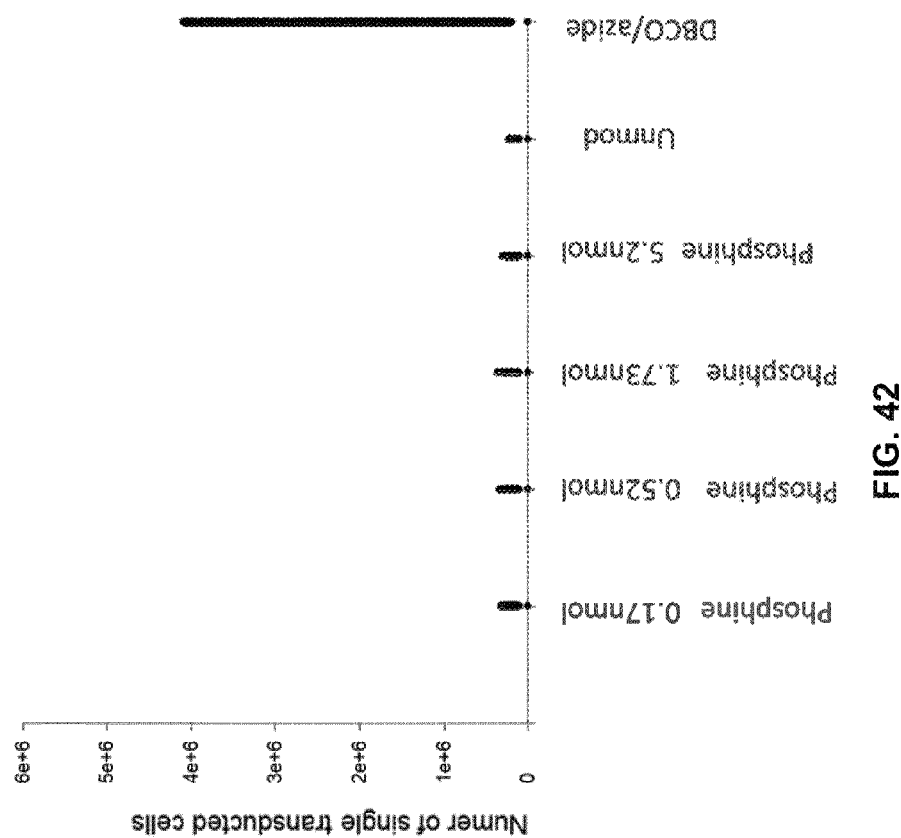

FIGS. 41 and 42 show quantification of the tdTomato fluorescence images to provide the mean transduction efficiency and individual cell transduction efficiency, respectively, in PC12cells treated with the AAV2• HSPG-WGA constructs prepared using Phosphine-NHS/Azide ligation at different virus to linker ratios, compared to that obtained for the AAV2• HSPG-WGA prepared using DBCO/Azide crosslinker reactive pairs at a 3E+9 VG: 1.73 nmol virus:linker ratio.

Figure 43:
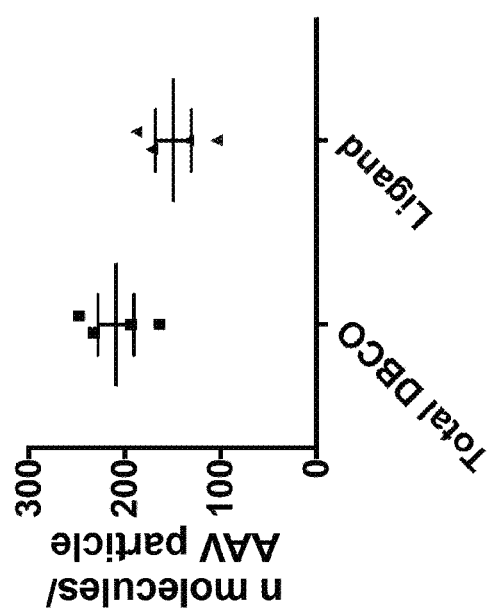

FIG. 43 illustrates the number of PEG4-DBCO molecules per AAV9 and the number of WGA-PEG4-Azide molecules per AAV9 at optimal transduction efficiencies.

Figure 44:
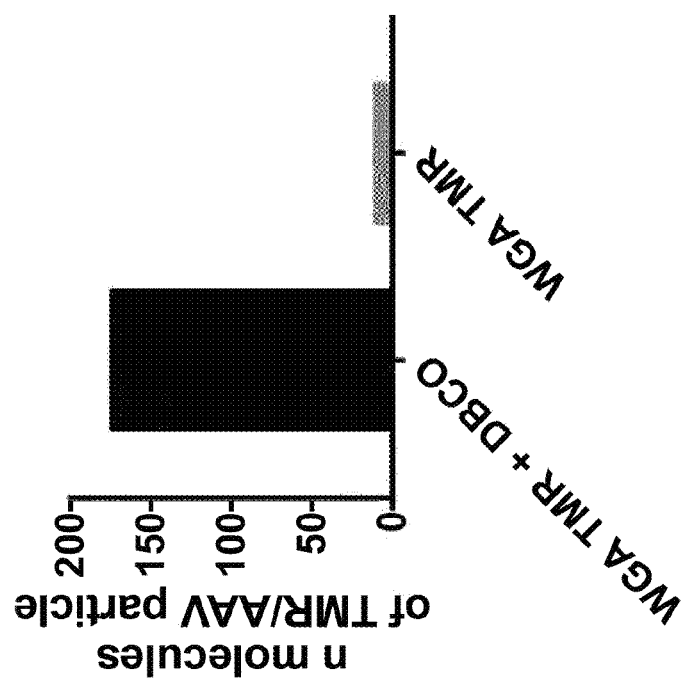

FIG. 44 illustrates the number of ligands per AAV particle for the AAV9-PEG4-DBCO::WGA-SNAP-TMR-PEG4-Azide construct and with the control AAV9 incubated only with WGA-SNAP-TMR-PEG4-Azide without first being functionalized by the DBCO-PEG-NHS linker.

FIGS. 45a-45e illustrate GFP or RFP fluorescence in PC12 cells treated with unmodified wild type AAV3 (FIG. 45a) and WGA-AAV3 (FIGS. 45b-45e) that were prepared at various virus:linker ratios.

Figure 46:
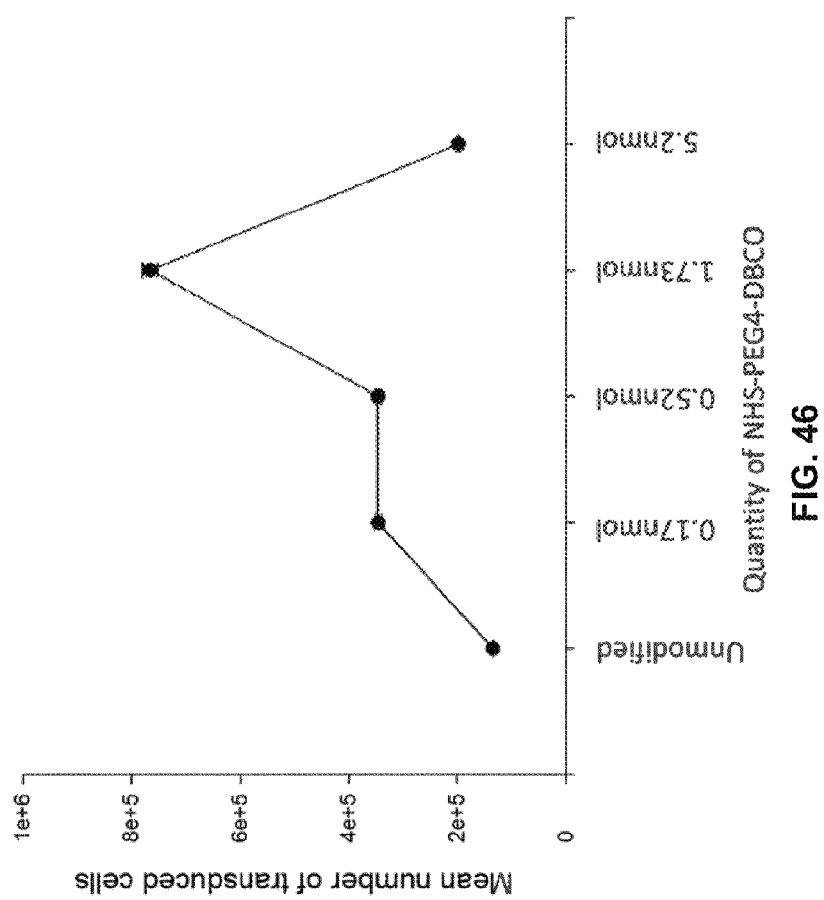
Figure 47:
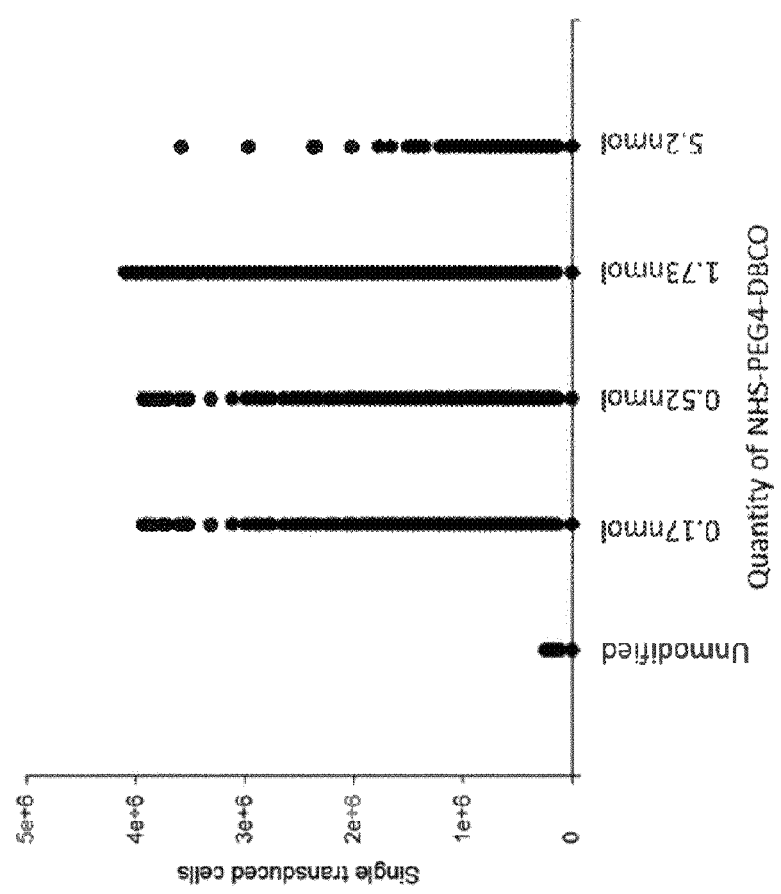
Figure 48A:
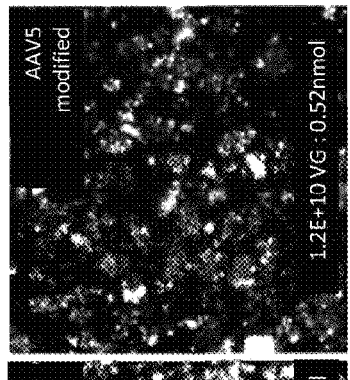
Figure 48B:
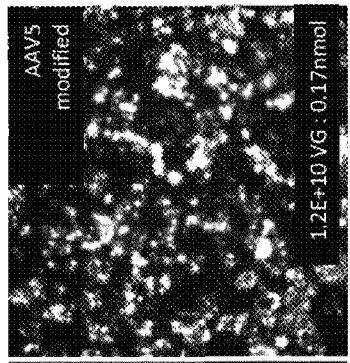
Figure 48C:
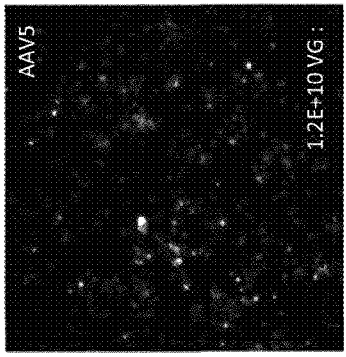
Figure 48D:
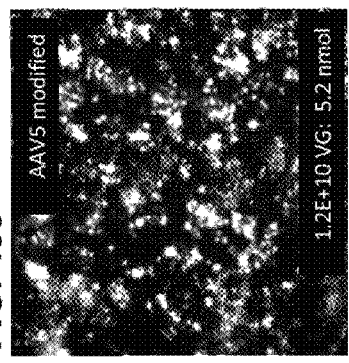
Figure 48E:
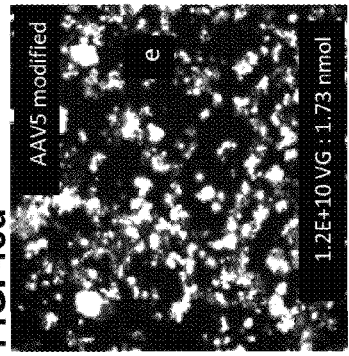

FIGS. 46 and 47 show quantification of the fluorescence images to provide the mean transduction efficiency and individual cell transduction efficiency, respectively, in PC12cells treated with the AAV3 HSPG-WGA constructs prepared.

FIGS. 48a-48e illustrate GFP or RFP fluorescence in PC12 cells treated with unmodified wild type AAV5 (FIG. 48a) and WGA-AAV3 (FIGS. 48b-48e) that were prepared at various virus:linker ratios.

Figure 49:
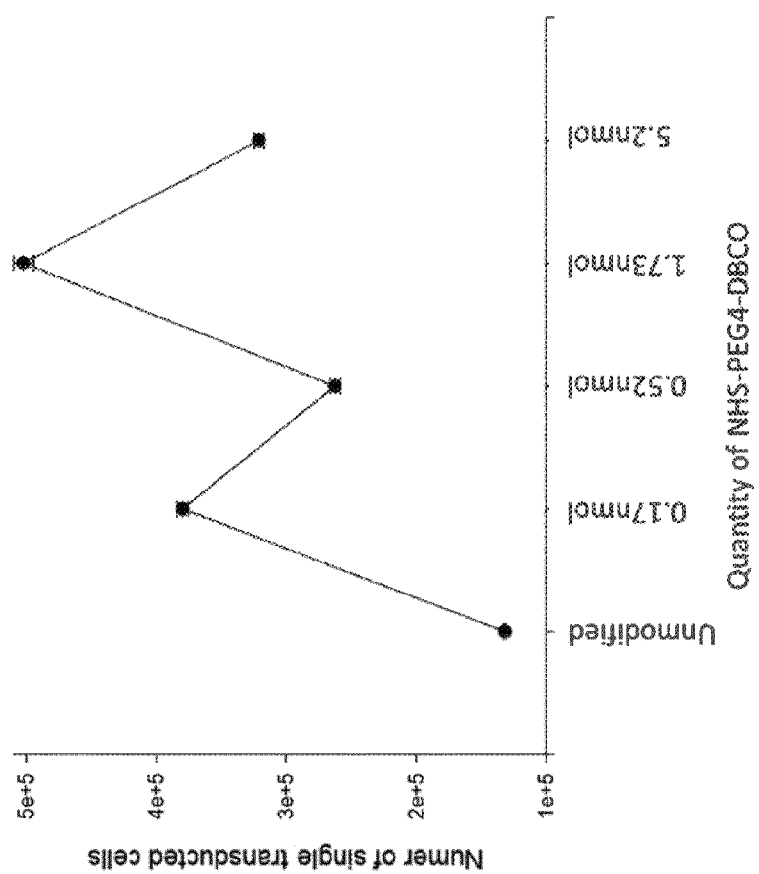
Figure 50:
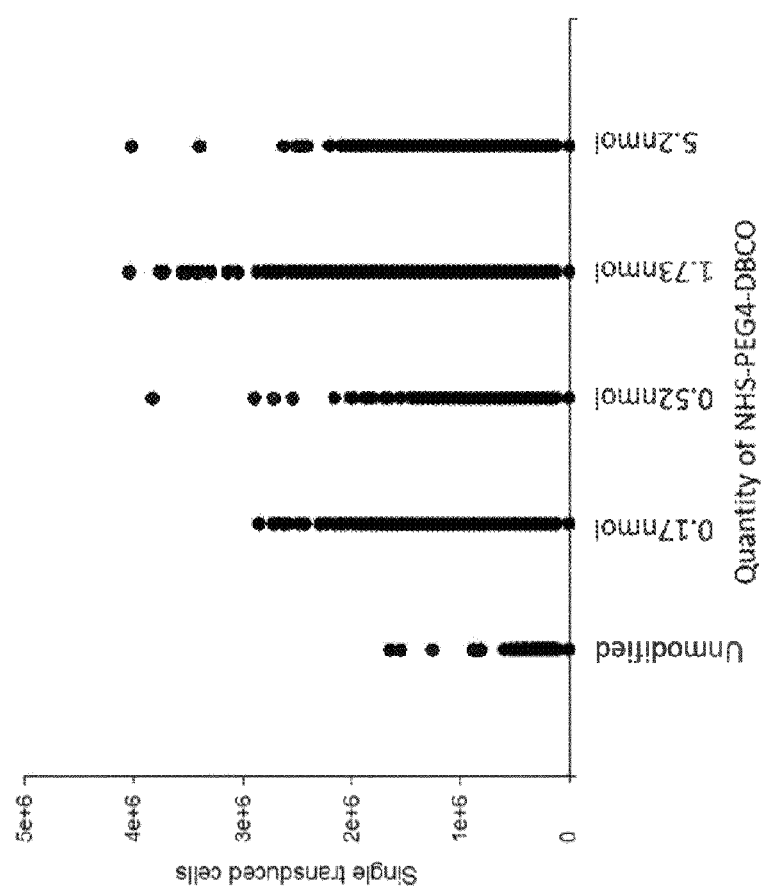

FIGS. 49 and 50 show quantification of the fluorescence images to provide the mean transduction efficiency and individual cell transduction efficiency, respectively, in PC12cells treated with the AAV6 HSPG-WGA constructs prepared as in FIG. 48.

FIGS. 51a-e illustrate GFP or RFP fluorescence in PC12 cells treated with unmodified wild type AAV6 (FIG. 51a) and WGA-AAV6 (FIGS. 51b-51e) that were prepared at various virus:linker ratios.

Figure 52:
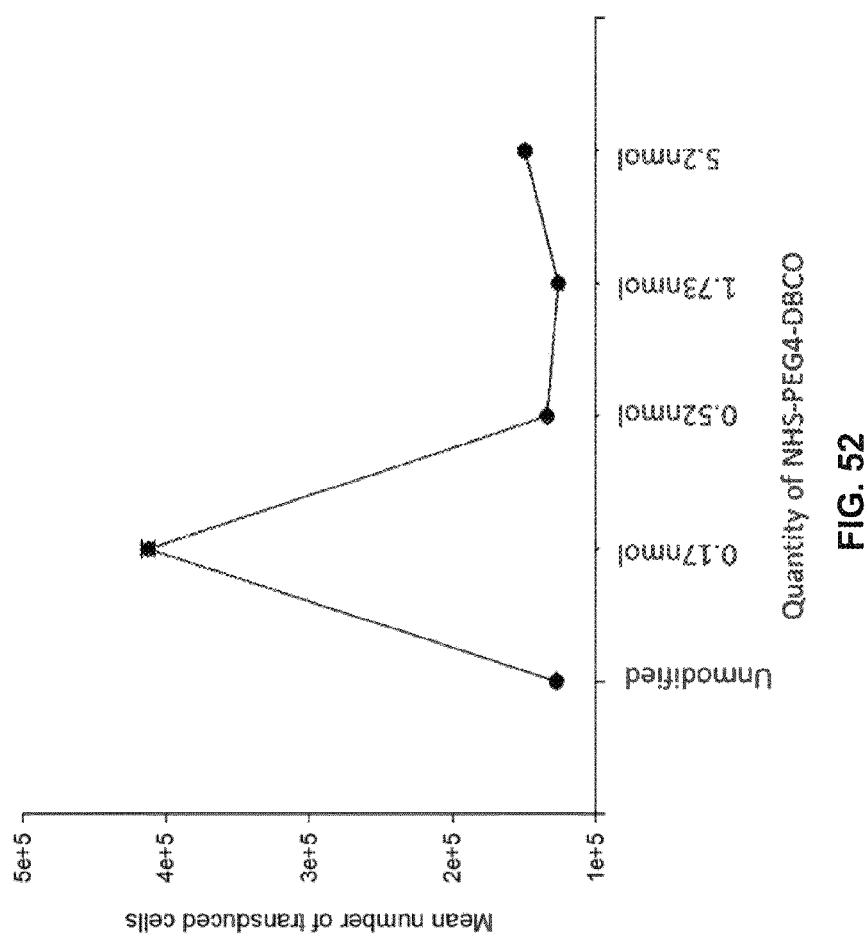
Figure 53:
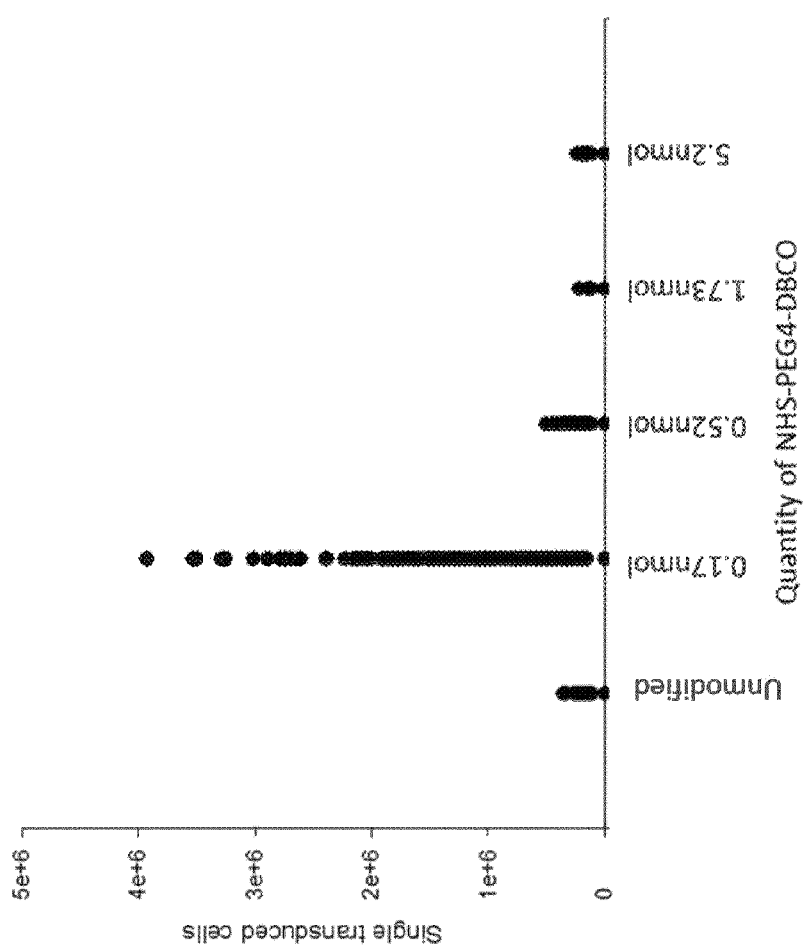

FIGS. 52 and 53 show quantification of the tdTomato fluorescence images to provide the mean transduction efficiency and individual cell transduction efficiency, respectively, in PC12cells treated with the WGA-AAV6 constructs prepared as in FIG. 51.

FIGS. 54a-54e illustrate GFP or RFP fluorescence in PC12 cells treated with unmodified wild type AAV8 (FIG. 54a) and WGA-AAV8 (FIGS. 54b-54e) that were prepared at various virus:linker ratios.

Figure 55:
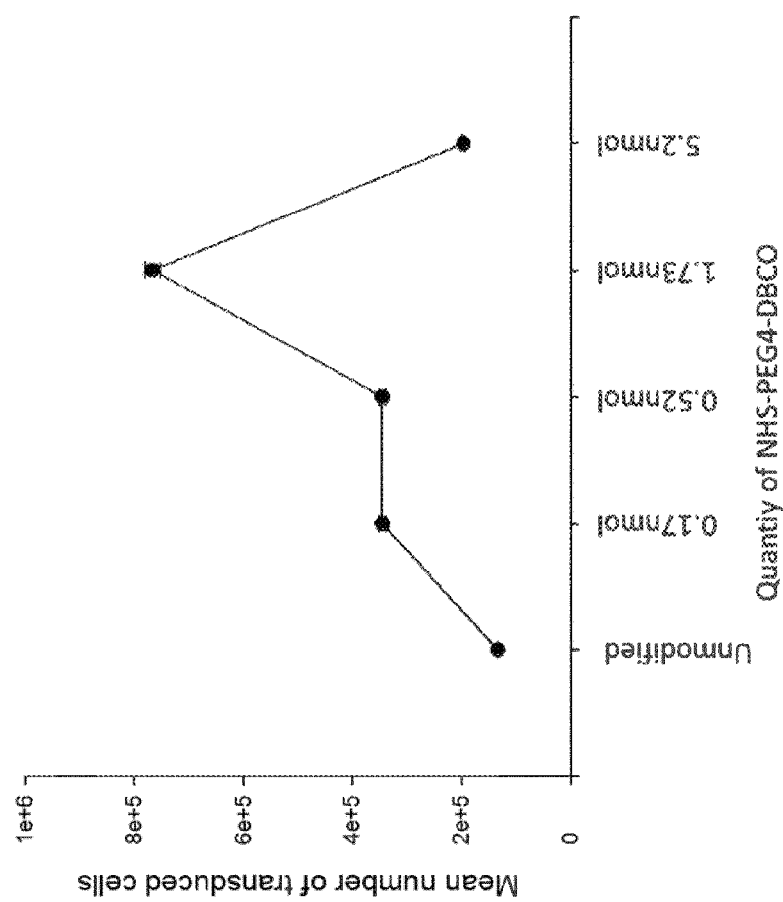
Figure 56:
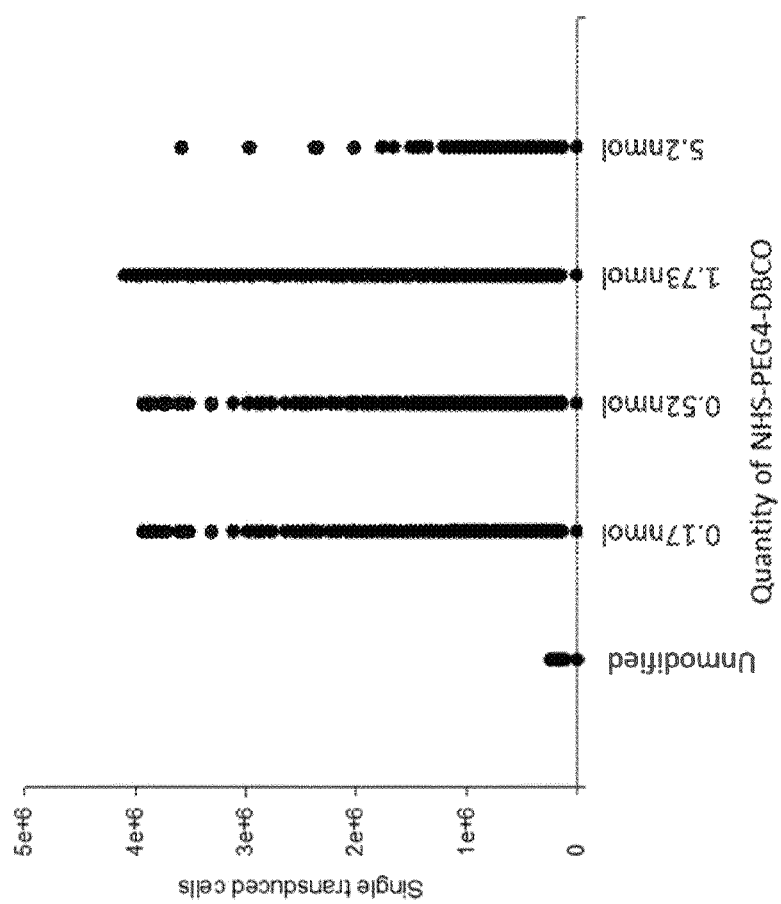

FIGS. 55 and 56 show quantification of the fluorescence images to provide the mean transduction efficiency and individual cell transduction efficiency, respectively, in PC12cells treated with the WGA-AAV8 constructs prepared as in FIG. 54.

Figure 57:
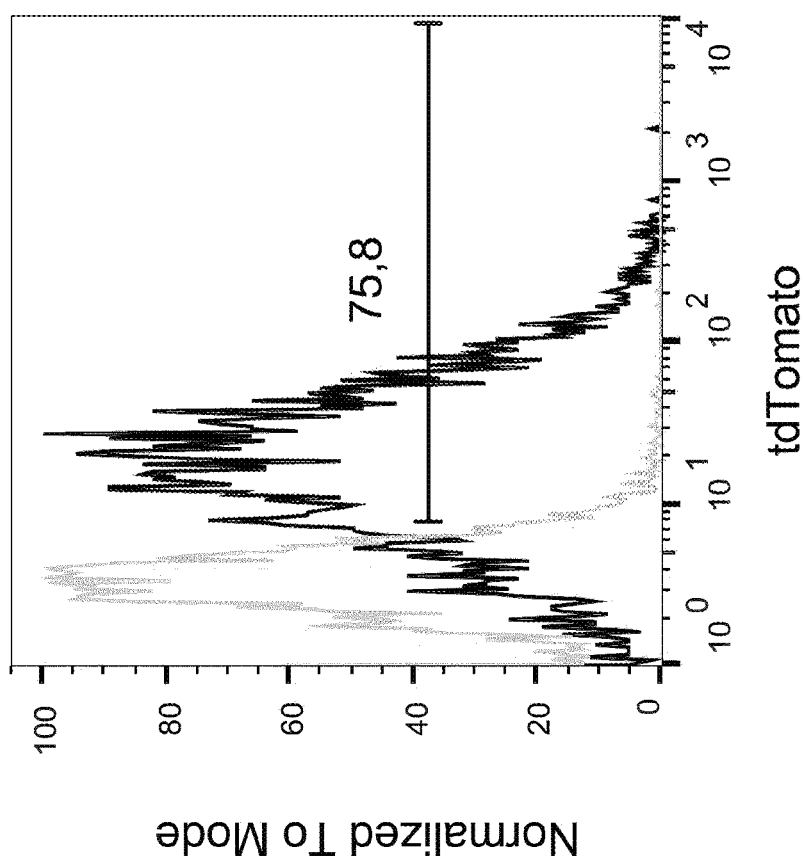

FIG. 57 illustrates the transduction of HEK293 cells by AAV2 as analyzed by FACS (untransduced, grey and transduced cells black).

Figure 58B:
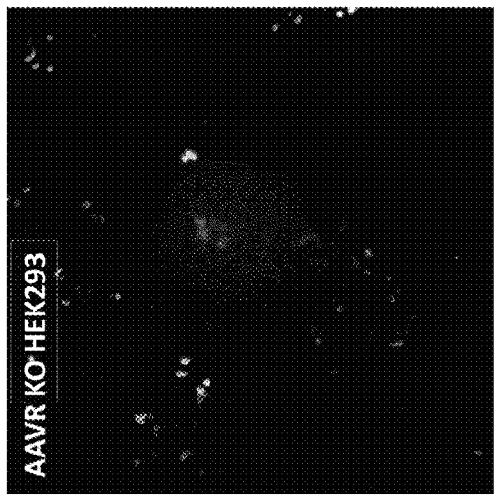
Figure 58A:
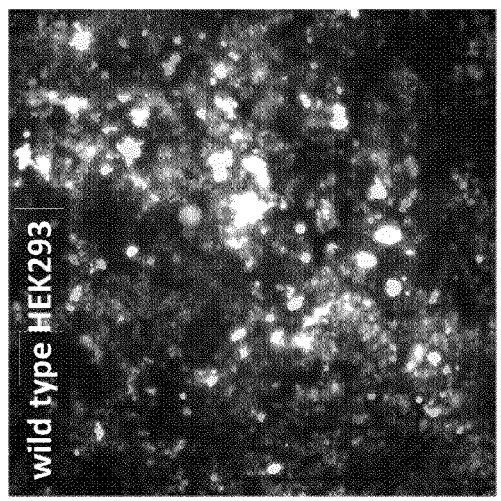

FIG. 58a illustrates the transduction of HEK293 cells by AAV2 as analyzed by microscopy. FIG. 58b illustrates the transduction of HEK293 cells by AAV2 upon deletion of the AAVR gene.

Figure 59B:
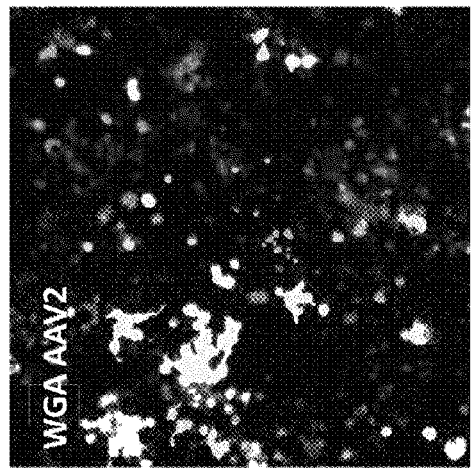
Figure 59A:
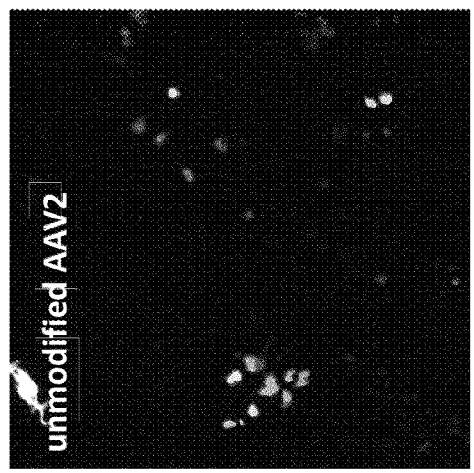

FIGS. 59a-59b are representative images of transduction of AAVR-KO HEK293 cells by WT AAV2 vector (FIG. 59a) and (FIG. 59b) WGA-AAV2.

Figures 60A, 60B:
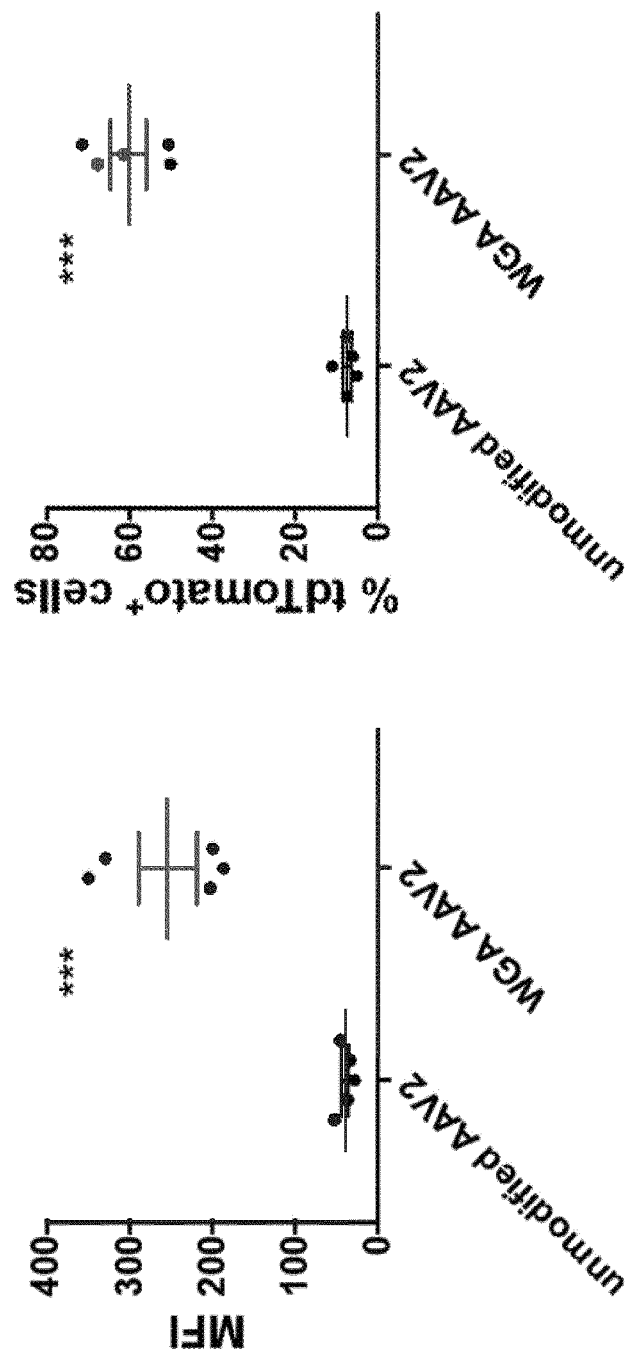

FIGS. 60a-60b are mean fluorescence intensity (MFI) and % of tdtomato positive cells, respectively, data characterizing transduction of AAVR KO HEK293 cells by WT AAV2 vector and WGA-AAV2.

FIG. 61 is the synthesized amino acid Sequence of Nemolizumab SNAP containing an upstream GP64 signal sequence, and downstream Sortag, SNAP-tag and 6×His tag. The GP 64 signal sequence is shown in italics, Nemolizumab in bold, Sortag underlined, Snap tag in grey, 6×HIS in grey bold (SEQ ID NO. 3), asterisk indicates stop codon.

Figures 62A, 62B, 62C:
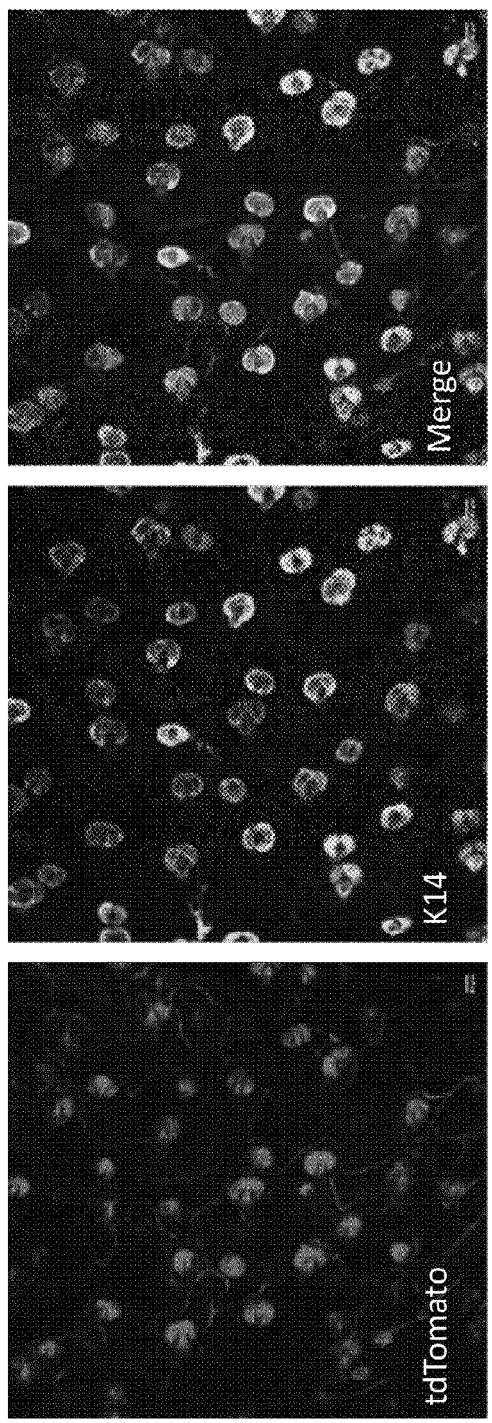

FIGS. 62a-62c illustrate the histological analysis of transduction selectivity in the skin of wildtype mice following subcutaneous injection of 3 E+10 VG particles of the Nemolizumab-AAV2• HSPG construct. FIG. 62a shows the fluorescent tdTomato signal from Nemoluzimab SNAP AAV2• HSPG virally infected cells (red). FIG. 62b shows keratinocytes identified using an antibody against K14 (green). FIG. 62c shows a merged image of the virally infected keratinocytes (orange).

FIGS. 63a-63b illustrate human antibody-mediated recognition and neutralization of surface modified AAV2, functionalized using different amounts of DBCO-PEGn linker. FIG. 63a binding of IgG contained in pooled human serum to AAV2, functionalized using different amounts of DBCO-PEGn linker, measured by ELISA and expressed as optical density (OD) units measured at 450 nm light. FIG. 63b illustrates neutralization assay performed in HEK293T cells with unmodified and modified virus preincubated with different dilutions of pooled human serum where percentage of inhibition of transduction is indicated for each serum dilution.

FIGS. 64a-64c illustrate antibody recognition and neutralization upon chemical modification of AAV2 using linkers with various PEG length on both virus and ligand. FIG. 64a illustrates human IgG binding to AAV2 modified with different linker PEG length for virus and ligand, measured as in FIG. 63a. FIGS. 64b-64c illustrates neutralization activity of human antibodies toward unmodified and modified virus pre-incubated with different dilutions of human pooled serum, as in FIG. 63b, where 4 virus=DBCO PEG4; 2K virus=DBCO-PEG2000; 5K ligand=WGA-PEG5000-Azide; 4 ligand=WGA-PEG4-Azide).

FIGS. 65a-65n illustrate a neutralization assay using unmodified and AAV2-WGA in PC12 cells. Unmodified (FIG. 65a-65g) and AAV2-WGA modified using PEG4-Azide (FIG. 65h-n) were incubated with 2-fold serial dilutions of AAV2-immunized mouse serum before adding to PC12 cells.

FIGS. 66a-66f illustrate a neutralization assay with primary DRG neurons using unmodified (FIG. 66a-66c) and AAV2-WGA modified using PEG4-Azide (FIG. 66d-66f). Unmodified and AAV2-WGA were pre-incubated with dilutions of mouse serum containing antibodies against AAV2 before adding to DRG cultures.

7. DETAILED DESCRIPTION OF THE INVENTION a. Definitions

The term "rAAV" as used herein refers to a recombinant virion comprising a recombinant nucleic acid construct packaged within an AAV capsid.

The recombinant nucleic acid construct (synonymously, "recombinant viral genome") comprises a polynucleotide payload (synonymously, "cargo") positioned between AAV inverted terminal repeats. The payload can be an expressible polynucleotide or a DNA construct that provides a template for homology directed repair. In various embodiments, the expressible polynucleotide encodes a protein (e.g., a transgene encoding a therapeutic protein), or encodes an miRNA, siRNA, or a guide RNA for gene editing or RNA editing machinery such as CRISPR, ADAR, and ADAT.

The terms "AAV", "adeno-associated virus", "AAV virus", "AAV virion", "AAV viral particle", "AAV particle", "adeno-associated viral vector", and "AAV vector" are used synonymously herein for rAAV.

As used herein, "binding of a capsid" or "binding of a surface-modified capsid" to a mammalian cell surface protein, polysaccharide, or proteoglycan intends binding of a recombinant virion, typically rAAV, that comprises said capsid or surface-modified capsid.

As used herein, the terms "treat" or "treatment" are used in their broadest accepted clinical sense. The terms include, without limitation, lessening a sign or symptom of disease; improving a sign or symptom of disease; alleviation of symptoms; diminishment of extent of disease; stabilization (i.e., not worsening) of the state of disease; delay or slowing of disease progression; amelioration or palliation of the disease state; remission (whether partial or total), whether detectable or undetectable; cure; prolonging survival as compared to expected survival if not receiving treatment.

An "effective amount" is an amount of the AAV particle of the present invention effective to treat a disease.

As used herein, the term "prevention" or "preventing" when used in the context of a subject refers to prophylaxis of a disease, typically in a subject at risk for developing the disease, for example by presence of a genomic mutation.

As used herein the tem' "tropism" refers to preferential infection and/or transduction by a viral capsid of certain cells or tissues. In a preferred embodiment, to modify an AAV capsid's tropism, the capsids are being given certain features such as certain affinities to receptors on the target cell's surface which they do not possess by nature.

In the context of the present invention, the term "subject", as used in certain embodiments, preferably refers to a mammal, such as a mouse, rat, guinea pig, rabbit, cat, dog, monkey, or preferably a human. The term "patient" preferably refers to a mammal, such as a mouse, rat, guinea pig, rabbit, horse, cattle, cow, cat, dog, monkey, or preferably a human, for example a human patient, for whom diagnosis, prognosis, or therapy is desired. The subject of the invention may be at danger of suffering from a disease, such as a bacterial infection, a viral infection, a fungal infection, or a parasitic infection. A more detailed description of medical indications relevant in the context of this invention is provided herein elsewhere.

The term "optionally substituted" means that a given chemical moiety (e.g., an alkyl group) can (but is not required to) be bonded other substituents heteroatoms). For instance, an alkyl group that is optionally substituted can be a fully saturated alkyl chain (e.g., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus, the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —CH$_2$CN, ($C_1$-$C_6$)alkyl, ($C_1$-$C_6$)alkoxy, ($C_1$-$C_6$)haloalkyl, ($C_1$-$C_6$)haloalkoxy, —O—($C_2$-$C_6$)alkenyl, —O—($C_2$-$C_6$)alkynyl, ($C_2$-$C_6$)alkenyl, ($C_2$-$C_6$)alkynyl, —OP(O)(OH)$_2$, —OC(O)($C_1$-$C_6$)alkyl, —C(O)($C_1$-$C_6$)alkyl, —OC(O)O($C_1$-$C_6$)alkyl, —NH2, —NH(($C_1$-$C_6$)alkyl), —N(($C_1$-$C_6$)alkyl)2, —NHC(O)($C_1$-$C_6$)alkyl, —C(O)NH($C_1$-$C_6$)alkyl, —S(O)2($C_1$-$C_6$)alkyl, —S(O)NH($C_1$-$C_6$)alkyl, and S(O)N(($C_1$-$C_6$)alkyl)$_2$. The substituents can themselves be optionally substituted. "Optionally substituted" as used herein also refers to substituted or unsubstituted whose meaning is described below. A moiety that includes additional substitution is referred to herein as a "derivative" of the substituted moiety. For example, an alkyl substituted nitrone is an example of a derivative of a nitrone moiety.

The term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

Unless otherwise specifically defined, "aryl" means a cyclic, aromatic hydrocarbon group having 1 to 3 aromatic rings, including monocyclic or bicyclic groups such as phenyl, biphenyl, or naphthyl. When containing two aromatic rings (bicyclic, etc.), the aromatic rings of the aryl group are optionally joined at a single point (e.g., biphenyl), or fused (e.g., naphthyl). The aryl group is optionally substituted by one or more substituents, e.g., 1 to 5 substituents, at any point of attachment. Exemplary substituents include, but are not limited to, -halogen, oxo, —OH, —CN, —COOH, —CH$_2$CN, —O—($C_1$-$C_6$)alkyl ($C_1$-$C_6$)alkyl, ($C_1$-$C_6$)alkoxy, ($C_1$-$C_6$)haloalkyl, ($C_1$-$C_6$)haloalkoxy, —O—($C_2$-$C_6$)alkenyl, —O—($C_2$-$C_6$)alkynyl, ($C_2$-$C_6$)alkenyl, ($C_2$-$C_6$)alkynyl, —OP(O)(OH)2, —OC(O)($C_1$-$C_6$)alkyl, —C(O)($C_1$-$C_6$)alkyl, —O C(O)O($C_1$-$C_6$)alkyl, —NH2, —NH(($C_1$-$C_6$)alkyl), —N(($C_1$-$C_6$)alkyl)2, —NHC(O)($C_1$-$C_6$)alkyl, —C(O)NH($C_1$-$C_6$)alkyl, —S(O)2($C_1$-$C_6$)alkyl, —S(O)NH($C_1$-$C_6$)alkyl, and S(O)N(($C_1$-$C_6$)alkyl)$_2$.

The substituents are themselves optionally substituted. Furthermore, when containing two fused rings, the aryl groups optionally have an unsaturated or partially saturated ring fused with a fully saturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Halogen or "halo" mean fluorine, chlorine, bromine, or iodine.

"Alkyl" means a straight or branched chain saturated hydrocarbon containing 1-12 carbon atoms. Examples of a ($C_1$-$C_6$) alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" means a straight or branched chain saturated hydrocarbon containing 1-12 carbon atoms containing a terminal "O" in the chain, e.g., —O(alkyl). Examples of alkoxy groups include, without limitation, methoxy, ethoxy, propoxy, butoxy, t-butoxy, or pentoxy groups.

"Alkenyl" means a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, isobutenyl, pentenyl, or hexenyl. An alkenyl group can be unsubstituted or substituted and may be straight or branched.

"Alkynyl" means a straight or branched chain unsaturated hydrocarbon containing 2-12 carbon atoms. The "alkynyl" group contains at least one triple bond in the chain. Examples of alkenyl groups include ethynyl, propargyl, n-butynyl, isobutynyl, pentynyl, or hexynyl. An alkynyl group can be unsubstituted or substituted.

"Cycloalkyl" or "carbocyclyl" means a monocyclic or polycyclic saturated carbon ring containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl and derivatives thereof. A (C3-C8) cycloalkyl is a cycloalkyl group containing between 3 and 8 carbon atoms. A cycloalkyl group can be fused (e.g., decalin) or bridged (e.g., norbomane).

"Haloalkyl" means an alkyl group substituted with one or more halogens. Examples of haloalkyl groups include, but are not limited to, trifluoromethyl, difluoromethyl, pentafluoroethyl, trichloromethyl, etc.

"Haloalkoxy" means an alkoxy group substituted with one or more halogens. Examples of haloalkyl groups include, but are not limited to, trifluoromethoxy, difluoromethoxy, pentafluoroethoxy, trichloromethoxy, etc.

The term "pharmaceutically acceptable" as used herein refers to molecular entities and compositions that are physiologically tolerable and do not typically produce toxicity or an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

As used herein the "therapeutic index" its a parameter expressing the therapeutic efficiency of the active drug. It is for example low when implying that high concentration of the active substance is needed to achieve therapeutic efficacy or when the dose required obtaining efficacy induce toxicity. On the contrary, high therapeutic index implies that the dose required of the active substance to provide therapeutic efficacy is low and/or when toxicity of the active drug is low.

b. Other Interpretational Conventions

Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

It must be noted that as used herein and in the appended claims, the singular forms "a," "an," and "the" include plural referents unless the context clearly dictates otherwise. Thus, for example, reference to "an antibody or antigen binding fragment" includes a plurality of such antibodies and antigen binding fragments and reference to "the recombinant adeno-associated virus" includes reference to one or more recombinant adeno-associated viruses and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. The dates of publication provided may be different from the actual publication dates, which may need to be independently confirmed.

Where a range of values is provided, it is understood that the recited endpoints of the range are included. In addition, each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50, including subranges such as from 11 to 48 or 39 to 41.

The term "about" as used herein can allow for a degree of variability in a value or range, for example, within 10% of a stated value or of a stated limit of a range.

c. Surface Modified Viral Capsid

In accordance with the present disclosure, a surface modified viral capsid is provided that comprises a ligand covalently conjugated to a viral capsid protein via a linker comprising a crosslinked moiety, Q. Also provided are recombinant virions that comprise the surface modified viral capsid.

In some embodiments, the provided surface modified viral capsid confers improved transduction efficiency, improved cell-type selectivity, or both improved transduction efficiency and improved cell-type selectivity on a recombinant virion of which it is a part, when compared to an unmodified recombinant virion, e.g., comprising a viral capsid having the same primary amino acid sequence but that has not been modified as described herein to crosslink to a ligand.

In accordance with the present disclosure, a surface functionalized viral capsid is provided comprising a first member of a crosslinker reactive pair. Also provided is a functionalized ligand comprising a second member of a crosslinker reactive pair, wherein the first and second members of the crosslinker reactive pair react to form a crosslinked moiety, Q. The surface functionalized viral capsid is capable of being crosslinked, i.e., conjugated, to a ligand having a complementary member of a crosslinker reactive pair.

In some embodiments, the surface modified viral capsid in a composition comprises x conjugated ligands where x is the average number of ligands conjugated per capsid in a composition, also referred to herein as the ligand per capsid ratio or LCR. In some embodiments, x is from 1 to 500. In certain embodiments x is from 1 to 300. In certain embodiments x is from 100 to 200. In certain embodiments x is from 110 to 190. In certain embodiments x is from 130 to 170. In some embodiments, x is 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295 or 300, or a range defined by any two of the preceding numbers. In certain embodiments, x is about 1350, about 140, about 145, about 150, about 155, about 160, about 165, about 170, about 175 or about 180. In certain embodiments, x is from about 55 to about 85. In certain embodiments, x is from about 140 to about 160. In certain embodiments, x is from about 135 to about 165. In certain embodiments, x is from about 130 to about 170. In certain embodiments, x is about 150. In certain embodiments, x is in a range between any two of numbers the provided above.

Also provided by the present disclosure are capsid-reactive linkers comprising (i) a capsid reactive moiety that is capable of covalent attachment to a viral capsid protein, and (ii) a member of a crosslinker reactive pair.

In embodiments of the present disclosure, a surface modified viral capsid according to the present disclosure is produced by the steps of:
i) obtaining a surface functionalized viral capsid by reacting a viral capsid protein with a capsid-reactive linker comprising a first member of a crosslinker reactive pair and optionally one or more of a spacer; and
ii) conjugating the surface functionalized viral capsid with a functionalized ligand comprising a second member of the crosslinker reactive pair,
wherein the first and second members of the crosslinker reactive pair react to form a crosslinked moiety, Q; and
iii) obtaining the surface modified viral capsid.

a. Crosslinker Reactive Pair

To effect covalent conjugation of a ligand to a viral capsid to create a surface modified viral capsid, recombinant virions are surface-functionalized to create surface functionalized viral capsid proteins, which are then reacted with a functionalized ligand. The surface functionalized capsid and functionalized ligand each comprise a member of a crosslinker reactive pair. The crosslinker reactive pair members react to form a moiety, Q, that covalently cross-links the viral capsid to the ligand.

In typical embodiments, the crosslinker reactive pair members are bioorthogonal. As used herein, the term bioorthogonal chemistry refers to any chemical process that can occur inside of living systems without interfering with native biochemical processes or can occur in vitro without interfering with biochemical/biological activity of the reaction products. A number of chemical conjugation strategies have been developed that fulfill the requirements of bioorthogonality, including the 1,3-dipolar cycloaddition between azides and cyclooctynes (also termed copper-free click chemistry), between nitrones and cyclooctynes, oxime/hydrazone formation from aldehydes and ketones, the tetrazine ligation, e.g., the cycloaddition of s-tetrazine and trans-cyclooctene derivatives or isocyanide-based click reaction, and most recently, the quadricyclane ligation.

a. CuAAC

In certain embodiments, the crosslinker reactive pair is selected from chemical moieties that participate in a Cu(I)-catalyzed azide-alkyne cycloaddition (CuAAC). In certain embodiments, the crosslinker reactive pair comprises an azide and an alkyne. Derivatives of these moieties that retain the desired chemical reactivity are also contemplated herein. In certain embodiments, the crosslinked moiety Q comprises a 5-membered heteroatom ring. In certain embodiments, the crosslinked moiety Q comprises a 1,4 triazole.

b. SPAAC and SPANC

Unlike CuAAC, Cu-free click chemistry has been modified to be bioorthogonal by eliminating a cytotoxic copper catalyst, allowing reaction to proceed quickly and without live cell toxicity. Instead of copper, the reaction is a strain-promoted alkyne-azide cycloaddition (SPAAC). Copper-free click chemistry has been adapted to use nitrones as the 1,3-dipole rather than azides and has been used in the modification of peptides.

In certain embodiments, the crosslinker reactive pair is selected from chemical moieties that participate in a strain-promoted alkyne-nitrone cycloaddition (SPANC). In certain embodiments, the crosslinker reactive pair comprises an azide and a nitrone. Derivatives of these moieties that retain the desired chemical reactivity are also contemplated herein. In certain embodiments, the crosslinked moiety Q comprises an isoxazoline.

In some embodiments, the crosslinker reactive pair is an azide and a nitrone, as illustrated below, where the R group represents the point of attachment to the capsid-reactive linker or functionalized ligand. Derivatives of these moieties that retain the desired chemical reactivity are also contemplated herein. For example, substitution on both the carbon and nitrogen atoms of the nitrone dipole, and acyclic and endocyclic nitrones are all tolerated.

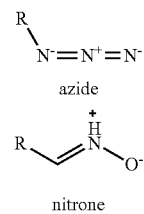

In some embodiments, the crosslinker reactive pair comprises a cyclooctyne analogue. In certain embodiments, the crosslinker reactive pair comprises a cyclooctyne analogue, e.g., those illustrated below where the R group represents the point of attachment to the capsid-reactive linker or functionalized ligand. Derivatives of these moieties that retain the desired chemical reactivity are also contemplated herein.

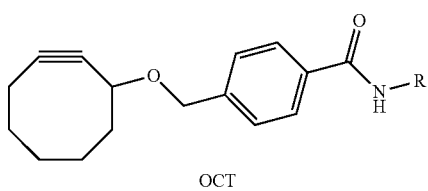

OCT

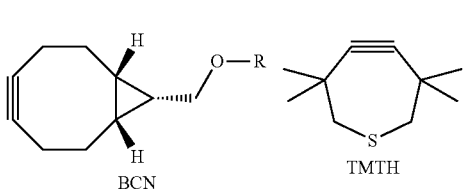

BCN     TMTH

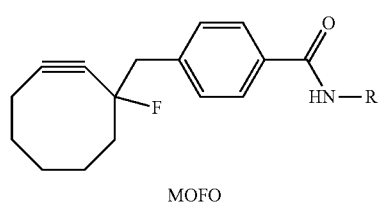

MOFO

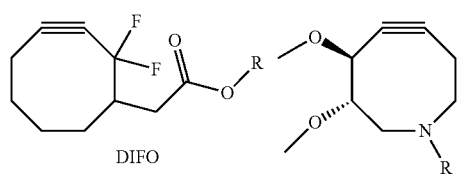

DIFO     DIMAC

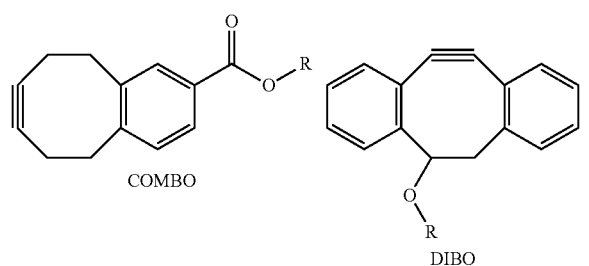

COMBO     DIBO

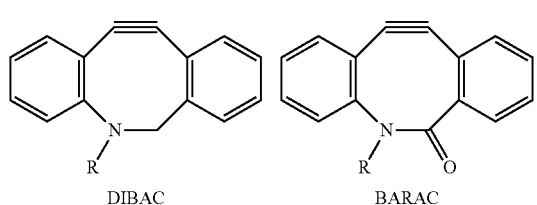

DIBAC     BARAC

In certain embodiments, the crosslinker reactive pair comprises a dibenzylcyclooctyne analog selected from the group dibenzylcyclooctyne (DIBO), Dibenzoazacyclooctyne (DIBAC or DBCO), and biarylazacyclooctynone (BARAC). Derivatives of these moieties that retain the desired chemical reactivity are also contemplated herein.

In certain embodiments, the crosslinker reactive pair comprises a nitrone according the structure below, where the $R_1$ group represents the point of attachment to the capsid-reactive linker or functionalized ligand. $R_2$ and $R_3$ are not particularly limited. In some embodiments, $R_2$ and $R_3$ are independently selected from hydrogen and C—C4 alkyl groups such as methyl, ethyl, propyl and butyl groups. Derivatives of these moieties that retain the desired chemical reactivity are also contemplated herein.

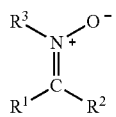

In certain embodiments, the crosslinker reactive pair comprises a dibenzylcyclooctyne analog as identified above and either a 1,3-nitrone or an azide. In certain embodiments, the crosslinker reactive pair comprises a dibenzylcyclooctyne (or analog thereof) and either a 1,3-nitrone or an azide, as shown below, where the $R_1$ group represents the point of attachment to a viral capsid or a capsid-reactive linker, and wherein $R_2$ group on either the azide or the nitrone represents the point of attachment to a functionalized ligand. In alternative embodiments, the crosslinker reactive pair comprises a dibenzylcyclooctyne (or analog thereof) and either a 1,3-nitrone or an azide, as shown below, where the $R_1$ group represents the point of attachment to a ligand and wherein $R_2$ group on either the azide or the nitrone represents the point of attachment to a surface functionalized viral capsid or a capsid-reactive linker.

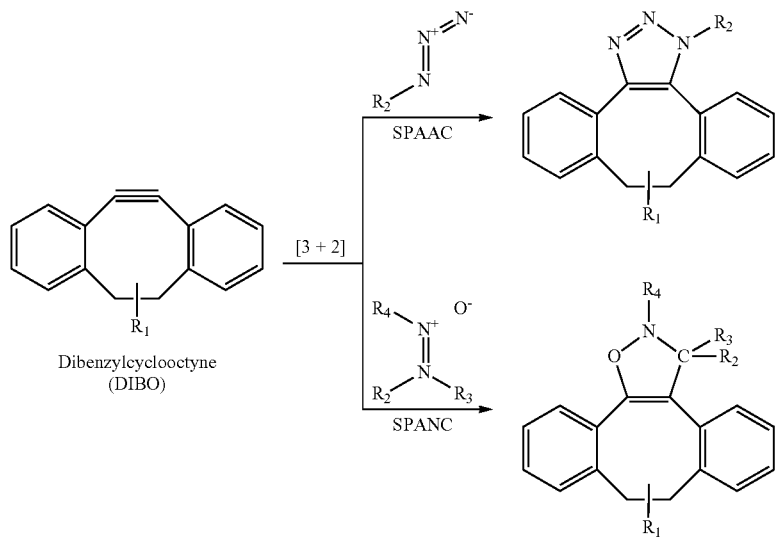

In certain embodiments, the crosslinked moiety Q comprises a cyclic moiety according to any one of those illustrated below, where $R_1$ and $R_2$ represent the point of attachment to the viral capsid. $R_3$ and $R_4$ may be H or any substituent described herein, provided the substituted derivatives retain the desired chemical reactivity are also contemplated herein.

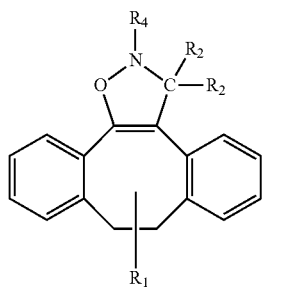

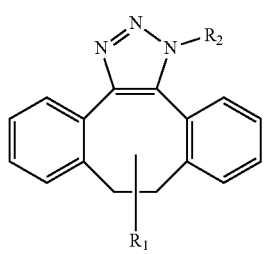

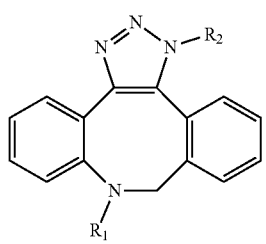

-continued

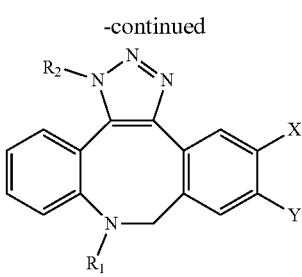

c. IEDDA

In certain embodiments, the crosslinker reactive pair comprises chemical moieties that participate in an inverse electron demand Diels-Alder (IEDDA) reaction. In certain embodiments, the crosslinker reactive pair comprises an electron poor diene and an electron rich dienophile. Examples of such groups are known in the art and described elsewhere, for example, F. Thalhammer, et al., *Tetrahedron Lett.*, 1990, 31, 6851-6854: and B. L. Oliveira, *Chem. Soc. Rev.*, 2017, 46, 4895-4950. In some embodiments, the electron poor diene has an electron withdrawing group substituted on the diene as exemplified below. In some embodiments, the electron rich dienophile has an electron donating group substituted on the dienophile, as exemplified below.

Inverse electron demand

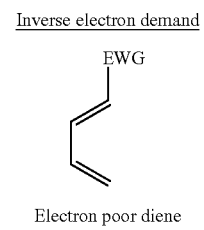

Electron poor diene

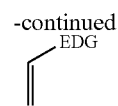

Electron rich dienophile

In certain embodiments, the crosslinker reactive pair comprises chemical moieties that participate in a Diels-Alder [4+2]-cycloaddition, the reaction between a diene and a dienophile to form a six-membered ring in a •4 s+•2 s fashion via suprafacial/suprafacial interaction of 4•-electrons of the diene with the 2•-electrons of the dienophile. In contrast to a normal electron demand Diels-Alder reaction, where an electron-rich diene reacts with an electron-poor dienophile, in an inverse-electron-demand Diels-Alder reaction (IEDDA), an electron-rich dienophile reacts with an electron-poor diene. Alkyne dienophiles directly yield the respective pyridazine upon reaction.

In certain embodiments, the crosslinker reactive pair comprises a triazine (e.g., 1, 2, 4 triazine), a tetrazine (Tz) (e.g., 1,2,4,5-tetrazines, also referred to as an s-tetrazine) or a strained dienophile such as noroborene, transcyclooctene (TCO), cyclopropene, or N-acylazetine. In certain embodiments, the crosslinker reactive pair comprises a moiety exemplified below, where the R group represents the point of attachment to a capsid-reactive linker, surface functionalized viral capsid, or functionalized ligand of the present disclosure. Derivatives of these moieties that retain the desired chemical reactivity are also contemplated herein. In certain embodiments, the crosslinker reactive pair comprises TCO and tetrazine.

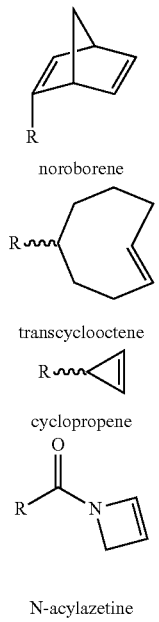

7.1.1.1 Staudinger Ligation

In certain embodiments, the crosslinker reactive pair is selected from a chemical moiety that participates in a Staudinger reaction such as an azide, a phosphine (PPh$_2$) or phosphite that are able to react to produce an iminophosphorane.

In certain embodiments, the crosslinker reactive moiety is a triphenylphosphine, such as the triphenylphosphine shown below where the R group represents the point of attachment to the capsid-reactive linker of the present disclosure. Derivatives of this moiety that retains the desired chemical reactivity is also contemplated herein.

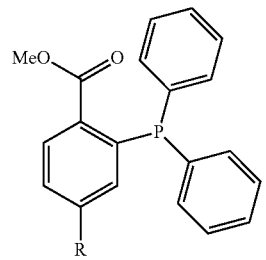

d. [4+1] Cycloaddition

In certain embodiments, the crosslinker reactive pair is selected from a chemical moiety that participates in an a [4+1] cycloaddition followed by a retro-Diels Alder elimination of N$_2$, e.g., an isocyanide or a 1,2,4,5, tetrazine.

In some embodiments, the crosslinker reactive moiety is an isocyanide as shown below, where the R group represents the point of attachment, e.g., to the capsid-reactive linker. In some embodiments, the crosslinker reactive moiety is a 1,2,4,5, tetrazine as shown below, where the R1 or R2 group represents the point of attachment, e.g., to the ligand. Derivatives of these moieties that retain the desired chemical reactivity are also contemplated herein.

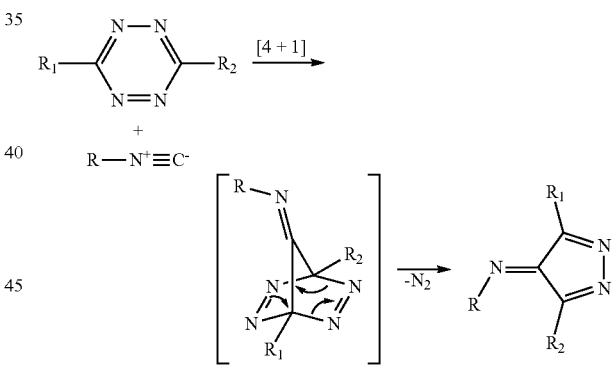

7.1.1.1 Tag Reactions

In certain embodiments, the crosslinker reactive moiety is a bioorthogonal tag known in the art, such as a SNAP-tag, a CLIP tag, a Halo-tag, or LUMIO-tag or a chemical group that reacts with these tags, e.g., benzylguanine group, a benzylcytosine group, or a chloroalkane group. In certain embodiments, one member of the crosslinker reactive moiety comprises a SNAP-tag and the other member of the crosslinker reactive moiety comprises a benzylguanine group.

b. Crosslinked Moiety—Q

In an aspect of the present disclosure, the surface modified viral capsid comprises a moiety, Q, that is a moiety formed by the reaction between a crosslinker reactive pair as described herein.

In certain embodiments, Q comprises the product of a CuAAC reaction. In certain embodiments, Q comprises the product of a SPAAC reaction. In certain embodiments, Q is the product of a SPANC reaction. In certain embodiments, Q comprises the product of an IEEDD reaction. In certain embodiments, Q comprises the product of a Staudinger ligation. In certain embodiments, Q comprises the product of a [4+1] cycloaddition reaction. In some embodiments, Q comprises the product of a strain promoted reaction, e.g., SPAAC, SPANC, and IEEDD.

In certain embodiments, Q comprises a cyclic moiety. In certain embodiments, Q comprises a bicyclic moiety. In certain embodiments, Q comprises a tricyclic moiety. In certain embodiments, Q comprises a 5-8 membered carbocyclic ring comprising from 0 to 3 heteroatoms selected from 0, S or N. In certain embodiments, Q comprises an eight membered ring comprising 0 to 1 heteroatom selected from 0 and N. In certain embodiments, Q comprises a five membered ring comprising 0 to 3 heteroatoms selected from 0 and N. In certain embodiments, Q is a triazole ring. In certain embodiments, Q comprises a six membered ring comprising 0-3 heteroatoms selected from 0 and N. In certain embodiments, Q comprises a six membered ring comprising 2 N heteroatoms.

In some embodiments, where Q comprises a cyclic moiety, Q is according to a structure below, where Z is a 7 or 8 membered carbocycle comprising from 0-3 heteroatoms selected from 0 or N.

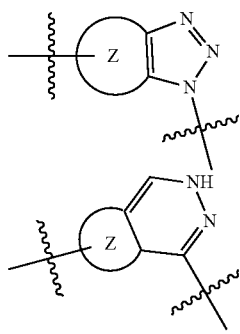

In some embodiments, Q comprises a structure below:

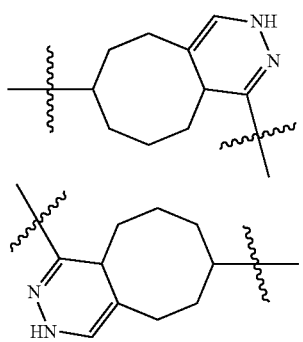

C. Surface Functionalized Viral Capsid

In an aspect of the present disclosure, a surface functionalized viral capsid is provided wherein the surface of the viral capsid is functionalized to comprise a member of a crosslinker reactive pair. In some embodiments, a viral capsid protein is functionalized by a reaction with a capsid-reactive linker. In some embodiments, the surface of the viral capsid comprises a non-natural amino acid comprising a crosslinker reactive moiety. In some embodiments, the viral capsid comprises a fusion protein comprising a bioorthogonal tag in the primary sequence of at least one capsid protein.

In embodiments of the present disclosure, a surface functionalized viral capsid is provided wherein the surface of the viral capsid is functionalized by reaction with a capsid-reactive linker. In some embodiments, the surface functionalized viral capsid comprises y capsid-reactive linker groups where y is the number of capsid-reactive linkers attached to each viral capsid.

In some embodiments of the present disclosure, a composition comprising the surface functionalized viral capsid is provided where Y is the average number of capsid-reactive linker attached to each capsid.

a. Capsid-Reactive Linker

The capsid-reactive linker, in accordance with the present disclosure, comprises i) a capsid surface reactive moiety available to form a covalent attachment with the capsid surface, and ii) a member of a crosslinker reactive pair selected to be mutually reactive with another member of the crosslinker reactive pair functionalized on a ligand of the present disclosure.

a. Spacer

The capsid-reactive linker optionally further comprises one or more spacer moiety. The spacer moiety is not particularly limited and may be any spacer known in the art. In some embodiments the spacer comprises one or more monomers of ethylene glycol, i.e., polyethylene glycol, •(O•CH$_2$•CH$_2$)n• or [PEG]n, also known as "dPEG n" for "discrete polyethylene glycol", where "n" is the number of ethylene oxide (or "ethylene glycol") units. In certain embodiments, n is 0. In certain embodiments, n is 1, 2, 3, 4, 5, 6, 7, 8, 9, 10, 11, 12, 13, 14, 15, 16, 17, 18, 19, 20, 25, 30, 35, 40, 45, 50, 75, 100.

b. Capsid Surface Reactive Moiety

In accordance with the present disclosure, the capsid surface reactive moiety is not particularly limited and includes any moiety that is able to covalently attach to the desired capsid surface.

In some embodiments, the capsid surface reactive moiety covalently attaches to a surface exposed amino acid residue in the capsid protein primary sequence using known techniques in residue specific protein labeling.

In some embodiments, the amino acid residue is present in the wild-type capsid protein. In other embodiments, the amino acid residue is engineered into the primary amino acid sequence of the capsid.

a. Capsid Surface Primary Amine

In some embodiments, the capsid surface reactive moiety comprises a chemical group that reacts with primary amines (—NH$_2$). Primary amines exist at the N-terminus of each capsid protein and in the side-chain of lysine (Lys, K) amino acid residues in the capsid protein sequence. Exemplary chemical groups that react with primary amines include isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters. Most of these conjugate to amines by either acylation or alkylation. In some embodiments, the capsid surface reactive moiety comprises an NHS ester or an imidoester, e.g., such as those illustrated below where the R group represents the point of attachment to the capsid-reactive linker.

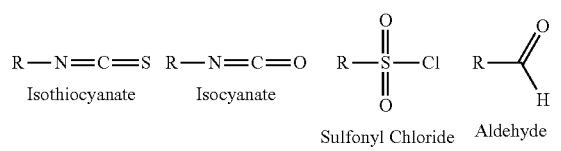

Isothiocyanate, Isocyanate, Sulfonyl Chloride, Aldehyde, Carbodiimide, Acyl Azide, Anhydride, Fluorobenzene, Carbonate, NHS Ester, Imidoester, Epoxide, Fluorophenyl ester In some embodiments, the capsid surface reactive moiety covalently attaches to a surface exposed lysine residue of the capsid protein primary sequence. In certain of these embodiments, the capsid surface reactive moiety comprises an NHS-ester, an isocyanate, an isothiocyanate, or a benzyl fluoride as shown below, where the R group represents the point of attachment to the capsid-reactive linker and the symbols denote the points of attachment of the lysine residue in the capsid protein sequence.

In some embodiments, the capsid-reactive linker comprises an N-hydroxysuccinimide ester (NHS ester). NHS esters are reactive groups formed by carbodiimide-activation of carboxylate molecules. The NHS ester-activated capsid-reactive linker reacts with primary amines in physiologic to slightly alkaline conditions (pH 7.2 to 9) to yield stable amide bonds. The reaction releases N-hydroxysuccinimide (NHS).

In some embodiments, the capsid-reactive linker comprises tetrafluorophenyl (TFP) ester. TFP esters are reactive groups formed by carbodiimide-activation of carboxylate molecules. TFP ester of carboxylic acids react with primary amines at the same rate as NHS ester forming covalent amide bond that is identical to one formed by the reaction between primary amines and NHS esters.

b. Capsid Surface Sulfhydryl Group

In some embodiments, the capsid surface reactive moiety covalently attaches to a surface exposed sulfhydryl group. In some embodiments, the capsid surface reactive moiety covalently attaches to a surface exposed cysteine residue of the capsid protein primary sequence.

In certain of these embodiments, the capsid surface reactive moiety comprises a maleimide, an iodoacetamide, a 2-thiopyridne, or a 3-arylpropiolonitrile as exemplified below, where the R group represents the point of attachment to the capsid-reactive linker and the

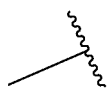 [SMILES: *CC]

symbols denote the points of attachment of the lysine residue in the capsid protein sequence.

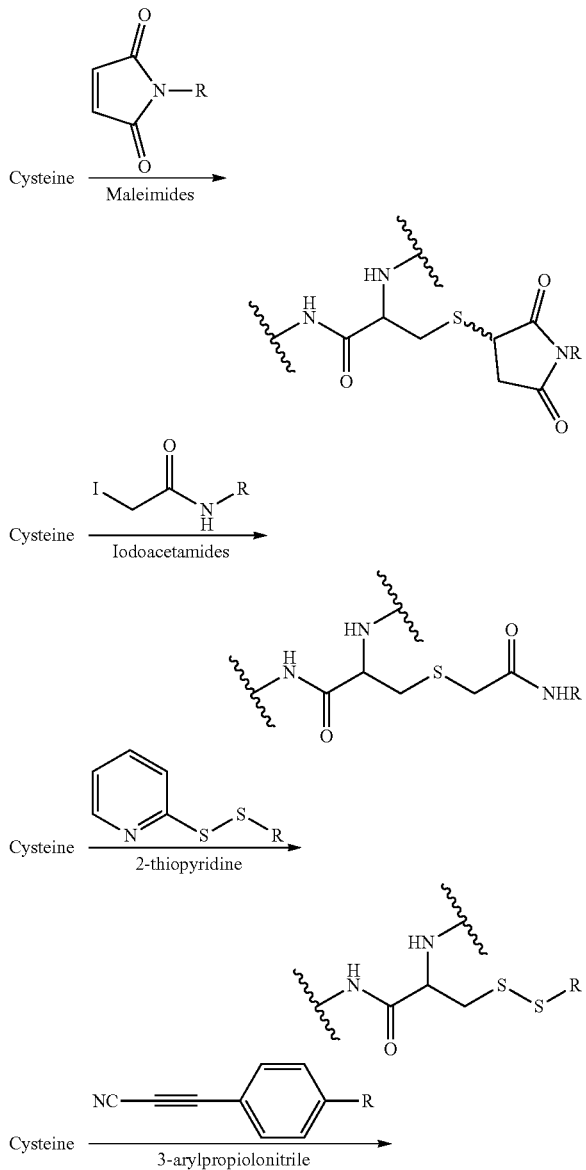

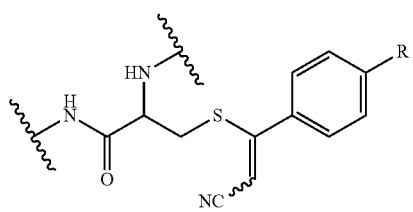

In some embodiments, the capsid-reactive linker comprises a maleimide. Maleimide and its derivatives are prepared from maleic anhydride by treatment with amines followed by dehydration. The maleimide group reacts specifically with sulfhydryl groups when the pH of the reaction mixture is between 6.5 and 7.5; the result is formation of a stable thioether linkage that is not reversible.

c. Non-Natural Amino Acids

In some embodiments, the surface of the viral capsid comprises one or more proteins that have a non-natural amino acid comprising a crosslinker reactive moiety.

In certain embodiments, the non natural amino acid selected from: 1: 3-(6-acetylnaphthalen-2-ylamino)-2-aminopropanoic acid (Anap), 2: (S)-1-carboxy-3-(7-hydroxy-2-oxo-2H-chromen-4-yl)propan-1-aminium (CouAA), 3: 3-(5-(dimethylamino)naphthalene-1-sulfonamide) propanoic acid (Dansylalanine), 4: N*-p-azidobenzyloxycarbonyl lysine (PABK), 5: Propargyl-L-lysine (PrK), 6: N*-(1-methylcycloprop-2-enecarboxamido) lysine (CpK), 7: N*-acryllysine (AcrK), 8: N*-(cyclooct-2-yn-1-yloxy)carbonyl)L-lysine (CoK), 9: bicyclo[6.1.0]non-4-yn-9-ylmethanol lysine (BCNK), 10: trans-cyclooct-2-ene lysine (2•-TCOK), 11: trans-cyclooct-4-ene lysine (4•-TCOK), 12: dioxo-TCO lysine (DOTCOK), 13: 3-(2-cyclobutene-1-yl) propanoic acid (CbK), 14: N*-5-norbornene-2-yloxycarbonyl-L-lysine (NBOK), 15: cyclooctyne lysine (SCOK), 16: 5-norbornen-2-ol tyrosine (NOR), 17: cyclooct-2-ynol tyrosine (COY), 18: (E)-2-(cyclooct-4-en-1-yloxyl)ethanol tyrosine (DS1/2), 19: azidohomoalanine (AHA), 20: homopropargylglycine (HPG), 21: azidonorleucine (ANL), and 22: N*-2-azideoethyloxycarbonyl-L-lysine (NEAK), as illustrated below.

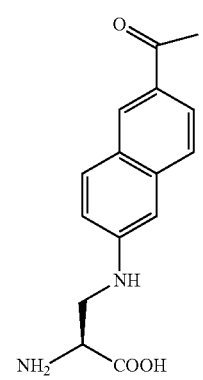

1

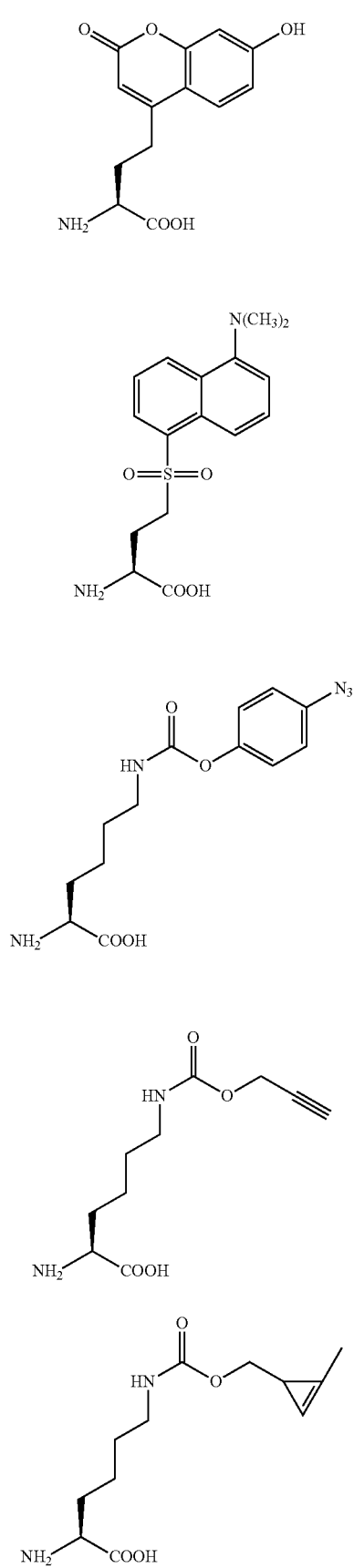
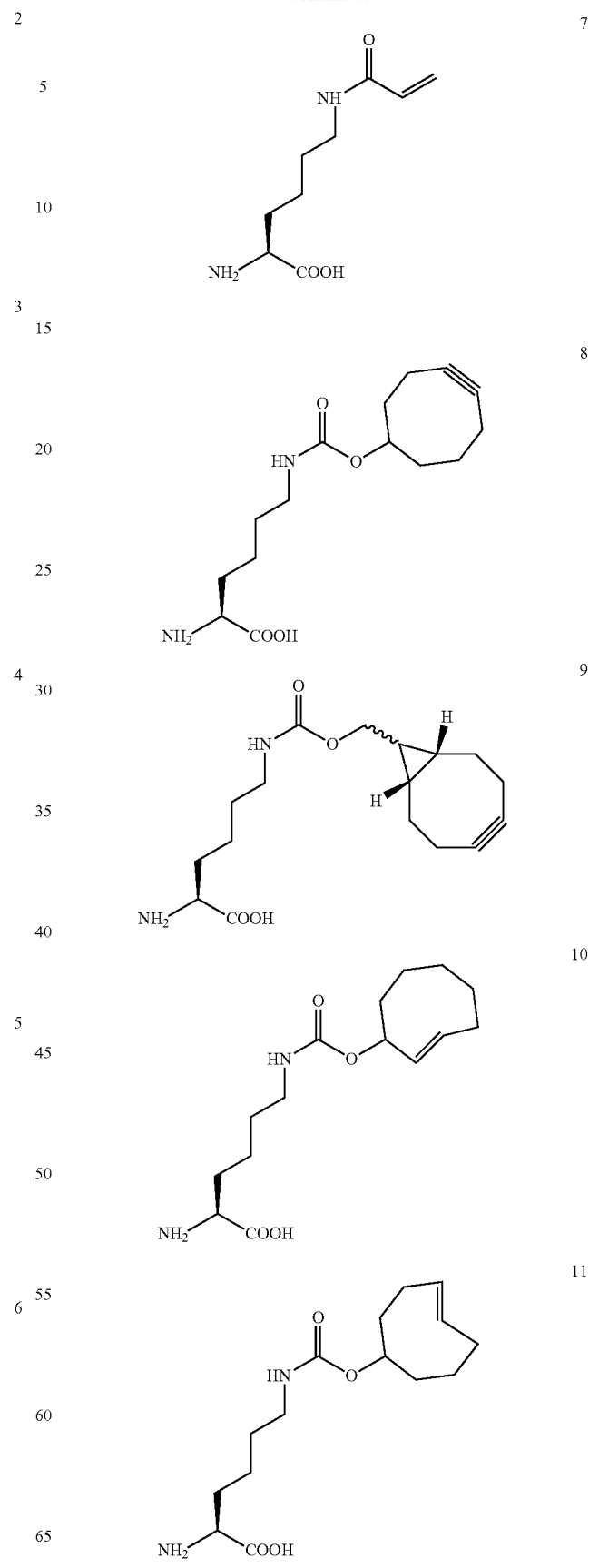

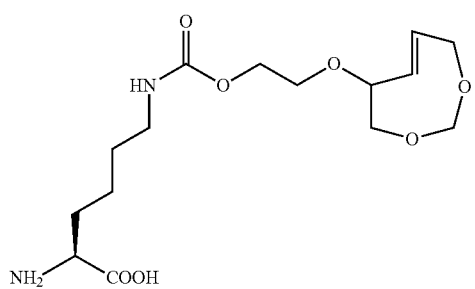
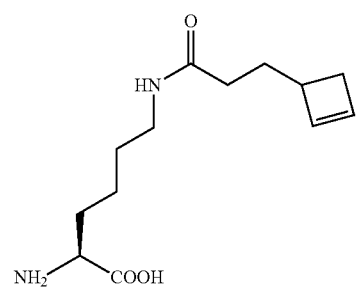
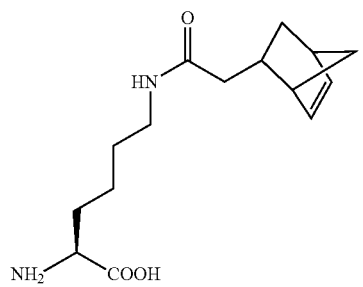
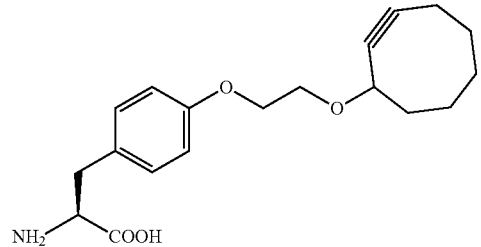
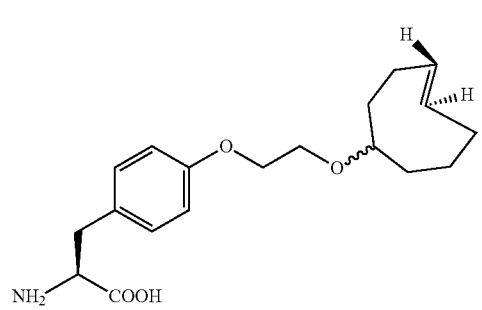
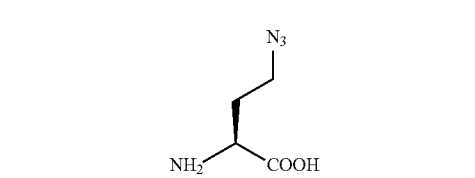
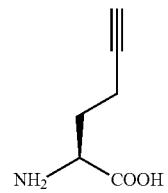
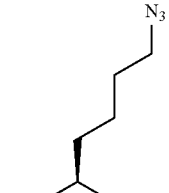
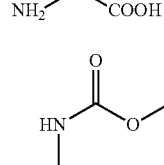
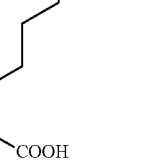
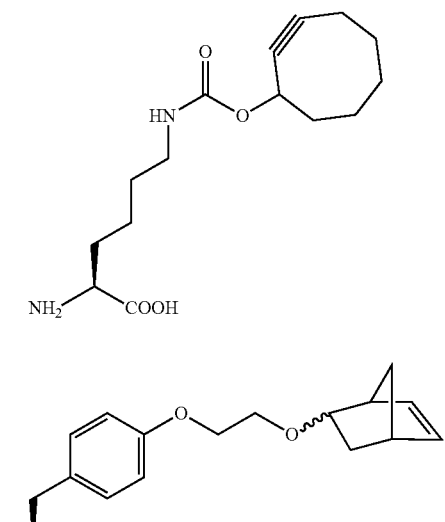
d. Functionalized Ligand
In an aspect of the present disclosure, a functionalized ligand is provided wherein the ligand is functionalized to comprise a member of a crosslinker reactive pair. In some embodiments, the ligand is functionalized by reaction with a ligand-reactive linker. In some embodiments, the ligand is a polypeptide, and the polypeptide is mutated to include a non-natural amino acid comprising a crosslinker reactive moiety. In some embodiments, the ligand is a fusion protein comprising a bioorthogonal tag in the primary sequence of the ligand.

a. Ligand-Reactive Linker

The ligand-reactive linker, in accordance with the present disclosure, comprises i) a ligand-reactive moiety available to form a covalent attachment with the ligand surface, and ii) a member of a crosslinker reactive pair available for bioorthogonal conjugation with the surface functionalized viral capsid of the present disclosure.

a. Spacer

The ligand-reactive linker optionally further comprises at least one spacer moiety. The spacer moiety is not particularly limited and may be any spacer known in the art. In some embodiments the spacer comprises monomers of ethylene glycol, i.e., polyethylene glycol, •(O•CH$_2$•CH$_2$)n• or [PEG]n, also known as "dPEG n" for "discrete polyethylene glycol", where "n" is the number of ethylene oxide (or "ethylene glycol") units. In certain embodiments, n is 0. In certain embodiments, n is 1, 2, 3, 4, 5, 6, 7, 8, 9, 10, 11, 12, 13, 14, 15, 16, 17, 18, 19, 20, 25, 30, 35, 40, 45, 50, 75, 100. In certain embodiment, n is 4.

b. Ligand-Reactive Moiety

In accordance with the present disclosure, the ligand-reactive moiety is not particularly limited and includes any moiety that is able to covalently attach to the desired ligand.

In some embodiments in which the ligand is a peptide, an oligopeptide, or a polypeptide, the ligand-reactive moiety attaches to an amino acid residue in the ligand protein primary sequence using known techniques in residue specific protein labeling.

In some embodiments, the amino acid residue is present in the wild-type ligand protein. In other embodiments, the amino acid residue is engineered into the primary amino acid sequence of the ligand.

a. Ligand Primary Amine

In some embodiments, the ligand-reactive moiety comprises a chemical group that reacts with primary amines (—NH$_2$). In embodiments in which the ligand is a polypeptide, primary amines exist at the N-terminus of each ligand protein and in the side-chain of lysine (Lys, K) amino acid residues in the ligand protein sequence. Exemplary chemical groups that react with primary amines include isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters. Most of these chemical groups conjugate to amines by either acylation or alkylation. In some embodiments, the ligand surface reactive moiety comprises and NHS ester or an imidoester, e.g., such as those illustrated below where the R group represents the point of attachment to the ligand reactive linker.

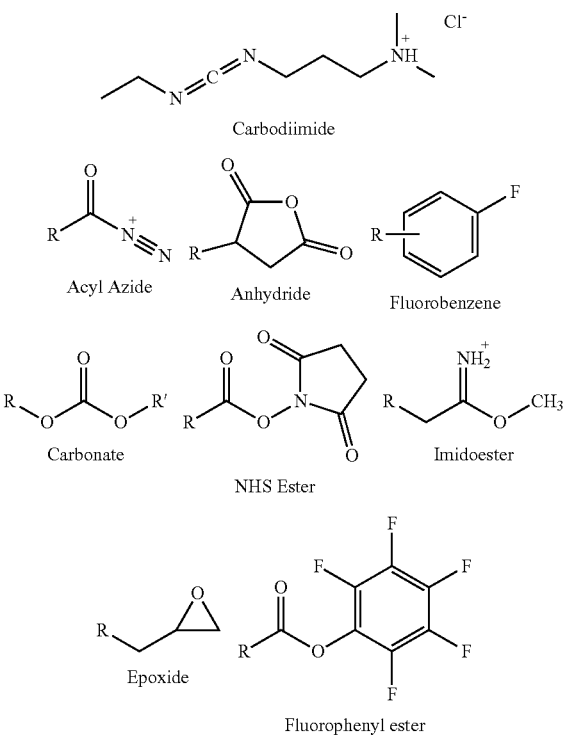

In some embodiments in which the ligand is a polypeptide, the ligand-reactive moiety covalently attaches to a surface exposed lysine residue of the ligand protein primary sequence. In certain of these embodiments, the ligand surface reactive moiety comprises an NHS-ester, an isocyanate, an isothiocyanate, or a benzyl fluoride as shown below, where the R group represents the point of attachment to the ligand reactive linker and the

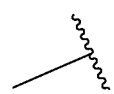 [SMILES: *CC]

symbols denote the points of attachment of the lysine residue in the ligand protein sequence.

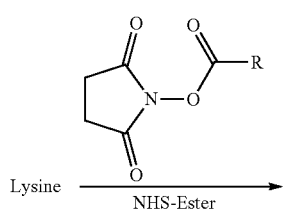

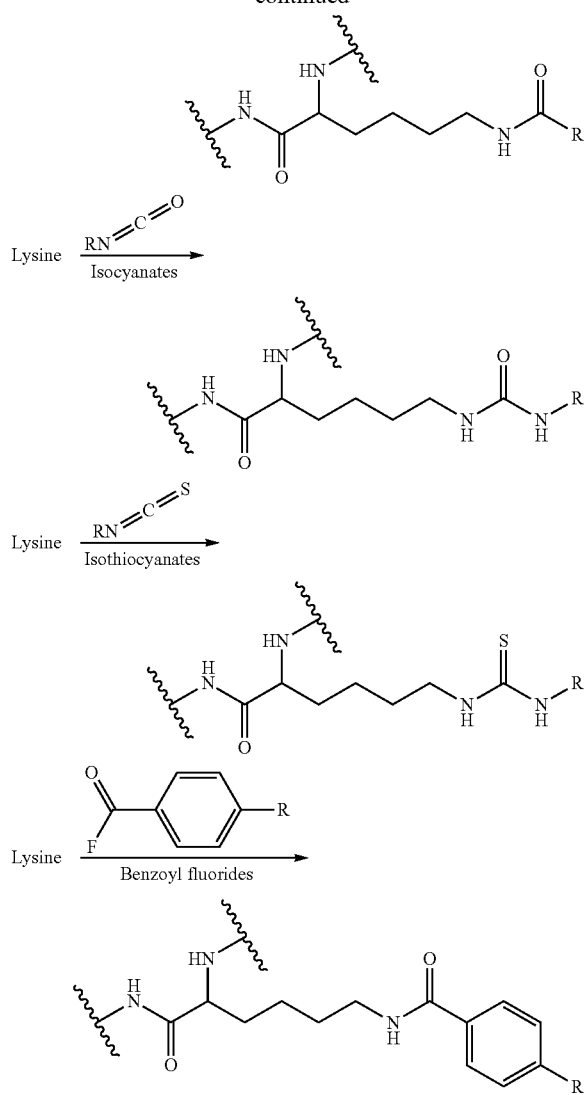

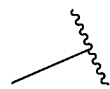

symbols denote the points of attachment of the lysine residue in the ligand protein sequence.

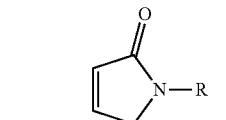

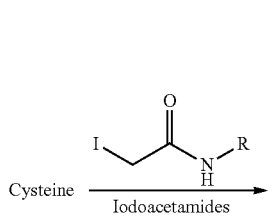

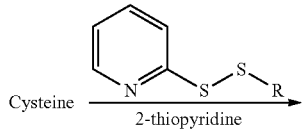

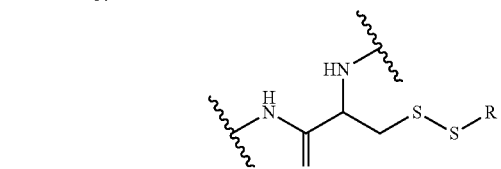

In some embodiments, the ligand-reactive linker comprises an N-hydroxysuccinimide ester (NHS ester). NHS esters are reactive groups formed by carbodiimide-activation of carboxylate molecules. The NHS ester-activated ligand reactive linker reacts with primary amines in physiologic to slightly alkaline conditions (pH 7.2 to 9) to yield stable amide bonds. The reaction releases N-hydroxysuccinimide (NHS).

b. Ligand Sulfhydryl Group

In some embodiments, the ligand-reactive moiety covalently attaches to a surface exposed sulfhydryl group. In some embodiments in which the ligand is a polypeptide, the ligand-reactive moiety covalently attaches to a cysteine residue of the ligand protein primary sequence.

In certain of these embodiments, the ligand reactive moiety comprises an maleimide, an iodoacetamide, a 2-thiopyridne, or a 3-arylpropiolonitrile as exemplified below, where the R group represents the point of attachment to the ligand reactive linker and the In some embodiments, the ligand-reactive linker comprises a maleimide. Maleimide and its derivatives are prepared from maleic anhydride by treatment with amines followed by dehydration. The maleimide group reacts specifically with sulfhydryl groups when the pH of the reaction mixture is between 6.5 and 7.5; the result is formation of a stable thioether linkage that is not reversible.

c. Non-Natural Amino Acids

In some embodiments, the ligand is a polypeptide that has been mutated to include a non-natural amino acid that comprises a crosslinker-reactive moiety.

In certain embodiments, a ligand polypeptide is mutated to comprise one or more of a non natural amino acid selected from: 1: 3-(6-acetylnaphthalen-2-ylamino)-2-aminopropanoic acid (Anap), 2: (S)-1-carboxy-3-(7-hydroxy-2-oxo-2H-chromen-4-yl)propan-1-aminium (CouAA), 3: 3-(5-(dimethylamino)naphthalene-1-sulfonamide) propanoic acid (Dansylalanine), 4: N*-p-azidobenzyloxycarbonyl lysine (PABK), 5: Propargyl-L-lysine (PrK), 6: Y-(1-methylcycloprop-2-enecarboxamido) lysine (CpK), 7: N*-acryllysine (AcrK), 8: N*-(cyclooct-2-yn-1-yloxy)carbonyl)L-lysine (CoK), 9: bicyclo[6.1.0]non-4-yn-9-ylmethanol lysine (BCNK), 10: trans-cyclooct-2-ene lysine (2•-TCOK), 11: trans-cyclooct-4-ene lysine (4•-TCOK), 12: dioxo-TCO lysine (DOTCOK), 13: 3-(2-cyclobutene-1-yl)propanoic acid (CbK), 14: N*-5-norbornene-2-yloxycarbonyl-L-lysine (NBOK), 15: cyclooctyne lysine (SCOK), 16: 5-norbornen-2-ol tyrosine (NOR), 17: cyclooct-2-ynol tyrosine (COY), 18: (E)-2-(cyclooct-4-en-1-yloxyl)ethanol tyrosine (DS1/2), 19: azidohomoalanine (AHA), 20: homopropargylglycine (HPG), 21: azidonorleucine (ANL), 22: N*-2-azideoethyloxycarbonyl-L-lysine (NEAK).

1

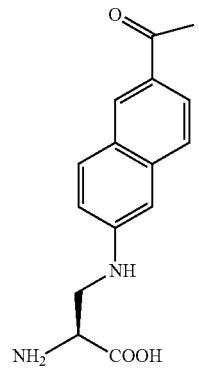

2

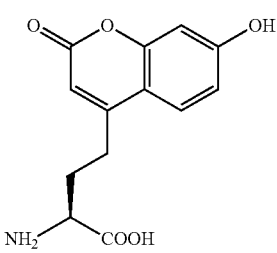

-continued

3

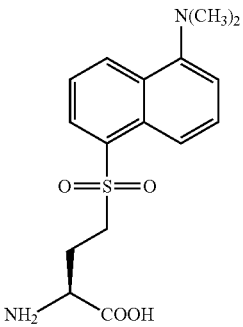

4

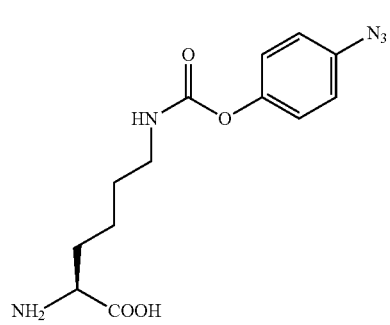

5

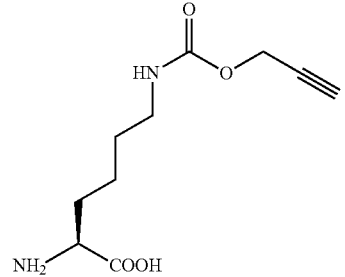

6

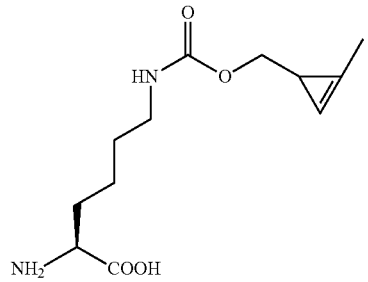

7

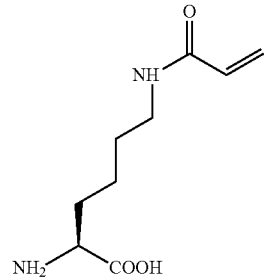

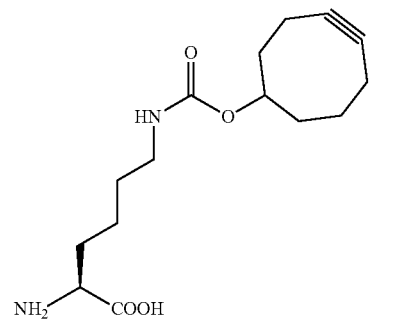
8
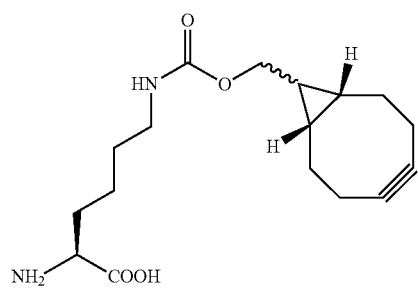
9
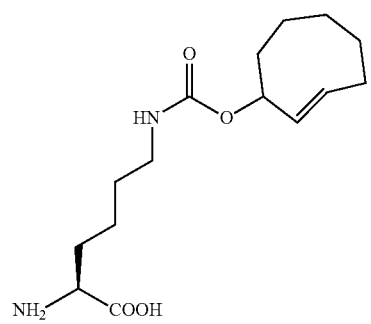
10
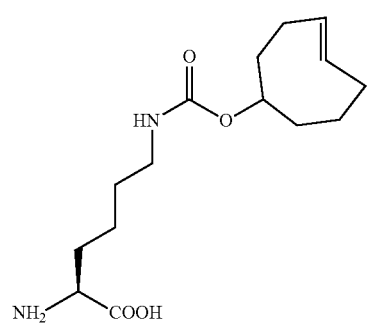
11
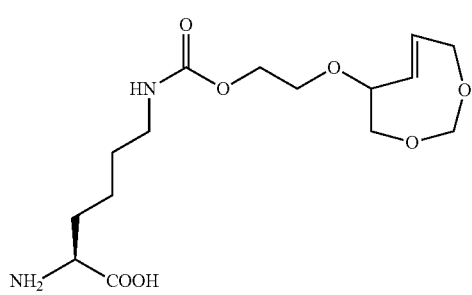
12
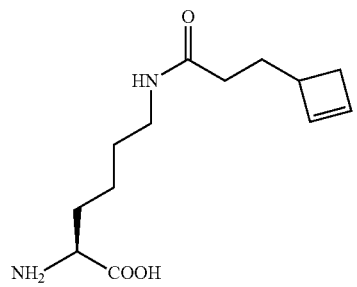
13
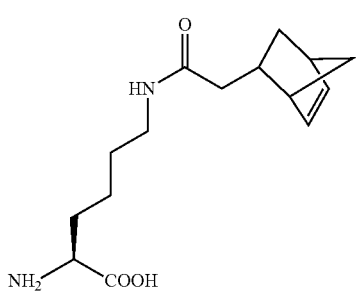
14
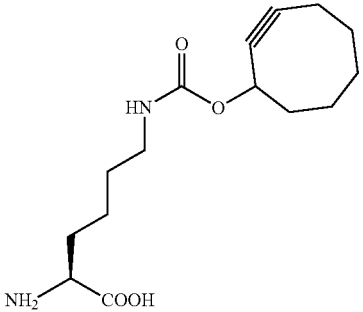
15
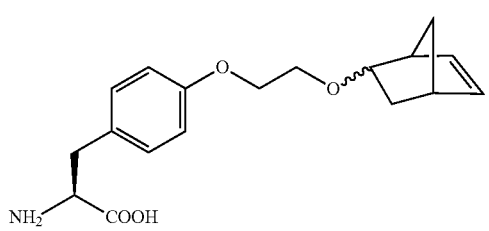
16
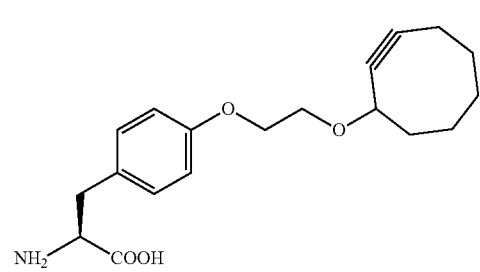
17

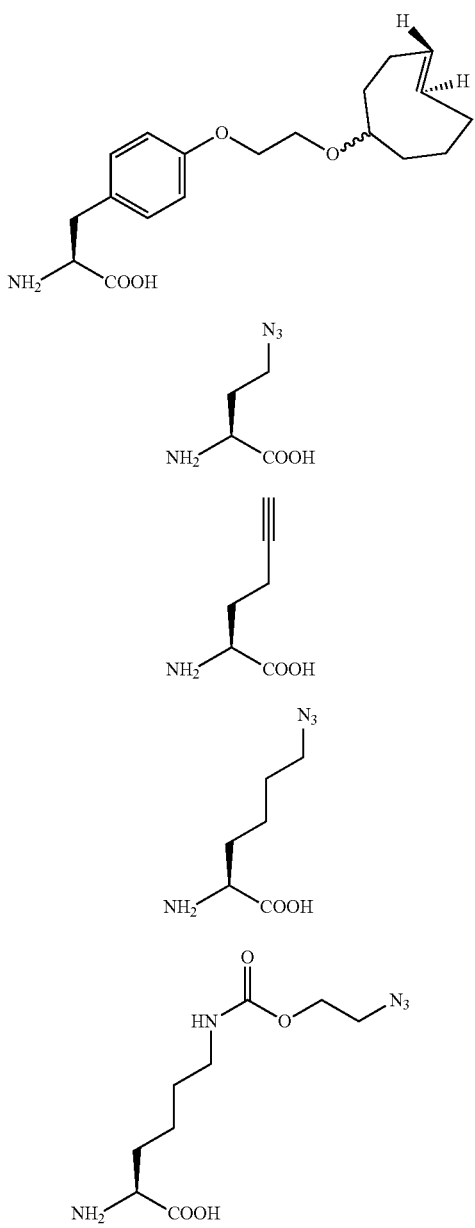

d. Fusion Proteins with Tag-Reactive Molecules

In embodiments of the present disclosure, the ligand is a fusion protein comprising a tag that is able to bind to their corresponding counterpart with high affinity, such as SNAP-tag, CLIP-tag, Halo Tag, Lumio Tag, and others known to those in the art.

Benzylguanine, benzylcytosine and chloroalkane are recognized by a "suicide" enzyme, such as SNAP. In the context of this invention, benzylguanine, or benzylcytosine may be optionally substituted to form derivatives of benzylguanine, or benzylcytosine. Benzylguanine derivatives or benzylcytosine derivatives are understood to mean a benzylguanine or benzylcytosine group, which is modified but which is nevertheless recognized by the suicide enzyme.

The tag molecule may be any molecule or biomolecule, which is capable of specifically binding to a further molecule. The examples may include SNAP-tag, CLIP-tag, Lumio-Tag, or Halo-Tag. For example, the affinity tag may be a SNAP-tag, a mutant of an alkylguanine-DNA alkyltransferase. Importantly, one of the substrates for SNAP-tag is benzylguanine. Commercially available products useful for the present invention include, e.g., HaloTag from Promega, Lumio Tag from Life Technologies, and SNAP/CLIP Tags from NEB.

Self-labeling protein tags are commercially available in various expression vectors. SNAP-tag is a 182 residues polypeptide (19.4 kDa) that can be fused to any protein of interest and further specifically and covalently tagged with a suitable ligand, such as a fluorescent dye. The SNAP-tag protein is an engineered version of the ubiquitous mammalian enzyme AGT, encoded in humans by the O-6-methylguanine-DNA methyltransferase (MGMT) gene. SNAP-tag was obtained using a directed evolution strategy, leading to a hAGT variant that accepts 06-benzylguanine derivatives instead of repairing alkylated guanine derivatives in damaged DNA.

CLIP-tag, was further engineered from SNAP-tag to accept 02-benzylcytosine derivatives as substrates, instead of 06-benzylguanine. A split-SNAP-tag version suitable for protein complementation assay and protein-protein interaction studies was later developed.

HaloTag is a self-labeling protein tag. It is a 297 residue peptide (33 kDa) derived from a bacterial enzyme, designed to covalently bind to a synthetic ligand. The HaloTag is a hydrolase, which has a genetically modified active site, which specifically binds the reactive chloroalkane linker and has an increased rate of ligand binding. The reaction that forms the bond between the protein tag and chloroalkane linker is fast and essentially irreversible under physiological conditions due to the terminal chlorine of the linker portion. In the aforementioned reaction, nucleophilic attack of the chloroalkane reactive linker causes displacement of the halogen with an amino acid residue, which results in the formation of a covalent alkyl-enzyme intermediate. This intermediate would then be hydrolyzed by an amino acid residue within the wild-type hydrolase. This would lead to regeneration of the enzyme following the reaction. However, in the modified haloalkane dehalogenase (HaloTag), the reaction intermediate cannot proceed through a subsequent reaction because it cannot be hydrolyzed due to the mutation in the enzyme. This causes the intermediate to persist as a stable covalent adduct with which there is no associated back reaction.

There are two steps to using this system: cloning and expression of the protein of interest as a SNAP-tag® fusion, and labeling of the fusion with the SNAP-tag substrate of choice. The SNAP-tag is a small protein based on human O6-alkylguanine-DNA-alkyltransferase (hAGT), a DNA repair protein. The SNAP-tag substrate in this case is the guanine leaving group connected to a benzyl linker. In the labeling reaction, the substituted benzyl group of the substrate is covalently attached to the SNAP-tag.

The SNAP-tag protein labeling system enables the specific, covalent attachment of virtually any molecule to a protein of interest.

e. Examples of Reactive Linkers

The following reactive linkers are suitable for use either as a capsid-reactive linker or as a ligand-reactive linker in accordance with various embodiments of the present disclosure.

45 a. TCO-PEG4-NHS

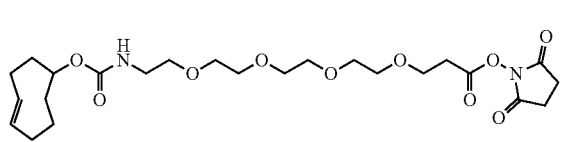 [SMILES: O=C(CCOCCOCCOCCOCCNC(=O)OC1CC/C=C/CCC1)ON1C(=O)CCC1=O]

Synonym(s): trans-Cyclooctene-PEG4-NHS; Empirical Formula (Hill Notation): C24H38N2O10; Molecular Weight: 514.57.

46 b. Tetrazine-PEG5-NHS

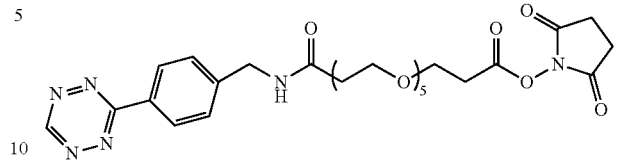

Tetrazine-PEG5-NHS Ester is an amine-reactive linker often used for modification of proteins, peptides, or amine-modified oligonucleotides with a tetrazine moiety.

c. Azido-PEG4-NHS

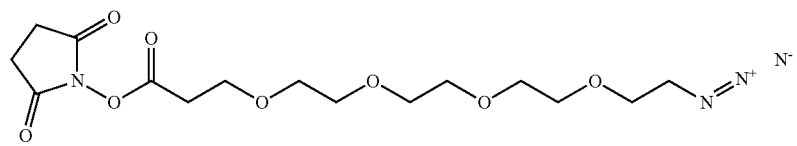

Also referred to as "Azide-PEG4-NHS" herein.

d. Phosphine-NHS

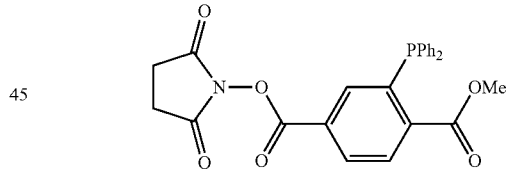

Molecular Weight: 461.40.

e. DBCO-PEG12-TFP Ester

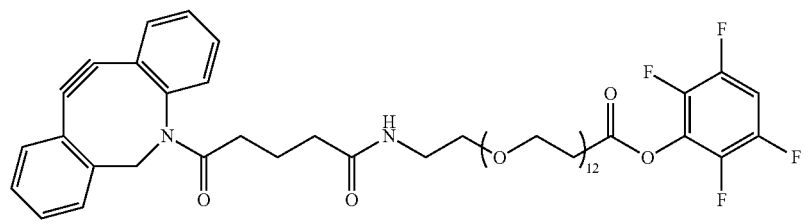

f. Maleimide-PEG8-Succinimidyl Ester

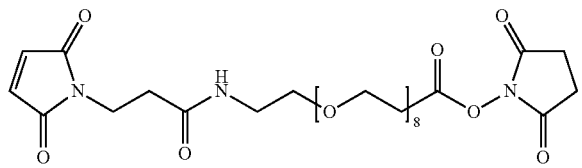

Maleimide PEG8 succinimidyl ester, 31-(2,5-Dihydro-2,5-dioxo-1H-pyrrol-1-yl)-29-oxo-4,7,10,13,16,19,22,25-octaoxa-28-azahentriacontanoic acid 2,5-dioxo-1-pyrrolidinyl ester, Maleimide-PEG8-NHS ester, 31-(2,5-Dihydro-2,5-dioxo-1H-pyrrol-1-yl)-29-oxo-4,7,10,13,16,19,22,25-octaoxa-28-azahentriacontanoic acid 2,5-dioxo-1-pyrrolidinyl ester, Maleimide-PEG8-NHS ester.

7.1.1. Surface Modified Viral Capsid of Formula I

In certain embodiments, the surface modified viral capsid is according to Formula I

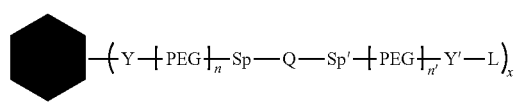 (I)

wherein:

In certain embodiments, the attachment moiety Y is formed by reaction between a capsid-reactive moiety and a capsid protein. In certain embodiments, the attachment moiety Y is formed by reaction between an NHS ester and a primary amino group of an amino acid of a capsid protein. In some embodiments, the amino group is the sidechain of a lysine present in the primary sequence of a capsid protein. In some embodiments, the amino group is a lysine present in the wild-type primary sequence of an AAV capsid protein.

In certain embodiments, the attachment moiety Y' is formed by reaction between a ligand-reactive moiety and a ligand. In certain embodiments, the attachment moiety Y' is formed by reaction between an NHS ester and an amino group of the ligand.

In certain embodiments, Q is a product formed by the reaction between members of a crosslinker reactive pair. In certain embodiments, Q is a crosslinked moiety formed by the reaction of DBCO and an azido group.

In certain embodiments, Q is selected from:

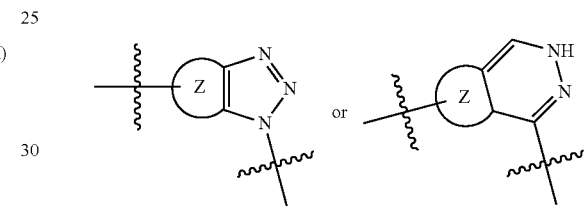

wherein, Z is a 7 or 8 membered cyclic or heterocyclic structure.

In certain embodiments, the surface modified viral capsid is according to Formula I-1:

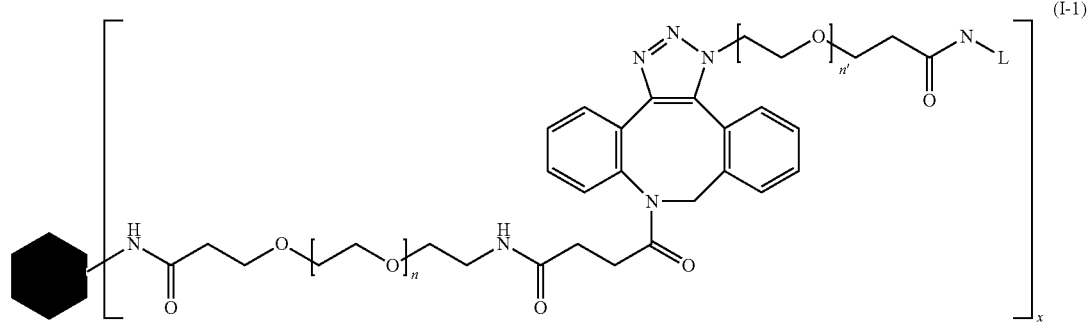 (I-1)

wherein:

is a viral capsid;
Y is an attachment moiety;
Y' is an attachment moiety;
Q is a crosslinked moiety;
PEG is a monomer of ethylene glycol;
n and n' are independently an integer from 0 to 100,
Sp and Sp' are independently an optional spacer;
L is a ligand; and
x is an integer from 1 to 300, from 100 to 200, from 120 to 180 or around 150.

is a viral capsid;

n and n' are independently an integer selected from 0 to 30;

L is a ligand; and x is an integer from 50 to 250.

In certain embodiments, n is an integer selected from 0 to 100. In certain embodiments, n is independently selected from 0, 1, 2, 3, 4, 5, 6, 7, 8, 9, 10, 11, 12, 13, 14, 15, 16, 17, 18, 19, 20, 25, 30, 35, 40, 45, 50, 75, and 100.

In certain embodiments, n' is an integer selected from 0 to 100. In certain embodiments, n' is selected from 0, 1, 2, 3, 4, 5, 6, 7, 8, 9, 10, 11, 12, 13, 14, 15, 16, 17, 18, 19, 20, 25, 30, 35, 40, 45, 50, 75, and 100.

f. Ligands

The ligand for use with the present disclosure is not particularly limited, as long as the ligand is amenable to conjugation to the viral capsid surface as described herein. In some embodiments, the ligand is selected from a protein ligand having a cognate that is located on the surface of mammalian cells, such as receptors. In some of these embodiments, the cognate protein is involved in transduction of the surface modified viral capsid.

In some embodiments, the ligand is a cell-type specific ligand. In certain embodiments, the ligand is selected from polypeptides, proteins, monosaccharides or polysaccharides, from steroid hormones, from RGD motif peptide, from vitamins, from small molecules or from targeting peptides. Also contemplated are antibodies (e.g., single chain) and nanobodies; enzymes such as proteases, glycosidases, lipases, peptidases; immunoglobulins such as CD47 (don't eat me signal); IgG proteases such as IdeZ and IdeS; protein based and small molecule adjuvants for vaccination.

According to one embodiment, a cell-type specific ligand is derived from proteins such as transferrin, Epidermal Growth Factor EGF, basic Fibroblast Growth Factor bFGF.

According to one embodiment, a cell-type specific ligand is derived from mono- or polysaccharides such as galactose, N-acetylgalactosamine and mannose.

According to one embodiment, a cell-type specific ligand is derived from vitamins such as folates.

According to one embodiment, a cell-type specific ligand is derived from small molecules including naproxen, ibuprofen or other known protein-binding molecules.

In certain embodiments, the ligand is selected from a protein ligand, such as a growth factor or a cytokine; a toxin subunit, such as a cholera toxin B subunit; a lectin, such as isolectin B4 or wheat germ agglutinin; an adhesion factor, such as lactadherin; an antibody or a single chain variable fragment thereof, such as an anti CD-34 antibody; more specifically, an *E. coli* recombinant scFv CD-34 antibody fragment, a peptide, such as deltorphin opioid receptor ligand; and a gene editing nuclease, such as Cas9.

g. Viral Capsids

In embodiments of the present disclosure, the viral capsid is not particularly limited. In some embodiments, the viral capsid is selected from non-enveloped viruses, such as adenovirus or adeno-associated virus. In some embodiments, the viral capsid is selected from an enveloped virus, such as retroviruses, lentiviruses, herpes simplex virus, and baculoviruses. Embodiments include non-naturally occurring capsids and includes a biologic or chemical alteration or variation of a naturally occurring capsid protein other than or in addition to a change in the primary amino acid sequence.

a. AAV

All recombinant adeno-associated viruses (rAAV, or AAV used interchangeably herein) may be implemented in the framework of the present disclosure. Such AAV particles are capable of transducing a wide range of post-mitotic cells in vivo in the mammal, e.g., (including but not limited to) muscle cells, hepatocytes and neurons.

In some embodiments, the AAV capsid comprises a VP1, VP2, and/or VP3 capsid protein of a naturally occurring AAV serotype. In some embodiments, the AAV comprises one or more of a non-naturally occurring VP1, VP2, and/or VP3 capsid protein. In certain of these embodiments, the non-naturally occurring VP1, VP2, or VP3 capsid protein differs in primary amino acid sequence from naturally occurring capsids. In certain embodiments, the non-naturally occurring capsid includes a biologic or chemical alteration or variation of a naturally occurring AAV capsid protein other than or in addition to a change in the primary amino acid sequence.

In various embodiments, the capsid proteins are those of an AAV1, AAV2, AAV3B, AAV5, AAV6, AAV8, or AAV9 naturally occurring AAV serotype. In various embodiments, the capsid protein is selected from capsid proteins disclosed in PCT/US2014/060163, U.S. Pat. No. 9,695,220, PCT/US2016/044819, PCT/US2018/032166, PCT/US2019/031851, and PCT/US2019/047546, which are incorporated herein by reference in their entireties.

The adeno-associated virus capsid may be chosen among all identified natural serotypes and in particular AAV2, AAV3b, AAV5, AAV8, AAV9 and AAV 10 and may be even more particularly AAV2.

Also, the adeno-associated virus may be chosen among synthetic serotypes generated by non-natural methods, such as, but not limited to: capsid mutagenesis, peptide insertions into, or deletions from, the capsid sequence, capsid shuffling from various serotypes or ancestral reconstruction.

The AAV capsids for use with the present disclosure are produced by any method known in the art, without limitation. For example, the AAV capsids can be produced by several methods including: transient transfection of HEK293 cells, stable cell lines infected with Ad or HSV, mammalian cells infected with Ad or HSV (expressing rep-cap and transgene) or insect cells infected with baculovirus vectors (expressing rep-cap and transgene). AAV capsids produced by any of these methods can be used to produce the surface functionalized and surface modified viral capsid described herein. In certain embodiments, the vectors are produced by transient transfection of HEK293 cells with calcium phosphate-HeBS method with two plasmids: pHelper, PDP2-KANA encoding AAV Rep2-Cap2 and adenovirus helper genes (E2A, VA RNA, and E4) and pVector ss-CAG-eGFP as illustrated in the provided Examples.

In some embodiments, the AAV capsid of the present disclosure comprises one or more sequences from extraviral origin, as desired.

In some embodiments, the capsid of AAV is composed of three overlapping capsid proteins (VP1, VP2, VP3) containing a unique VP1 N-terminus, a VP1/VP2 common portion and a portion which is common to VP1, VP2 and VP3.

In certain embodiments one or more capsid proteins comprise amino groups that are naturally occurring, that is the primary sequence corresponds to a wild-type capsid protein. In alternative embodiments, the primary sequence of one or more capsid proteins comprises amino acids that are engineered into a wild-type capsid protein sequence. In certain of these embodiments, the engineered amino acids include one or more amino groups present at the surface of the capsid and are involved in the surface functionalization of one or more capsid protein. In certain embodiments, the naturally occurring or engineered amino groups that are involved in surface functionalization of the capsid are selected from lysine, arginine and cysteine. In particular embodiments, the amino acid is lysine.

According to a particular embodiment, the AAV capsid comprises one or more wild-type capsid proteins from naturally occurring serotypes.

According to another particular embodiment, AAV capsid comprises a genetically modified capsid protein. In certain embodiments, the genetically modified capsid protein is a naturally occurring serotype engineered to comprise one or more genetic modifications (mutation, insertions or deletions). In an alternative embodiment, the rAAV capsid is composed of one or more of a synthetic capsid protein. In particular embodiments, the AAV capsid is engineered to modify the natural tropism, e.g., to reduce heparin binding.

In the framework of the present disclosure, a synthetic capsid includes any combination of capsid proteins from natural, genetically modified and artificially created (random mutations, sequence shuffling, in silico design, etc;) serotypes that are able to assemble and produce a new AAV virus capsid that is not known to exist in nature.

Currently, there are more than 100 AAV serotypes identified that differ in the binding capacity of capsid proteins to specific cell surface receptors that can transduce different cell types. AAV2 was the first serotype cloned into a bacterial plasmid and has since been used as a comparison to identify other serotypes. Twelve serotypes (AAV1, AAV2, AAV3, AAV4, AAV5, AAV6, AAV7, AAV8, AAV9, AAV10, AAV11, and AAV12) have been tested thoroughly for their ability to transduce specific cell types and differentiated between capsid protein motifs that bind specific cell surface receptors for cell attachment. In the context of this invention, an AAV capsid is selected from AAV1, AAV2, AAV3, AAV4, AAV5, AAV6, AAV7, AAV8, AAV9, AAV10, AAV11, AAV12 is preferred. However, it should be understood that any other AAV capsid can be used in the context of the present invention.

In one embodiment, the adeno associated virus (AAV) particle of the present invention is selected from AAV1, AAV2, AAV3, AAV4, AAV5, AAV6, AAV7, AAV8, AAV9, AAV10, AAV11, and AAV12. The most commonly used gene transfer systems to date are derivatives of viruses, e.g., adeno-associated virus type 2 (AAV2), AAV9, and AAV8. In particular embodiments, the rAAV capsid. AAV-2 and AAV-9, where the capsid proteins are optionally further engineered to reduce or modify native tropism, e.g., to reduce heparin binding.

b. Removal of Natural Binding Moiety

In particular embodiments, of the adeno associated virus (rAAV) capsid of the present disclosure, the rAAV is selected from a naturally occurring serotype having a natural cell binding site that enables binding to heparan sulfate proteoglycans that has been removed.

In particular embodiments, removal of the heparin binding has been engineered by replacing at least one of arginine 585 or arginine 588 of VP1 and/or an analogous arginine in VP2 or VP3 with a different amino acid, such as alanine. In some embodiments, at least one of arginine 448 and arginine 451 in VP2 or 383 and 386 in VP3 is altered.

In particular embodiments, the adeno associated virus (AAV) capsid of the present disclosure is comprised of at least one protein that is mutated from wild-type, e.g., wherein the engineered/mutated protein is selected from wild-type protein is VP1, VP2, and/or VP3. Alternatively, two of the proteins VP1, VP2 and/or VP3 in said capsid are mutated, or all three of the proteins VP1, VP2 and VP3 in said capsid are modified. In particular embodiments, at least one part, e.g., one amino acid, of the at least one of the proteins to be modified in said capsid is mutated (replaced, inserted or deleted). However, it is also possible to mutate multiple parts of the proteins VP1, VP2 and VP3 in said capsid, e.g. multiple amino acids, such as 2, 3, 4, 5, 6, 7, 8, 9, 10, or any other number of parts or amino acids. In particular embodiments, at least one of arginines 484, 487, 585 and 588 and lysine 532 of VP1, and/or an analogous arginine in VP2 or VP3, are removed by replacing them with a different amino acid, such as alanine.

7.1.1. PEG Immune Cloaking

According to another particular embodiment, the viral capsid surface may be modified according to methods known in the art to comprise a steric shielding agent for avoiding interaction with neutralizing antibodies. In some embodiments, the steric shielding agent is derived from synthetic polymers such as polyethylene glycol (PEG) or pHPMA. Polymers of PEG are prepared by polymerization processes and comprise a heterogeneous mixture of sizes and molecular weights that may be characterized by a Poisson distribution of chain lengths and molecular weights, also known as the polydispersity index (PDI), dispersity index or simply dispersity (indicated by the symbol "•"). The reported molecular weight is an average molecular weight, and • (or PDI) gives an indication of the range of molecular weights in the sample.

h. Capsid Cargo

The nucleic acid cargo packaged inside the surface modified rAAV capsid of the present invention can be any kind of nucleic acid molecule usefully transduced into cells by rAAV.

In some embodiments, the payload or cargo of the rAAV capsid is an expressible polynucleotide. In certain embodiments, the expressible polynucleotide encodes a protein (e.g., encoding a therapeutic protein). In certain embodiments, the expressible polynucleotide encodes a transgene. In certain embodiments, the expressible polynucleotide can be transcribed to provide a guide RNA, a trans-activating CRISPR RNA (tracrRNA), a messenger RNA (mRNA), a microRNA (miRNA), or a shRNA.

In some embodiments, the payload provides a DNA homology construct for homology directed repair.

In some embodiments, said nucleic acid molecule is encoding intracellular antibodies (for example to neutralize certain proteins inside cells), nucleic acid molecules encoding peptide toxins (for example to block ion channels in the pain pathway), nucleic acid molecules encoding optogenetic actuators (for example to turn on or turn off neuronal activity using light), nucleic acid molecules encoding pharmacogenetic tools (for example to turn on or off neuronal signaling using chemical ligands that have no interfering pharmacological effect), nucleic acid molecules encoding CRISPR based-editors for precision gene editing, nucleic acid molecules encoding CRISPR-epigenetic tools to regulate gene expression, and/or nucleic acid molecules encoding suicide genes to induce cell death.

Preferably, when the cargo comprises a gene editing nuclease, such as Cas9, the cargo further comprises a nucleic acid molecule, such as a gRNA and/or a specific DNA to be inserted into a host genome. In certain of these embodiments, the cargo comprises a transgene known to be associated with a genetic disorder.

The person of skill is aware of other gene editing nucleases, apart from Cas9, such as Cpf1, TALEN, ZFN, or a homing endonuclease. Further, it may be convenient to engineer using DNA-guided Argonaute interference systems (DAIS). Basically, said Argonaute (Ago) protein is heterologously expressed from a polynucleotide introduced into said cell in the presence of at least one exogenous oligonucleotide (DNA guide) providing specificity of cleavage to said Ago protein to a preselected locus. The TALEN and Cas9 systems are respectively described in WO 2013/176915 and WO 2014/191128. The Zinc-finger nucleases (ZFNs) are initially described in Kim, Y G; Cha, J.; Chandrasegaran, S. ("Hybrid restriction enzymes: zinc finger fusions to Fok I cleavage domain" (1996). Proc Natl Acad Sci USA 93 (3): 1156-60). Cpf1 is a class 2 CRISPR Cas System described by Zhang et al. (Cpf1 is a single RNA-guided Endonuclease of a Class 2 CRISPR-Cas System. (2015). Cell; 163:759-771). The argonaute (AGO) gene family was initially described in Guo S, Kemphues K J. (Par-1, a gene required for establishing polarity in *C. elegans* embryos, encodes a putative Ser/Thr kinase that is asymmetrically distributed. (1995). Cell; 81(4):611-20).

d. Methods of Making Surface Modified Viral Capsids

Another aspect of this disclosure relates to a method of producing a surface-modified recombinant viral capsid. In certain embodiments, the provided capsid is for use in transducing nucleic acids into eukaryotic, typically mammalian, particularly human, cells. In some embodiments, the surface-modified viral capsid is a recombinant adenoviral virion. In some embodiments, the surface-modified viral capsid is a recombinant AAV virion.

The method comprises the step of crosslinking, i.e., covalently conjugating, a ligand to a viral capsid protein via a linker comprising a crosslinked moiety, Q. Preferably, the ligand introduces at least one mammalian cell surface target binding site into said capsid, optionally wherein a natural cell surface target binding site in said capsid is removed, such as is previously removed.

In one embodiment, a method of a making a surface modified viral capsid described herein, the comprises the steps:
 i) obtaining a surface functionalized viral capsid by reacting a viral capsid protein with a capsid-reactive linker comprising a first member of a crosslinker reactive pair and optionally one or more of a spacer;
 ii) conjugating the surface functionalized viral capsid with a functionalized ligand comprising a second member of the crosslinker reactive pair and optionally one or more of a spacer,
 wherein the first and second members of the crosslinker reactive pair react to form a crosslinked moiety, Q; and
 iii) obtaining the surface modified viral capsid.

As mentioned above, if said natural mammalian cell surface target binding site in said capsid is present and not removed, and the capsid is surface modified to comprise at least one ligand according to the present disclosure, the provided surface modified viral capsid has a higher infectivity rate (i.e., improved transduction—greater efficiency or similar efficiency at lower titer), compared to the capsid that has not been surface modified as described herein. In alternative embodiments, if said natural mammalian cell target binding site in said capsid is removed, (e.g., genetic modification of the known heparin binding site) prior to surface modification of the capsid to comprise a ligand, the provided surface modified capsid has one or more of i) modified tropism and ii) improved transduction compared to the capsid that has not been surface modified as described herein.

The adeno associated virus (AAV) particle produced by the above method is preferably selected from AAV1, AAV2, AAV3, AAV4, AAV5, AAV6, AAV7, AAV8, AAV9, AAV10, AAV11, AAV12, hu68, rh.10, and mixtures thereof.

Any of the proteins of the adeno associated virus (AAV) particle to be produced by the above method can be modified. Preferably, at least one of the proteins VP1, VP2 or VP3 in said capsid is modified in the above method. Alternatively, two of the proteins VP1, VP2 and/or VP3 in said capsid are modified, or all three of the proteins VP1, VP2 and VP3 in said capsid are modified. Preferably, at least one part, e.g. at least one amino acid, of the at least one of the proteins to be modified in said capsid is modified. However, it is also possible to modify multiple parts of the proteins VP1, VP2 and VP3 in said capsid, e.g. multiple amino acids, such as 2, 3, 4, 5, 6, 7, 8, 9, 10, or any other number of parts or amino acids. Preferably at least one of arginines 484, 487, 585 and 588 and lysine 532 of VP1 and/or an analogous arginine in VP2 or VP3 are removed by replacing them with a different amino acid, such as alanine.

A capsid protein from a natural AAV serotype (further genetically modified if desired), such as VP1, VP2 or VP3, are modified chemically at specific amino acids. Examples for such modifications are well known in the art and are summarized e.g., in R. Lundblad, Chemical Reagents for Protein Modification, 3rd ed. CRC Press, 2005, which is incorporated herein by reference. Chemical modification of amino acids includes but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols in Protein Science, Eds. Coligan et al. (John Wiley & Sons NY 1995-2000, the entire contents of which are expressly incorporated herein) for more extensive methodology relating to chemical modification of proteins.

In some embodiments of the above method for producing an improved adeno associated virus (AAV), the capsid modification comprises both removing of natural binding sites and introducing of ligand binding sites, e.g., via functionalizing of the surface of the capsid with a capsid surface reactive moiety. In certain other embodiments, the natural binding site of the AAV capsid is unchanged, i.e. not be removed, and at least one ligand binding site or ligand is introduced in accordance with the present disclosure.

In some embodiments the natural binding site is removed by the above method for producing an improved adeno associated virus (AAV) particle, wherein the natural binding site enables binding to heparan sulfate proteoglycans. In certain of these embodiments, the natural binding site is removed by replacing at least one of arginines 585 and 588 of VP1 and/or an analogous arginine in VP2 or VP3 with a different amino acid, such as alanine.

In some embodiments the ligand binding site as introduced in accordance with the present disclosure is one that enables the covalent attachment of ligands. In certain of these embodiments the ligand binding site is selected from a benzylguanine group that is attached to available lysine residues, more preferably by reacting said capsid with benzylguanine N-hydroxysuccinimide (BG-NHS), and/or benzylcytosine N-hydroxysuccinimide (BC-NHS).

The present invention preferably utilizes tags that are able to bind to their specific ligands with high affinity, such as SNAP-tag, CLIP-tag, Halo-Tag, Lumio-Tag, and others. The tag molecule as introduced in the above-method may be any molecule or biomolecule, which is capable of specifically binding to a further molecule. The examples may include SNAP-tag, CLIP-tag, Lumio-Tag, or Halo-Tag. For example, the affinity tag may be a SNAP-tag, a mutant of an alkylguanine-DNA alkyltransferase. Importantly, one of the substrates for SNAP-tag is benzylguanine. Commercially available products useful for the present invention include, e.g., HaloTag from Promega, Lumio Tag from Life Technologies, and SNAP/CLIP Tags from NEB. Said ligand binding site as introduced is preferably attached to the epsilon-amino group or the primary amine of said available lysine residue.

Accordingly, the above method for producing an improved adeno associated virus (AAV) particle is further preferred, wherein said method further comprises the step of attaching a ligand to said benzylguanine and/or said benzylcytosine group, in particular a HaloTag™, a SNAP-tag™ or a CLIP-tag™.

Said ligand to be attached can be any kind of ligand, but is preferably selected from a protein ligand, such as a growth factor or a cytokine; a toxin subunit, such as a cholera toxin B subunit; a lectin, such as isolectin B4 or wheat germ agglutinin; an adhesion factor, such as lactadherin; an antibody, such as an anti CD-34 antibody; a peptide, such as deltorphin opioid receptor ligand; and a gene editing nuclease, such as Cas9.

e. Formulations

Yet another embodiment of the invention pertains to the afore-described surface modified viral capsid for use in the treatment of a disease, wherein said AAV is administered to a subject in a liquid, dry or semi-solid form, such as, for example, in the form of a tablet, coated tablet, effervescent tablet, capsule, powder, granulate, sugar-coated tablet, lozenge, pill, ampoule, drop, suppository, emulsion, ointment, gel, tincture, paste, cream, moist compress, gargling solution, plant juice, nasal agent, inhalation mixture, aerosol, mouthwash, mouth spray, nose spray, or room spray.

In certain embodiments, a pharmaceutical composition is provided comprising a recombinant virion, the recombinant virion comprising a surface modified viral capsid as provided herein with a recombinant nucleic acid cargo contained therein, the pharmaceutical composition further comprising a pharmaceutically acceptable carrier, diluents, solubilizer, filler, preservative and/or excipient. Such pharmaceutically acceptable carrier, diluents, solubilizer, filler, preservative and/or excipient may for instance be found in Remington: The Science and Practice of Pharmacy, 20th Edition. Baltimore, MD: Lippincott Williams & Wilkins, 2000.

A further aspect of the present invention then relates to a pharmaceutical composition, comprising the surface modified viral capsid according to the present invention, together with at least one pharmaceutically acceptable carrier and/or diluent, i.e. in combination with pharmaceutically acceptable additives, carriers, diluents, solvents, filters, lubricants, excipients, binders or stabilizers. Preferably, said composition is administered to said subject in form of sprays, coatings, foams, lotions, gels, mouthwash, oral formulations or injections. Said composition can be administered to said subject systemically, orally or by any other clinically/medically accepted method.

A further aspect of the present invention then relates to a kit comprising: a) the surface modified viral capsid as disclosed and/or for use according to the present disclosure, or a pharmaceutical composition comprising the surface modified viral capsid as disclosed according to the present disclosure, b) written instructions to apply said surface modified viral capsid or said pharmaceutical composition to a target said; and optionally, a container holding the surface modified viral capsid for use or the composition and the written instructions.

Another aspect of the present invention relates to the use of the above-described kit for preventing, treating, and/or inhibiting a viral infection in a subject in need of said treatment.

f. Methods of Treating Disease

The present disclosure also includes a method for treating a subject at risk for development and/or progression of a disease, including a monogenic or polygenic genetic disease, wherein a therapeutically effective amount of the AAV particle as provided by the present disclosure is administered to the patient. In this context, therapeutically effective describes an amount of AAV particles sufficient to treat the disease, such as a genetic disease, by resolution of symptoms. Therapeutically effective can also be an amount sufficient to prevent symptoms of a disease, such as a genetic disease, from occurring. Being at risk for the disease can result from, e.g., genetic and/or phenotypic symptoms, which predispose to the disease. In some embodiments, a patient at risk for a genetic disease has been determined to carry or be deficient in a gene associated with a genetic disease.

A further aspect of this disclosure then relates to a method for treating a disease that can be treated by gene therapy, the method comprising administering the surface modified viral capsid according to the present disclosure to a subject in need thereof.

Cells and/or subjects to be treated with the surface modified viral capsids of this invention are preferably of mammalian origin, such as of human origin. Nevertheless, the present invention can advantageously be used also in veterinary medicine, cell culture procedures, or even in plant cell diseases, depending on the similarities of the mechanisms of entry into the cells. In some embodiments, said cell to be treated is a mammalian cell, a prokaryotic cell, or a plant cell. In particular embodiments, said cell to be treated is a human cell.

Yet another embodiment of the invention pertains to the afore-described method for treating a disease, comprising administering the surface modified viral capsid according to the present disclosure to a subject in need thereof, wherein said surface modified viral capsid is administered to a subject in a liquid, dry or semi-solid form, such as, for example, in the form of a tablet, coated tablet, effervescent tablet, capsule, powder, granulate, sugar-coated tablet, lozenge, pill, ampoule, drop, suppository, emulsion, ointment, gel, tincture, paste, cream, moist compress, gargling solution, plant juice, nasal agent, inhalation mixture, aerosol, mouthwash, mouth spray, nose spray, or room spray.

The disease to be treated by the above method for treating a disease that comprises administering the surface modified viral capsid to a subject. In certain embodiments, the disease selected from cancer, an inherited monogenic disease, such as inherited retinal disease, a genetic skin disease, such as Olmsted Syndrome or Familiar Primary Localized Cutaneous Amyloidosis, an infectious disease, adrenoleukodystrophy, alpha•1 antitrypsin deficiency, aromatic L•amino acid deficiency, Batten disease, Becker muscular dystrophy, beta thalassemia, Canavan disease, chronic granulomatous disease, Crigler-Najjar syndrome, cystic fibrosis, Duchenne muscular dystrophy, Fabry disease, familial adenomatous polyposis, familial hypercholesterolemia, familial lecithin•cholesterol acyltransferase deficiency, Fanconi anemia, galactosialidosis, Gaucher's disease, gyrate atrophy, hemophilia A, hemophilia B, Hurler syndrome (mucopolysaccharidosis type I), Hunter syndrome (mucopolysaccharidosis type II), Huntington's chorea, junctional epidermolysis bullosa, late infantile neuronal ceroid lipofuscinosis, leukocyte adherence deficiency, limb girdle muscular dystrophy, lipoprotein lipase deficiency, metachromatic leukodystrophy, Sly syndrome (mucopolysaccharidosis type VII), Netherton syndrome, ornithine transcarbamylase deficiency, Pompe disease, purine nucleoside phosphorylase deficiency, recessive dystrophic epidermolysis bullosa, sanfilippo A (mucopolysaccharidosis type IIIA), sanfilippo B (mucopolysaccharidosis type IIIB), sickle cell disease, severe combined immunodeficiency, spinal muscular atrophy, Tay Sachs disease, Wiskott-Aldrich syndrome, von Gierke disease (glycogen storage disease type Ia), X•linked myotubular myopathy, anemia of end stage renal disease, angina pectoris (stable, unstable, refractory), coronary artery stenosis, critical limb ischemia, heart failure, intermittent claudication, myocardial ischemia, peripheral vascular disease, pulmonary hypertension, venous ulcers, adenovinis infection, cytomegalovirus infection, Epstein-Barr virus infection, hepatitis B infection, hepatitis C infection, HIV/AIDS, influenza, Japanese encephalitis, malaria, pediatric respiratory disease, respiratory syncytial virus, tetanus, tuberculosis, gynecological cancer, breast cancer, ovary cancer, cervix cancer, vulva cancer, nervous system cancer, glioblastoma, leptomeningeal carcinomatosis, glioma, astrocytoma, neuroblastoma, retinoblastoma, gastrointestinal cancer, colon, colorectal, liver metastases, post•hepatitis liver cancer, pancreas, gall bladder, hepatocellular carcinoma, genitourinary cancer, prostate, renal, bladder, anogenital neoplasia, skin cancer, melanoma (malignant/metastatic), head and neck cancer, nasopharyngeal carcinoma, squamous cell carcinoma, esophageal cancer, lung cancer, adenocarcinoma, small cell/nonsmall cell, mesothelioma, hematological cancer, leukemia, lymphoma, multiple myeloma, sarcoma, germ cell cancer, Li•Fraumeni syndrome, thyroid cancer, Alzheimer's disease, amyotrophic lateral sclerosis, carpal tunnel syndrome, chronic traumatic brain injury, cubital tunnel syndrome, diabetic neuropathy, epilepsy, giant axonal neuropathy, late infantile neuronal ceroid lipofuscinosis, multiple sclerosis, myasthenia gravis, pain, Parkinson disease, peripheral neuropathy, spinal muscular atrophy type 2, achromatopsia, age•related macular degeneration, choroideraemia, diabetic macular edema, glaucoma, Leber congenital amaurosis, macular telangiectasia type 2, retinitis pigmentosa, superficial corneal opacity, X•linked retinoschisis, arthritis (rheumatoid, inflammatory, degenerative), degenerative joint disease, severe inflammatory disease of the rectum, ulcerative colitis, chronic renal disease, diabetic ulcer, foot ulcer, detrusor overactivity, erectile dysfunction, fractures, hearing loss, hereditary inclusion body myopathy, graft versus host disease/transplant patients, oral mucositis, parotid salivary hypofunction, systemic scleoderma, type I diabetes, and wound healing, or combinations thereof.

Also provided is a method for treating a disease, comprising administering the surface modified viral capsid according to the present disclosure to a subject in need thereof, wherein said surface modified viral capsid is administered to said subject or to a cell, in the form of a pharmaceutical composition, e.g., in combination with pharmaceutically acceptable additives, carriers, diluents, solvents, filters, lubricants, excipients, binders or stabilizers. In certain embodiments, said composition is administered to said subject in form of sprays, coatings, foams, lotions, gels, mouthwash, oral formulations or injections. Said composition can be administered to said subject systemically, orally or by any other clinically/medically accepted method.

Yet another aspect of this invention relates to the surface modified viral capsid according to the present disclosure for use in the transfection of a cell, for example as a gene delivery tool in research. Said use can also be for cosmetic purposes, and the present invention includes a method for cosmetic treatment in analogy to the medical treatment as disclosed herein. For this, administering the surface modified viral capsid according to the present disclosure to a subject or to a cell can be also achieved in form of a cosmetic composition, e.g. in combination with cosmetically safe and acceptable additives, carriers, diluents, solvents, filters, lubricants, excipients, binders or stabilizers. In certain embodiments, said composition is administered to said subject in form of sprays, coatings, foams, lotions, gels, mouthwash, oral formulations or injections. Said composition can be administered to said subject systemically, orally or by any other clinically/cosmetically accepted method.

The person of skill is aware of methods of using vectors derived from AAV for transferring genes in vitro and in vivo, such as those that have been described in WO 93/09239, U.S. Pat. Nos. 4,797,368, 5,139,941 and EP 488 528.

An additional aspect of the present invention relates to a kit comprising: a) the surface modified viral capsid for the transfection of cells, b) written instructions to use the surface modified viral capsid for the transfection of cells; and optionally, a container holding the surface modified viral capsid and the written instructions.

a. Indications

Another aspect of this invention relates to recombinant virions comprising surface modified viral capsid according to the present invention for use in the treatment of a disease, and methods of treating disease by administering an effective amount of recombinant virions comprising surface modified capsid as described herein. In certain embodiments, the compositions provided herein are for use in a treatment comprising gene therapy. Furthermore, the invention provides for the use of the surface modified viral capsid composition for the preparation of a medicament for gene therapy. Also, the invention provides for a method of treatment comprising gene therapy, wherein the method comprises the administration of the surface modified viral capsid composition.

The kind of disease that can be treated or prevented by the surface modified viral capsid for use according to the present invention is not particularly limited. Diseases to be treated or prevented by the surface modified viral capsid for use according to the present invention include those diseases that can be treated by gene therapy, such as cancer, an inherited monogenic disease, such as inherited retinal disease, a genetic skin disease, such as Olmsted Syndrome or Familiar Primary Localized Cutaneous Amyloidosis, an infectious disease, ataxia, adrenoleukodystrophy, alpha•1 antitrypsin deficiency, aromatic L•amino acid deficiency, Batten disease, Becker muscular dystrophy, beta thalassemia, Canavan disease, chronic granulomatous disease, Crigler-Najjar syndrome, cystic fibrosis, Duchenne muscular dystrophy, Fabry disease, familial adenomatous polyposis, familial hypercholesterolaemia, familial lecithin•cholesterol acyltransferase deficiency, Fanconi anaemia, galactosialidosis, Gaucher's disease, gyrate atrophy, hemophilia A and B, Hurler syndrome (mucopolysaccharidosis type I), Hunter syndrome (mucopolysaccharidosis type II), Huntington's chorea, junctional epidermolysis bullosa, late infantile neuronal ceroid lipofuscinosis, leukocyte adherence deficiency, limb girdle muscular dystrophy, lipoprotein lipase deficiency, metachromatic leukodystrophy, Sly syndrome (mucopolysaccharidosis type VII), Netherton syndrome, ornithine transcarbamylase deficiency, Pompe disease, purine nucleoside phosphorylase deficiency, recessive dystrophic epidermolysis bullosa, sanfilippo A (mucopolysaccharidosis type IIIA), sanfilippo B (mucopolysaccharidosis type IIIB), sickle cell disease, severe combined immunodeficiency, spinal muscular atrophy, Tay Sachs disease, Wiskott-Aldrich syndrome, von Gierke disease (glycogen storage disease type Ia), X•linked myotubular myopathy, anemia of end stage renal disease, angina pectoris (stable, unstable, refractory), coronary artery stenosis, critical limb ischemia, heart failure, intermittent claudication, myocardial ischemia, peripheral vascular disease, pulmonary hypertension, venous ulcers, adenovirus infection, cytomegalovirus infection, Epstein-Barr virus infection, hepatitis B infection, hepatitis C infection, HIV/AIDS, influenza, Japanese encephalitis, malaria, pediatric respiratory disease, respiratory syncytial virus, tetanus, tuberculosis, gynaecological cancer, breast, ovary, cervix, vulva, nervous system cancer, glioblastoma, leptomeningeal carcinomatosis, glioma, astrocytoma, neuroblastoma, retinoblastoma, gastrointestinal cancer, colon, colorectal, liver metastases, post•hepatitis liver cancer, pancreas, gall bladder, hepatocellular carcinoma, genitourinary cancer, prostate, renal, bladder, ano•genital neoplasia, skin cancer, melanoma (malignant/metastatic), head and neck cancer, nasopharyngeal carcinoma, squamous cell carcinoma, esophageal cancer, lung cancer, adenocarcinoma, small cell/non•small cell, mesothelioma, hematological cancer, leukemia, lymphoma, multiple myeloma, sarcoma, germ cell cancer, Li•Fraumeni syndrome, thyroid cancer, Alzheimer's disease, amyotrophic lateral sclerosis, carpal tunnel syndrome, chronic traumatic brain injury, cubital tunnel syndrome, diabetic neuropathy, epilepsy, giant axonal neuropathy, late infantile neuronal ceroid lipofuscinosis, multiple sclerosis, myasthenia gravis, pain, Parkinson disease, peripheral neuropathy, spinal muscular atrophy type 2, achromatopsia, age•related macular degeneration, choroideraemia, diabetic macular oedema, glaucoma, Leber congenital amaurosis, macular telangiectasia type 2, retinitis pigmentosa, superficial corneal opacity, X•linked retinoschisis, arthritis (rheumatoid, inflammatory, degenerative), degenerative joint disease, severe inflammatory disease of the rectum, ulcerative colitis, chronic renal disease, diabetic ulcer/foot ulcer, detrusor overactivity, erectile dysfunction, fractures, hearing loss, hereditary inclusion body myopathy, graft versus host disease/transplant patients, oral mucositis, parotid salivary hypofunction, systemic scleroderma, type I diabetes, and/or wound healing.

In certain embodiments, the ataxia to be treated in accordance with the present disclosure is ataxia associated with a hereditary disorder consisting of degeneration of the cerebellum or of the spine and may present with overlapping cerebellar and sensory ataxia, even. Hereditary disorders causing ataxia include autosomal dominant ones such as spinocerebellar ataxia, episodic ataxia, and dentatorubropallidoluysian atrophy, as well as autosomal recessive disorders such as Friedreich's ataxia (sensory and cerebellar, with the former predominating) and Niemann Pick disease, ataxia-telangiectasia (sensory and cerebellar, with the latter predominating), and abetalipoproteinaemia. An example of X-linked ataxic condition is the rare fragile X-associated tremor/ataxia syndrome or FXTAS.

In certain embodiments, the indication to be treated is lipoprotein lipase deficiency, large B-cell lymphoma, beta thalassemia, mantle cell lymphoma, vascular endothelial growth factor peripheral artery disease, head and neck squamous cell carcinoma, spinal muscular atrophy, adenosine deaminase deficiency (ADA-SCID), melanoma in patients who have recurring skin lesions, B cell lymphoblastic leukemia, or Leber congenital amaurosis.

In certain embodiments, the indication to be treated include Charcot-Marie-Tooth (all types), Gangliosidosis (all types), Genetic epilepsy (i.e. Dravet), tuberous sclerosis complex, Spinal cord injury, all demyelinating hereditary motor and sensory neuropathies (HMSN), Krabbe disease, fibrodysplasia ossificans progressive, Neurofibromatosis 1 and 2, essential tremor, fragile X syndrome, Lesch-Nyhan syndrome, myotonic dystrophy, multiple system atrophy (MSA), Zellweger syndrome, neuromyelitis optica, or Devic's disease, central pontine myelinolysis, myelopathies such as tabes dorsalis (syphilitic myelopathy), leukoencephalopathies such as progressive multifocal leukoencephalopathy, leukodystrophies, and Guillain-Barré syndrome and its chronic counterpart, chronic inflammatory demyelinating polyneuropathy.

In certain embodiments, the indication to be treated is anti-MAG peripheral neuropathy, or copper deficiency-associated conditions (peripheral neuropathy, myelopathy, and rarely optic neuropathy), or progressive inflammatory neuropathy.

b. Modes of Administration

Another aspect of this invention relates to modes of administration of the surface modified viral capsid according to the present invention for use in the treatment of a disease.

In some embodiments, the surface modified viral capsid according to the present invention may be directly or indirectly administered using suitable means known in the art. Methods and uses of the invention include delivery and administration of the surface modified viral capsid according to the present invention composition systemically, regionally or locally, or by any route, for example, by injection, infusion, orally (e.g., ingestion or inhalation), or topically (e.g., transdermally). Exemplary administration and delivery routes include intravenous (i.v.), intra-articular, intraperitoneal (i.p.), intra-arterial, intramuscular, parenteral, subcutaneous, intra-pleural, topical, dermal, intradermal, transdermal, parenterally, e.g., transmucosal, intra-cranial, intraspinal, oral (alimentary), mucosal, respiration, intranasal, intubation, intrapulmonary, intrapulmonary instillation, buccal, sublingual, intravascular, intrathecal, intracavity, iontophoretic, intraocular, ophthalmic, optical, intraglandular, intraorgan, intralymphatic, intrathecal, intra cisterna magna. Improvements in means for providing an individual or a cell, tissue, organ of said individual with the surface modified viral capsid according to the present invention composition are anticipated considering the progress that has already thus far been achieved. Such future improvements may of course be incorporated to achieve the mentioned effect of the invention. In certain embodiments, the step of administering the surface modified viral capsid according to the present invention, the capsid composition is dissolved in a solution that is compatible with the delivery method. In certain embodiments formulation for intravenous, subcutaneous, intramuscular, intrathecal, intraarticular and/or intraventricular administration, is the capsid composition is formulated as a physiological salt solution.

g. Examples

Summary of Experimental Observations

Recombinant adeno-associated virus (rAAV) has emerged as the in vivo gene delivery vector of choice, both in basic research and for clinical use. Recombinant AAV vectors do not undergo site-specific integration in the host genome, and this, coupled with modest immunogenicity, renders them one of the safest strategies for gene therapy (Naso M F, Tomkowicz B, Perry W L, 3rd, Strohl W R. Adeno-Associated Virus (AAV) as a Vector for Gene Therapy. *BioDrugs* 2017; 31:317-34). Despite their clear advantages over other viral vectors for in vivo use, AAVs still have some limitations. For example, they are ineffective at transducing some cell types; as a result, high titers are often required for efficient gene transfer. This in turn leads to off-target effects through transduction of inappropriate cell types, raises production costs substantially, and leads to toxicity.

Efforts to improve AAV mediated gene delivery initially focused on exploiting wildtype serotypes that display distinct tropism for different cell types. By generating pseudotyped AAV containing transgenes flanked by ITRs from serotype 2, and capsids from other wildtype serotypes, the transduction specificity of the recombinant vector can be modified. More recently, synthetic AAV capsids have been engineered, which contain capsid proteins derived from directed evolution or rational design (Colella P, Ronzitti G, Mingozzi F. Emerging Issues in AAV-Mediated In vivo Gene Therapy. *Mol Ther Methods Clin Dev* 2018; 8:87-104). This approach is exemplified by the development of the engineered AAV-PHP.eB and AAV-PHP.S capsids that transduce the central and peripheral nervous systems (Chan K Y, Jang M J, Yoo B B, Greenbaum A, Ravi N, Wu W L, et al. Engineered AAVs for efficient noninvasive gene delivery to the central and peripheral nervous systems. *Nat Neurosci* 2017; 20:1172-9). These variants can be injected systemically in mice to target the entire brain or peripheral ganglia. However, despite the success of such approaches, AAV vectors in which the primary amino acid sequence of the capsid proteins, VP1, VP2, and/or VP3, has been engineered still suffer from some drawbacks such as the high titers needed for systemic transduction, and questions about their translational potential beyond rodent models.

An aspect of our solution to these problems has been to provide a protein chemistry based method that facilitates the targeted delivery of a viral capsid (as part of a recombinant AAV virion), with its encapsidated cargo, into cells of choice. In this disclosure we provide for the crosslinking of ligands to the AAV capsid through bioorthogonal chemistry to improve tropism and/or to enhance transduction efficiency. In certain embodiments, the ligand of the surface modified viral capsid binds to its cognate receptors on the surface of mammalian cells to mediate gene delivery selectively into cell types which display the appropriate cognate receptor thus enabling targeted viral gene delivery.

In certain of the experiments described below, we generated a non-infective AAV serotype 2 virus through mutation of the heparan sulfate proteoglycan-binding motif in the capsid (Kern A, Schmidt K, Leder C, Müller O J, Wobus C E, Bettinger K, et al. Identification of a Heparin-Binding Motif on Adeno-Associated Virus Type 2 Capsids. *Journal of Virology* 2003; 77:11072-81) (R585/588A, termed AAV2-• HSPG), and then chemically modified surface exposed lysine residues on the assembled • HSPG-AAV2 capsid with a reactive linker comprising a member of a crosslinker reactive pair, e.g., benzylguanine (BG) and cyclooctyne (DBCO). We were then able to crosslink functionalized ligands with a SNAP-tag fusion or azide functionality, to the virus, and restore viral infectivity in a receptor dependent manner.

We initially tested the system using protein ligands such as neurotrophins and cytokines (IL31), since the receptors for these molecules are expressed in subsets of cells in the skin and peripheral nervous system. We then went on to compare protein ligands such as single chain antibodies (scFvs) against the same receptors to understand whether they improve upon ligand targeting. We have also explored other classes of ligand such as the Cholera Toxin B (CTB), and various lectins, with the aim of encoding the same functionality into AAV as that possessed by the ligands—for example, retrograde transport in the case of CTB, or improved binding to cell surface carbohydrates in the case of lectins.

In parallel, we have also assessed other bioorthogonal chemistries in addition to BG-SNAP tag conjugation and the effect of incorporating longer spacers into the linker. We have found that the Strain-promoted Azide-Alkyne Click Chemistry (SPAAC) reaction between dibenzocylooctyne (DBCO) and azido groups surprisingly improves efficiency further. This allows for facile conjugation of AAV to commercially available peptide and protein ligands without the need to generate SNAP fusion proteins.

In summary, our data indicate that our chemical modification approach has a number of advantages over sequence-modified AAV capsids. Unlike sequence modified capsids, for which few human tissue-specific variants have yet been defined, despite intensive research efforts, our approach leverages on the vast number of known human cell receptor-ligand interactions to drive tropism. Unlike sequence modified capsids, for which tissue tropism must be empirically determined, when we ablate the natural cell binding site of the AAV capsid, our approach provides high specificity of cell targeting, driven by the receptor specificity of the attached ligand. And when ligands are attached that increase transduction without ablating or altering the native capsid cellular binding site, greater transduction efficiency is obtained without significantly altering known tropism.

In addition, our approach is compatible with any AAV production platform, with no impact on viral yield. The methods provided herein are also inexpensive to perform, and scalable from small-scale research applications to clinical scale production. Finally, the provided platform for modifying the surfaces of AAV capsids is modular, allowing for essentially any virus/ligand combination, and this should facilitate its translation from rodent models to human patients.

Table 1, below, summarizes some liganded-AAV experiments further described in detail in examples 1-8 below.

homologous base pairs on each side of the mutation. Mutant plasmids were identified by DNA sequencing. The fragment containing the suitable mutation was then subcloned into a plasmid backbone (e.g. pTAV2-0), containing the rest of the protein, and the complete fragment was sequenced to check for additional PCR mutations.

TABLE 1

| Ligand | Class | Receptor | Marker of | AAV type | Chemistry | In vitro | In vivo | Notes |
|---|---|---|---|---|---|---|---|---|
| NGF$^{R121W}$ | Protein | TrkA | Nociceptors | AAV2-HSPG | BG-SNAP | PC12 cells, DRG neurons, organotypic spinal cord | IP, IV, intranerve, subcutaneous | Overlap with TrkA antibody staining in DRG |
| BDNF | Protein | TrkB | Mechano-receptors | AAV2-HSPG | BG-SNAP | DRG neurons | | |
| NT3 | Protein | TrkC | Proprio-ceptors | AAV2-HSPG | BG-SNAP | DRG neurons | | |
| IL31$^{K134A}$ | Protein | IL31RA/OSMR | Keratino-cytes and pruriceptors | AAV2-HSPG | BG-SNAP | Primary keratino-cytes | Subcutaneous | Absence of signal in IL31RA$^{-/-}$ mice |
| Nemoli-zumab | scFv | IL31RA | Keratino-cytes and pruriceptors | AAV2-HSPG | BG-SNAP and DBCO-Azide | Planned | IP, IV, subcutaneous | |
| Cholera Toxin B subunit | Toxin sub-unit | Ganglioside GM1 | Large DRG neurons. Retrograde tracer | AAV2-HSPG | BG-SNAP and DBCO-Azide | DRG neurons | Subcutaneous, intranerve | |
| Wheat Germ Agglutinin | Lectin | N-acetyl glucose-amine | All neurons | AAV2-HSPG, PHP.S | BG-SNAP and DBCO-Azide | PC12 cells, DRG neurons, organotypic spinal cord | IV, intranerve, subcutaneous, Prefrontal cortex | Also boosts PHP.S efficiency in DRG neurons. |
| Isolectin B4 | Lectin | galactose | Vasculature, non-peptidergic nociceptors, microglia | AAV2-HSPG, AAV2, AAV9 | DBCO-Azide | PC12 cells, DRG neurons, organotypic spinal cord | Intranerve, subcutaneous, spinal cord | Also boosts AAV2 and AAV9 efficiency in PC12 cells. |

In subsequent experiments we used other crosslinker-reactive pairs that do not require addition of SNAP tag fusions to functionalize the ligand.

Example 1. Removal of Natural Binding Sites in AAV2

One aim of our early experiments was to engineer the adeno associated virus (AAV) capsid so that the virus will selectively transduce cells of interest. This was achieved by removing natural binding sites for cells in the native AAV capsid protein(s), e.g. by mutation as described herein. The capsid was then chemically functionalized in order to conjugate with a functionalized ligand. Bioorthogonally functionalized ligands were then covalently attached to the virus and tested in vitro on cells and in vivo in mice. Although AAV2, AAV9 and PHP.S have been explored, these examples can be readily applied to other viral capsids as well.

AAV2 binds to heparan sulfate proteoglycans through arginine 585 and 588. These positions were mutated to alanine to create the deletion HSPG having mutations in the CAP gene R585A+R588A.

The plasmid pTAV2-0 contains the entire AAV-2 genome from pAV-2, including both inverted terminal repeats, cloned into the BamHI site of pBluescript II. A sub-plasmid containing a suitable fragment of the AAV-2 was created and used as the template for site-directed mutagenesis reactions. Mutagenesis was performed by using a Stratagene (Amsterdam, The Netherlands) QuikChange site-directed mutagenesis kit according to the manufacturer's protocol. For each mutant, two complementary PCR primers were designed to contain the sequence of the substitution, flanked by 15 to 20

Recombinant AAV2-• HSPG harboring mutations in the CAP gene R585A+R588A (Kern A, Schmidt K, et al. Identification of a Heparin-Binding Motif on Adeno-Associated Virus Type 2 Capsids. Journal of virology 2003; 77:11072-81) and carrying tdTomato under a CAG promoter as a cargo was produced either in HEK293 cells or in SF21 insect cells as described previously (Grieger J C, et al. Production and characterization of adeno-associated viral vectors. Nat Protoc 2006; 1:1412-28; Wu Y, et al. A Recombinant Baculovirus Efficiently Generates Recombinant Adeno-Associated Virus Vectors in Cultured Insect Cells and Larvae. Mol Ther Methods Clin Dev 2018; 10:38-47). Cells were harvested 5 days post infection, lysed with Triton X-100 at 0.5%, nuclease treated, concentrated by tangential flow filtration, and purified using isopycnic ultracentrifugation (Dias Florencio G, et al. Simple downstream process based on detergent treatment improves yield and in vivo transduction efficacy of adeno-associated virus vectors. Mol Ther Methods Clin Dev 2015; 2:15024). Vector genome titration was performed using Q-PCR with primers targeting the promoter region of the viral cargo (Grieger 2006).

Example 2. BG-NHS Functionalization of HSPG for Accepting SNAP Tagged Ligands

Selective attachment of ligands to proteins, e.g., protein labeling, is often accomplished by incorporation of bioorthogonal groups into a protein, followed by chemoselective modifications. This approach is also designated as "tag-and-modify". A variety of bioorthogonal reactions have been developed, which can be classified into: (1) condensation reactions through carbonyls, (2) "click" reactions through azides, (3) inverse electron-demand Diels-Alder cycloadditions (DAINV) and other cycloaddition reactions, (4) transition metal-catalyzed coupling and decaging reactions, and (5) labeling reactions at cysteine residues, as discussed above.

In our first set of experiments, benzylguanine (BG) was attached to exposed lysine by reacting virus with benzylguanine NHS ester (also referred to as SNAP tag substrate, BG-•NHS or BG-GLA-NHS). For this, using a needle, non-aqueous DMSO was added to the vial with the dry SNAP tag ligand BG-NHS to the desired final concentration (e.g. 20 mM) at room temperature. The protein to be amine-functionalized was diluted in solvent (PBS) to the desired final concentration. The two preparations were mixed and incubated at room temperature for 180 minutes, followed by removal of the unreacted components using a centrifugal 100 Kda MWCO filter unit.

BG-GLA-NHS:

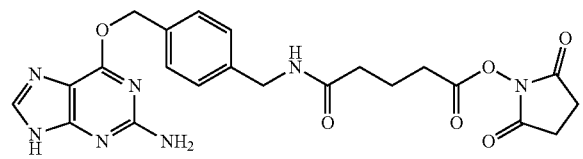 [SMILES: Nc1nc(OCc2ccc(CNC(=O)CCCC(=O)ON3C(=O)CCC3=O)cc2)c2nc[nH]c2n1]

Example 3. Recombinant Ligands with C Terminal SNAP Tags

There are two steps to using this system: cloning and expression of the protein of interest as a SNAP-tag® fusion, and labeling of the fusion with the SNAP-tag substrate of choice. The SNAP-tag is a small protein based on human O6-alkylguanine-DNA-alkyltransferase (hAGT), a DNA repair protein. The SNAP-tag substrate in this case is the guanine leaving group connected to a benzyl linker. In the labeling reaction, the substituted benzyl group of the substrate is covalently attached to the SNAP-tag.

The SNAP-tag protein labeling system enables the specific, covalent attachment of virtually any molecule to a protein of interest (for the present experiments, see Example 4, below).

Figure 1:
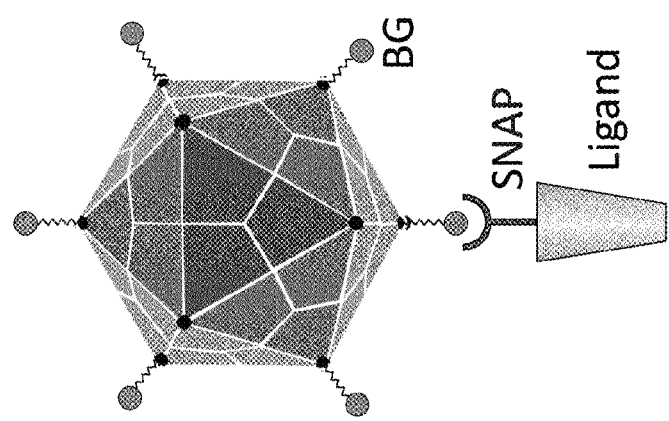
FIG. 1 shows a schematic depiction of surface modification of a viral capsid surface functionalized with BG groups that react with SNAP-tagged fusion ligands to produce a surface modified virus having improved tropism and/or transduction efficiency of genetic cargo.

Recombinant ligands with C terminal SNAP tags were produced in E. coli or in mammalian cells. For the covalent attachments, SNAP-tagged ligands were then attached to the BG-modified virus (see FIG. 1) by adding saturating concentrations of SNAP tagged ligand and incubating at room temperature overnight. Excess non-reacted ligand was removed by passing the reaction through a centrifugal 100 Kda MWCO filter unit.

For the present invention, the experiments were performed in accordance with the instructions of the SNAP-Cell® Starter Kit (NEB) containing a mammalian expression plasmid (pSNAPf) encoding the SNAP-tag® flanked by restriction sites for cloning a gene of interest, with modifications for the present purpose.

Example 4. Targeting and Boosting Transduction—In Vitro and In Vivo Tests of BG-GLA-NHS Modified • HSPG AAV Capsid with Recombinant Ligands with C Terminal SNAP Tags The above capsid surface modification strategy was tested with multiple classes of ligands to determine if the ligand could alter tropism, namely protein ligands, like growth factors, cytokines etc.; toxin subunits, like cholera toxin B subunit; lectins, such as isolectin B4 or wheat germ agglutinin; adhesion factors, like lactadherin; antibodies, such as anti CD-34 (marker of stem cells); and peptides, such as deltorphin opioid receptor ligand.

Figure 2:
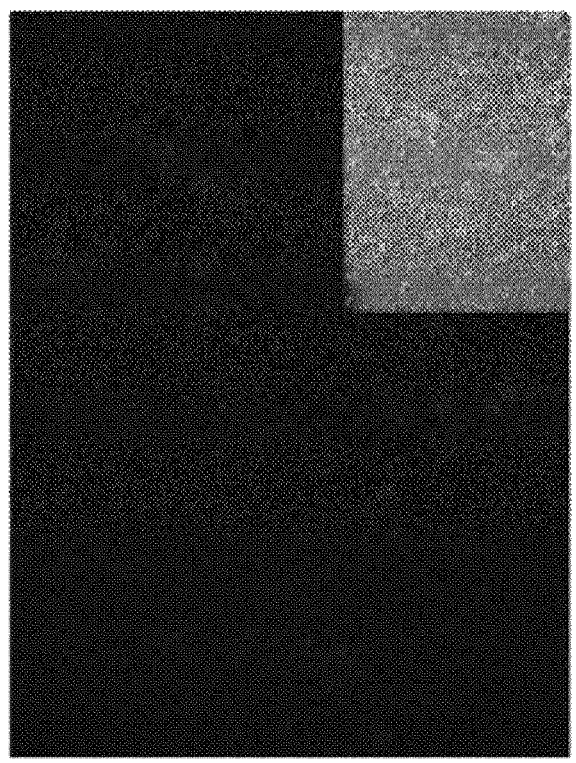
FIG. 2 shows that the • HSPG virus capsid according to the present disclosure has no residual infective activity (dark picture); the construct with the heparin binding site removed was tested on sensory neurons in a fluorescent reporter mouse model. The inset shows the phase contrast microscopic image of the cells.
Figure 3:
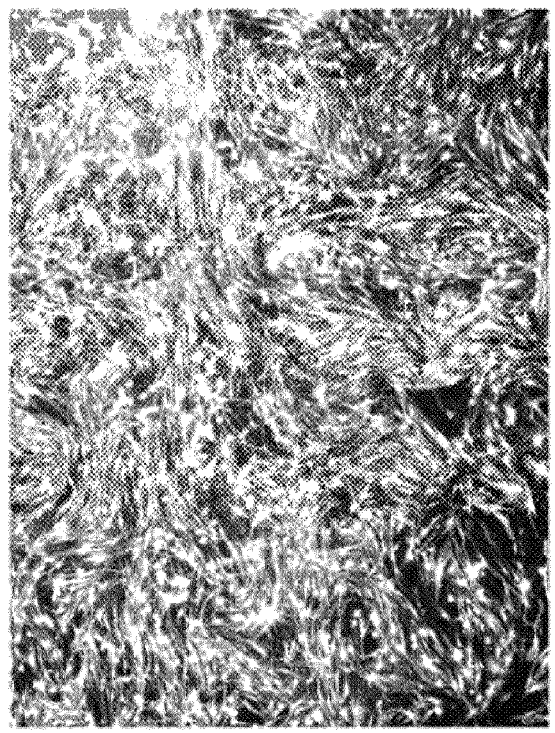
FIG. 3 shows that capsid surface modified with a wheat germ agglutinin (WGA) fusion ligand fully reverted the viral transduction efficiency to 100% (fluorescent cells) when tested on sensory neurons in a fluorescent reporter mouse model analogous to that used for FIG. 2.

Example 4a. • HSPG Capsid not Infective, Surface Modified Viral Capsid Reverts Transduction Efficiency It was shown first that the HSPG virus particle according to the invention had no residual infective activity as tested on sensory neurons in a fluorescent reporter mouse model (FIG. 2). The wheat germ agglutinin (WGA, lectin; i.e, WGA-SNAP) fusion (viral capsid surface modified with WGA via the BG/SNAP linker chemistry) improved viral transduction efficiency to 100% or better when tested on sensory neurons in the same fluorescent reporter mouse model (FIG. 3).

Then, several ligands were tested, the neurotrophic factors NGF, NT3 and BDNF (protein ligands) delivered virus to different specific neuronal populations, that is, they conferred different tropism, depending on the factor used in the capsid construct tested in a fluorescent reporter mouse model (FIGS. 4a-4c). Cholera Toxin B subunit (toxin) specifically directed virus retrogradely to neuronal cell bodies (i.e. cell compartment/part specific) (FIG. 5). In similar tests, lactadherin (adhesion factor) specifically directed virus to macrophages and neurons exposing phosphatidylserine, and deltorphin (peptide) specifically directed virus to neurons expressing the Mu and Delta opioid receptors.

In the experiments shown in FIGS. 6a-6b, the capsid surface modified with the NGF ligand IV was injected into the trigeminal ganglia, then sensory neuron tissue was taken and analyzed three weeks later. The sectioned tissue was stained with an antibody against TrkA (the receptor for NGF), and a very good overlap was found. The TrkA antibody stain is not perfect, so an 80% overlap is extremely relevant.

In the experiments shown in FIG. 7, the sections from FIGS. 6a-6c were stained with antibodies against NF200 and IB4, which label other neurons (mechanoreceptors and non-peptidergic nociceptors, respectively). Again, these markers are not perfect but it can be seen that the green and blue cells are different from the red infected cells.

As a negative control, virally introducing the IL31 ligand into an IL31 receptor knockout mouse does not lead to an infection.

In summary, all ligand-labeled viruses successfully and specifically transduced only those cells expressing the respective receptor, both when applied in vitro to cultured cells, and when injected in vivo in mice, i.e. can be injected systemically or locally and selectively target different populations of cells.

Example 4b. Targeting TrkA+ Nociceptors

In this example, TrkA+ nociceptors in the peripheral nervous system were targeted with a capsid surface modified contruct. NGF$^{R121W}$ ligand, which binds to but doesn't activate TrkA, was crosslinked to HSPG-AAV2 (the capsid prepared as described above) with a tdTomato cargo. The construct was injected into mice subcutaneously, intra-nerve, retro-orbital and intraperitoneal. After three weeks, fluorescence was detected and quantified by using a TrkA antibody.

It was found that for the retro-orbital application 80% of TrkA+ cells were infected by NGF-AAV. 83% of NGF-AAV infected cells were TrkA+. It was also found that the different routes of administration did not differ significantly in their highly effective outcomes.

Example 4c. Targeting IL31RA+ Itch Receptors

In this example, IL31RA was targeted with an AAV that has been surface modified to comprise an IL31$^{K134A}$ targeting ligand that binds to, but doesn't activate, IL31RA. The IL31RA was crosslinked to • HSPG-AAV2 (capsid as described above) with a tdTomato cargo. The construct was injected into wildtype and IL3 1RA knockout mice. After three weeks, fluorescence from the reporter gene was detected and overlap quantified by using a keratin 14 antibody. It was found that targeted cells were basically completely positive for K14. Important in IL31RA knockout mice, no tomato expression was detected.

Example 4d. Targeting with Isolectin B4

In this example, Isolectin B4 (1B4) was conjugated to • HSPG-AAV2 as described above with a tdTomato cargo. 1B4 can be used as a marker for vasculature, non-peptidergic nociceptors, and/or microglia. The construct was injected subcutaneously, intra-nerval, or intraspinally. After three weeks, fluorescence was detected. It was found that targeted cells were basically completely positive, irrespective of the route of administration.

Example 4e. Targeting with Wheat Germ Agglutinin

In this example, wheat germ agglutinin (WGA) was conjugated to HSPG-AAV2 as described above with a tdTomato cargo. WGA binds to N-acetylglucosamine on the cell membrane of most neurons and is used as a (transsynaptic) tracer. The construct was injected in mice i.v. in P1 neonates, or intracortical in adult mice. After three weeks, fluorescence from the reporter gene was detected.

It was found that gene delivery is more efficient with liganded viruses (see FIGS. 8a-8b). Cultured DRG neurons were infected with AAV9 variant PHP.S (1E+9 vector genome (VG), and it was found that the above WGA modified construct resulted in a strong increase of delivery (see FIG. 8b).

Example 5. Targeting with Neurotrophin Ligands

We selected neurotrophin ligands NGF, BDNF, and NT3 to conjugate to AAV2-• HSPG because their receptors mark functionally distinct populations of peripheral sensory neuron. We also generated mutant NGF$^{R121W}$ that binds to, but doesn't signal through, TrkA. Thus NGF$^{R121W}$ was chosen to assess ligand-targeting of AAV.

As a conjugation strategy, we first attempted to encode a CLIP-tag at the N-terminus of the AAV2 VP2 protein in order to attach SNAP-tagged ligands via bifunctional linkers. This approach was not successful because the AAV viral capsids were not able to support incorporation of the CLIP-tag, and instead were produced with only VP1 and VP3 proteins in their capsid. We further explored the insertion of smaller tags such as the Spytag for eventual conjugation to ligand-Spycatcher fusions. Insertion of the Spytag at position 588 in the viral capsid led to viral particles containing the Spytag, however yield was reduced by more than 10-fold. These experiments illustrate the difficulties associated with genetically engineering the AAV capsid for attachment of targeting ligands.

To solve this problem, we reasoned that because the AAV capsid has a large number of exposed lysine residues on its surface (more than 1000), it should be amenable to modification via amine-reactive chemical groups, such as N-hydroxysuccinimide (NHS) esters. Thus, in theory, we would be able to decorate the AAV capsid with SNAP-tag reactive benzylguanine (BG) groups via a labelling reaction with an NHS-BG probe. We therefore set up reactions with a range of molar ratios of BG-GLA-NHS to AAV2-• HSPG and applied the purified product to isolated Dorsal Root Ganglion (DRG) neurons. From this experiment we determined that NGF$^{R121W}$ modified AAV2-• HSPG did indeed transduce a population of DRG neurons at an optimal molar ratio of BG-GLA-NHS to AAV2-• HSPG of 3E+9 VG of virus to 1.73 nmol linker, while AAV2-• HSPG alone was ineffective (FIGS. 9a-9l). We have since optimized the reaction (see methods below) and found that once the optimal ratio for each AAV preparation has been determined empirically, the modification works with a broad range of reactive linkers, e.g., those with NHS ester derivatives, virus concentrations and purities, and classes of ligand.

Methods

Recombinant AAV2-• HSPG was prepared in accordance with the procedure described in Example 1.

Example 5a. Targeting with NGF$^{R121W}$-SNAP:: AAV2-• HSPG

NGF$^{R121W}$-SNAP was produced in mammalian cells as described previously (Nocchi L, et al. Nerve growth factor-mediated photoablation of nociceptors reduces pain behavior in mice. *Pain* 2019). To conjugate to AAV, purified AAV2-• HSPG was reacted with BG-GLA-NHS (NEB) or BG-PEG13-NHS (custom synthesis) at an apparent VG to NHS linker molar ratio of 3E+9 VG of virus to 1.73 nmol linker, in PBS pH7.2 for 3 hours at room temperature. The reaction was purified using a 100 KDa MWCO centrifugal filter, and further incubated with 5 µM NGF$^{R121W}$-SNAP overnight at room temperature. Excess unreacted NGF$^{R121W}$-SNAP was removed by passing through a 100 Kda MWCO centrifugal unit twice, and the crosslinked product was resuspended in PBS.

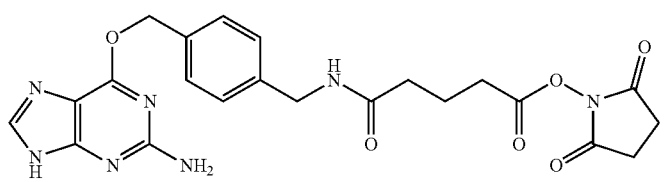

BG-GLA-NHS

-continued

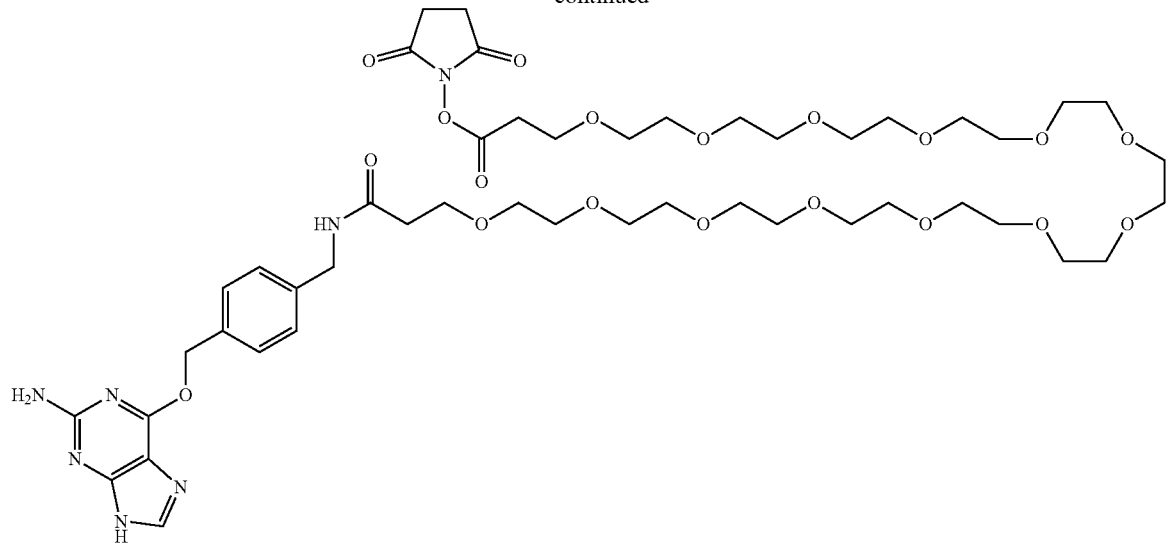

Formula Weight: 1040, 12(4)
Formula: $C_{47}H_{73}N_7O_{19}$

BG-PEG13-NHS

In Vivo Injections and Tissue Processing

For in vivo injection experiments, mice were anesthetized with 2-2.5% Isoflurane, and then injected via subcutaneous, intranerve, intraperitoneal or retro-orbital (IV) routes. For subcutaneous injection, 3E+10 VG of NGF$^{R121W}$-SNAP::•AAV2-• HSPG in 10 ul was injected into the plantar surface of the paw. For intranerve injection, 3E+9 VG NGF$^{R121W}$-SNAP::• HSPG-AAV2 in 2 ul was injected into the sciatic nerve. For intraperitoneal injection and retro-orbital injections, 8E+10 VG or 3E+10 VG of NGF$^{R121W}$-SNAP::•HSPG-AAV2 were injected. 3 weeks later, dorsal root ganglia and trigeminal ganglia were harvested, fixed in 4% paraformaldehyde, cleared in ScaleS and prepared as wholemount samples. In some experiments, DRG were also sectioned at 10 μm, incubated with blocking solution containing 5% serum and 0.3% Triton-X in PBS for 30• min, and subsequently with anti-TrkA antibody (R&D systems, 1:200) in blocking solution overnight at 4•° C. Secondary antibodies were added in blocking solution for 1-2•h and the slides were mounted with prolong gold. Images were taken with a Leica SP5 confocal microscope and analyzed in ImageJ.

Results

To test viral transduction in vitro, 1E+9 VG in 100 ul of PBS was applied to dorsal root ganglion neurons in a 96 well plate. Fluorescence was monitored daily and was usually evident after 24 hours, peaking 4 days later. As shown in FIGS. 10a-10c, NGF$^{R121W}$, BDNF and NT3 coupled AAV2-• HSPG targets morphologically distinct subtypes of cell.

To test viral transduction in vivo, NGF$^{R121W}$::AAV2-• HSPG in 10 ul of PBS was injected either intra-orbital, intra-peritoneal, intranerve or subcutaneous into mice. 3 weeks later mice were sacrificed and tissue was harvested to monitor fluorescence of the reporter gene across different organs.

Example 5b. Influence on Linker Length on Transduction NGF$^{R121W}$::AAV2-• HSPG in DRG In initial experiments we tested two different reactive linkers, a short one termed BG-GLA-NHS, commercially available from NEB, and a "long one" termed BG-PEG13-NHS which we synthesized in house. Equivalent amounts (3E+10 VG) of NGF$^{R121W}$::AAV2-• HSPG modified with either BG-GLA-NHS or BG-PEG13-NHS were injected intra-orbitally into mice and DRG harvested to assess transduction efficiency. See FIGS. 11a-11f. From these experiments it was clear that the longer linker performed far better than the shorter one, without being bound by theory, one possibly could be because of greater stability and/or potentially immune evasion in vivo.

We further compared injection routes for NGF$^{R121W}$::AAV2-• HSPG and found that systemic injection produced higher levels of viral transduction in the DRG compared to local subcutaneous or intra nerve injections. See FIGS. 12a-12d. This was unexpected because when we have injected other non-modified AAV serotypes systemically, we have observed very little transduction, even for PHP.S which is reported to function upon intra-orbital injection (Chan K Y, et al. Engineered AAVs for efficient noninvasive gene delivery to the central and peripheral nervous systems. Nat Neurosci 2017; 20:1172-9). This data illustrates the efficiency of our approach.

Finally, we assessed the specificity of NGF$^{R121W}$::AAV2-• HSPG mediated gene delivery by harvesting DRG from infected animals, sectioning and staining with antibodies against the NGF receptor TrkA. We observed a strong correlation between virally infected cells and the presence of the TrkA receptors: 80% of TrkA positive cells were infected by NGF$^{R121W}$::AAV2-• HSPG, and 83% of NGF$^{R121W}$::AAV2-• HSPG infected cells were TrkA positive. See FIGS. 13a-13d.

Example 5c. Targeting with IL31$^{K134A}$::AAV2-• HSPG

Interleukin 31 (Il31) was selected as a targeting ligand because its receptors IL31RA and OSMR are highly expressed on keratinocytes and they play a key role in inflammatory itch (Fume M, et al. Emerging role of interleukin-31 and interleukin-31 receptor in pruritus in atopic dermatitis. *Allergy* 2018; 73:29-36). We generated a mutant IL31$^{K134A}$ that binds to, but doesn't signal through, IL31RA (Nocchi L. et al. Interleukin-31-mediated photoablation of pruritogenic epidermal neurons reduces itch-associated behaviours in mice. *Nat Biomed Eng* 2019; 3:114-25) and conjugated this to AAV2-• HSPG as described above. IL31$^{K134A}$::AAV2-• HSPG was injected subcutaneously at 3E+10 VG in mice and three weeks later, skin harvested, sectioned and stained with anti-K14 antibody, a marker of keratinocytes. As shown in FIGS. 14a-14c, we observed an almost 100 percent overlap between virally infected cells and K14 positive keratinocytes. Importantly, because fluorescence persisted for longer than the 8-10 day epidermal turnover in mice (Potten C S, Saffhill R, Maibach H I. Measurement of the transit time for cells through the epidermis and stratum corneum of the mouse and guinea-pig. Cell Tissue Kinet 1987; 20:461-72), our data indicate that epidermal stem cells are also being targeted in this experiment. Indeed, transcriptomics studies indicate that IL31RA is expressed in basal keratinocytes in the interfollicular and follicular epidermis, many of which are epidermal stem cells (Joost S, Zeisel A, Jacob T, Sun X, La Manno G, Lonnerberg P, et al. Single-Cell Transcriptomics Reveals that Differentiation and Spatial Signatures Shape Epidermal and Hair Follicle Heterogeneity. Cell Syst 2016; 3:221-37 e9).

To investigate the selectivity of IL31$^{K134A}$::AAV2-• HSPG gene delivery further we utilized an IL31RA knockout mouse line (IL31RA$^{-/-}$) (Nocchi 2018). We were unable to detect any signal of the reporter tdtomato in IL31RA$^{-/-}$ mice injected subcutaneously with IL31$^{K134A}$::AAV2-• HSPG, indicating that transduction is indeed receptor specific, See FIGS. 15a-15c.

Materials and Methods
AAV Vector Production

Recombinant AAV2-• HSPG was prepared in accordance with the procedure described in Example 1.
Chemical Modification and Coupling of IL31$^{K134A}$-SNAP to AAV2-• HSPG IL31$^{K134A}$-SNAP was produced as described previously (Nocchi 2019). To surface modify the AAV, purified AAV2-• HSPG was reacted with BG-PEG13-NHS (custom synthesis) at an apparent VG to NHS linker molar ratio of 3E+9 VG of virus to 1.73 nmol linker, in PBS pH7.2 for 3 hours at room temperature. The reaction was purified using a 100 KDa MWCO centrifugal filter, and further incubated with 504 IL31$^{K134A\text{-}SNAP}$ overnight at room temperature. Excess unreacted functionalized ligand was removed by passing through a 100 KDa MWCO centrifugal unit twice, and the conjugated product was resuspended in PBS.

In Vivo Injections and Tissue Processing

For in vivo injection experiments, wildtype or IL31RA$^{-/-}$ mice were anesthetized with 2-2.5% Isoflurane, and then 3E+10 VG of IL31$^{K134A}$-SNAP::AAV2-• HSPG in 10 ul of PBS was injected subcutaneously into the ear. 3 weeks later, skin was harvested, fixed in 4% paraformaldehyde overnight and sectioned at 40 m. Sections were stained overnight at 4° C. with rabbit anti-K14 antibody (Covance 1:200 dilution) in PBS containing 5% goat serum+0.3% Triton-X. Secondary anti-rabbit Alexa488 antibody was diluted 1:1000 and incubated for 2 h at room temperature in the dark. Slides were mounted with prolong gold and Images were taken with a Leica SP5 confocal microscope and analyzed in ImageJ.

Results

Il31 was selected as a targeting ligand because its receptors IL31RA and OSMR are highly expressed on keratinocytes and they play a key role in inflammatory itch (Fume 2018). Moreover, we previously generated a mutant IL31$^{K134A}$ that binds to but doesn't signal through IL31RA (Nocchi 2019), and demonstrated that this can be used to target the itch pathway.

IL31$^{K134A}$::AAV2-• HSPG was injected subcutaneously in mice and skin sections examined for overlap with K14, a marker of keratinocytes. As shown in FIGS. 14a-14c, we observed an almost 100 percent overlap between virally infected cells and K14 positive keratinocytes. Importantly, because fluorescence persisted for longer than the 8-10 day epidermal turnover in mice (Potten 1987), our data indicate that epidermal stem cells are also being targeted in this experiment. Indeed, transcriptomics studies indicate that IL31RA is expressed in basal keratinocytes in the interfollicular and follicular epidermis, many of which are epidermal stem cells (Joost 2016).

To investigate the selectivity of IL31$^{K134A}$::AAV2-• HSPG gene delivery further we took advantage of an IL31RA knockout mouse line (IL31RA$^{-/-}$) we had generated previously (Nocchi 2019). We were unable to detect any signal from the tdtomato reporter gene in IL31RA$^{-/-}$ mice injected subcutaneously with IL31$^{K134A}$::AAV2-• HSPG (FIGS. 15a-15c), indicating that transduction is indeed receptor specific.

Example 6. Targeting with Cholera Toxin B Toxin Subunit

Background

Cholera Toxin B subunit (CTB) was selected because it is a classical retrograde tracer and we reasoned that by coupling it to AAV we may be able to achieve transport of AAV from neuronal terminals back to cell bodies. The natural propensity of wildtype AAV serotypes for retrograde transport is low, and thus there is an unmet need for both gene therapy and basic science, to produce a platform that enables trafficking of AAV along projection neurons. Previous attempts to address this problem have used directed evolution to engineer retrograde functionality into the capsid of AAV2 (rAAV2-retro) (Tervo D G, et al. A Designer AAV Variant Permits Efficient Retrograde Access to Projection Neurons. *Neuron* 2016; 92:372-82). We reasoned however, that if CTB (and potentially any other retrograde tracer) promotes retrograde transport of AAV, then it would allow for simple, post-hoc conversion of any AAV into a retrograde-AAV.

Methods

We initially produced a CTB-SNAP fusion protein in *E. coli* but found that the presence of the SNAP-tag reduced its retrograde transport. We thus purchased unmodified CTB and labelled it with Azido-PEG4-NHS ester. Briefly, CTB was reacted with 10-fold molar equivalent of Azido-PEG4-NHS ester in PBS at pH7.2 for 3 hours at room temperature. Unreacted Azido groups were removed via dialysis with a 2 kDa MWCO membrane. To conjugate to AAV, Purified AAV2-• HSPG, as prepared above, was reacted with DBCO-PEG4-NHS at a VG to molar ratio of 3E+9 VG of virus to 1.73 nmol linker, in PBS pH7.2 for 3 hours at room temperature. The reaction was purified using a 100 KDa MWCO centrifugal filter, and further incubated with 5 μM CTB-PEG4-Azide overnight at room temperature. Excess unreacted ligand was removed by passing through a 100 KDa MWCO centrifugal unit twice, and CTB-• HSPG-AAV was resuspended in PBS.

Results

To test viral transduction in vitro, 1E+9 VG of CTB-• HSPG-AAV in 100 ul of PBS was applied to dorsal root ganglion neurons in a 96 well plate. Fluorescence was monitored daily and was usually evident after 24 hours, peaking 4 days later. CTB is known to label large DRG neurons (presumed mechanoreceptors), and indeed CTB-• HSPG-AAV transduces large neurons as shown in FIG. 16a.

To test viral transduction in vivo, 3E+9 VG of CTB-• HSPG-AAV was injected subcutaneously in mice. 3 weeks later mice were sacrificed and tissue was harvested to monitor cellular fluorescence. We observed fluorescent signal in fibers of the sciatic nerve, and in large neurons in the DRG, see FIGS. 16b and 16c, respectively.

In ongoing experiments, we have also conjugated CTB to wildtype AAV2 and injected it into the brain of mice. Our aim here is to directly compare retrograde transport of CTB-AAV2 with wildtype AAV2.

Example 7. Targeting with Lectins

Lectins were selected because they bind specifically to the same cell surface carbohydrates utilized by AAV for cell attachment. We thus reasoned that by conjugating lectins to AAV2-• HSPG we may be able to mimic and improve natural AAV serotypes. In initial experiments we screened several lectin-AAV2-• HSPG conjugates for transduction capability in organotypic spinal cord cultures. We then selected Wheat Germ Agglutinin (WGA) and Isolectin B4 (IB4) for further characterization, with an aim to also examine Lens culinaris lectin (Lens) and Wisteria floribunda lectin (WFL) in the future.

General Methods

Lectins were reacted with 20-fold molar equivalent of Azido-PEG4-NHS ester in PBS at pH7.2 for 3 hours at room temperature. Unreacted Azido groups were removed using a 10 KDa molecular MWCO centrifugal filter. To surface functionalize AAV, purified AAV2-• HSPG as prepared above, was reacted with DBCO-PEG4-NHS at a VG to linker molar ratio of 3E+9 VG of virus to 1.73 nmol linker, in PBS pH7.2 for 3 hours at room temperature. The reaction was purified using a 100 KDa MWCO centrifugal filter, and further incubated with 5 µM Lectin-PEG4-Azide overnight at room temperature. Excess unreacted ligand was removed by passing through a 100 KDa MWCO centrifugal unit twice, and the produced lectin-• HSPG-AAV construct was resuspended in PBS.

Example 7a. Targeting with WGA::AAV2-• HSPG

Chemical Modification and Coupling of WGA to AAV2-• HSPG

WGA was functionalized with 20-fold molar equivalent of Azido-PEG4-NHS ester in PBS at pH7.2 for 3 hours at room temperature. Unreacted reactive linker was removed using a 10 KDa molecular MWCO centrifugal filter. To surface functionalize to AAV, purified AAV2-• HSPG as prepared above, was reacted with DBCO-PEG4-NHS at an apparent VG to DBCO-PEG4-NHS molar ratio of 3E+9 VG of virus to 1.73 nmol linker, in PBS pH7.2 for 3 hours at room temperature. The reaction was purified using a 100 KDa MWCO centrifugal filter, and further incubated with 5 µM WGA-PEG4-Azide overnight at room temperature. Excess unreacted functionalized ligand was removed by passing through a 100 KDa MWCO centrifugal unit twice, and the produced WGA HSPG-AAV construct was resuspended in PBS.

To test viral transduction in vitro, 1E+9 VG WGA::AAV2-• HSPG_in 100 ul of PBS was applied to dorsal root ganglion neurons in a 96 well plate. Fluorescence was monitored daily and was evident after 24 hours, peaking 4 days later, see FIG. 17a. WGA::AAV2-• HSPG transduced essentially all cells in the dish. Given this apparent high efficiency, we also tried WGA::AAV2-• HSPG in other difficult to transduce cell types such as mouse early embryos. Blastocysts were dissected from mice, and grown in vitro in 100 ul of KSOM media containing 1.6E+9 VG of WGA::AAV2-• HSPG. Fluorescence was monitored daily and was evident after 24 hours, peaking after 4 days by which point 100% of cells were fluorescent, see FIG. 17b.

All images were taken with a Leica SP5 confocal microscope and analyzed in ImageJ.

To determine whether WGA::AAV2-• HSPG targets peripheral neurons in vivo in mice, we performed systemic injections in neonatal mice. For experiments in neonatal mice, P1 pups were injected with 1E+9 VG of WGA::AAV2-• HSPG in 1 ul PBS into the superficial temporal vein as described previously (Stoica L, Ahmed S S, Gao G, Sena-Esteves M. Gene transfer to the CNS using recombinant adeno-associated virus. Curr Protoc Microbiol 2013; Chapter 14:Unit 14D 5). 5 weeks later mice were sacrificed, and skin, Dorsal Root Ganglia (DRG) and spinal cord were harvested and fixed in 4% paraformaldehyde. Skin was cleared with ScaleS and prepared as a wholemount sample, DRG and spinal cord were sectioned at 10 m and mounted onto glass slides.

In neonatal mice injected IV with 1E+9 VG of WGA::AAV2-• HSPG we detected robust transduction throughout the peripheral nervous system in the skin, DRG and spinal cord but not in the central nervous system. See FIGS. 18a-18c. We detected robust tdTomato fluorescence throughout the peripheral nervous system that was evident as nerve fibers in the skin (FIG. 18a), cell bodies in the DRG (FIG. 18b) and central terminations in the spinal cord (FIG. 18c). We did not observe fluorescence in the central nervous system, indicating that WGA::AAV2-• HSPG does not cross the blood brain barrier.

We also investigated whether WGA::AAV2-• HSPG undergoes retrograde transport in the brain by injecting modified virus into the prefrontal cortex and examining the cell bodies of projection neurons in the thalamus for fluorescence.

For injection in adult mouse brain, mice were anesthetized with 2-2.5% Isoflurane. A craniotomy was performed and 6E+8 VG of WGA::AAV2-• HSPG in 500 nl PBS was injected into the prefrontal cortex using standard stereotaxic techniques at the following coordinates: M/L=0.500, A/P=−1.700, D/V=−1.8 (Stoica 2013). 5 weeks later, mice were perfused with 4% paraformaldehyde, brains harvested and coronal sections made at 100 m. Sections were stained with DAPI before imaging.

As can be seen in FIGS. 19a-19c, we detected robust signal in brain slices at the injection site (FIG. 19a) and in the cell bodies of projection neurons in the thalamus (FIGS. 19b and 19c).

Example 7b. Boosting with WGA::PHP.S

To explore whether surface functionalization with the WGA ligand could also be used to increase transduction efficiency of a synthetic AAV vector, we surface functionalized PHP.S, which has previously been demonstrated to transduce DRG neurons effectively. Purified PHP.S was prepared as above, and reacted with DBCO-PEG4-NHS at VG:linker molar ratios of 1E+9 VG to 0.43 nmol, 0.87 nmol, 1.73 nmol, 2.6 nmol, or 3.47 nmol DBCO-PEG4-NHS in PBS pH7.2 for 3 hours at room temperature. The reaction was purified using a 100 KDa MWCO centrifugal filter, and further incubated with 0.1 nmol WGA-PEG4-Azide overnight at room temperature. Excess unreacted functionalized WGA was removed by passing through a 100 KDa MWCO centrifugal unit twice, and the produced WGA-PHP.S construct was resuspended in PBS. Unmodified and modified PHP.S was then applied to DRG neurons at 1E+9 VG in 100 ul PBS. As can be seen in FIGS. 20a-20l, WGA-PHP.S increased transduction efficiencies substantially when applied to DRG neurons at equivalent titers to unmodified PHP.S (1E+9 VG). This was evident at a range of DBCO-PEG4-NHS molar quantities from 0.43 nmol to 3.47 nmol.

Example 7c. Targeting with IB4::AAV2-• HSPG

IB4 is used as a marker of the vasculature in the periphery of non-peptidergic sensory neurons in the DRG and of microglia in the central nervous system. We thus tested subcutaneous, intranerve and intraspinal injection of IB4::AAV2-• HSPG in mice.

Chemical Modification and Coupling of IB4 to AAV2-• HSPG

IB4 was reacted with 20-fold molar equivalent of Azido-PEG4-NHS ester in PBS at pH7.2 for 3 hours at room temperature. Unreacted Azido linker were removed using a 10 KDa molecular MWCO centrifugal filter. To conjugate to AAV, Purified AAV2-• HSPG was reacted with DBCO-PEG4-NHS at an apparent VG to DBCO-PEG4-NHS molar ratio of 3E+9 VG of virus to 1.73 nmol linker, in PBS pH7.2 for 3 hours at room temperature. The reaction was purified using a 100 KDa MWCO centrifugal filter, and further incubated with 5 µM IB4-PEG4-Azide overnight at room temperature. Excess unreacted IB4 was removed by passing through a 100 KDa MWCO centrifugal unit twice, and IB4-• HSPG-AAV was resuspended in PBS.

In Vitro Application, In Vivo Injections and Tissue Processing

For experiments in cultured sensory neurons, DRG were harvested from mice and incubated in 1•mg/ml collagenase IV and 0.05% Trypsin for 25•min each at 37•° C. Cells were filtered and suspended in medium containing DMEM, 10% heat inactivated fetal bovine serum, 0.8% glucose, and 100•U) of penicillin/streptomycin, and plated on glass coverslips treated with poly-L-lysine. The following day, medium was removed and 1E+9 VG of 1B4::AAV2-• HSPG in 100 ul of PBS was added to the cells. After 2 hours PBS was replaced with media and cells were maintained at 37° C. for 5 days before imaging with an Zeiss AxioObserver A1 microscope.

For in vivo injection experiments, mice were anesthetized with 2-2.5% Isoflurane, and then injected via subcutaneous, intranerve or intraspinal routes. For subcutaneous injection, 3E+10 VG of IB4::AAV2-• HSPG in 10 ul was injected into the plantar surface of the paw. For intranerve injection, 3E+9 VG IB4::• HSPG-AAV2 in 2 ul was injected into the sciatic nerve. For intraspinal injection 6E+8 VG of IB4::• HSPG-AAV2 in 1 ul was injected into the lumbar spinal cord. 3 weeks later, tissue was harvested, fixed in 4% paraformaldehyde, cleared in ScaleS and prepared as wholemount samples. For intranerve injections, spinal cord was also sectioned at 10 µm and stained with IB4-488 as described previously (Dhandapani R, Arokiaraj C M, Taberner F J, Pacifico P, Raja S, Nocchi L, et al. Control of mechanical pain hypersensitivity in mice through ligand-targeted photoablation of TrkB-positive sensory neurons. *Nature communications* 2018; 9:1640). Images were taken with a Leica SP5 confocal microscope and analyzed in ImageJ.

Results

Figure 22D:
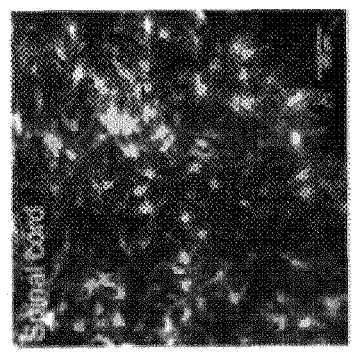
Figure 22C:
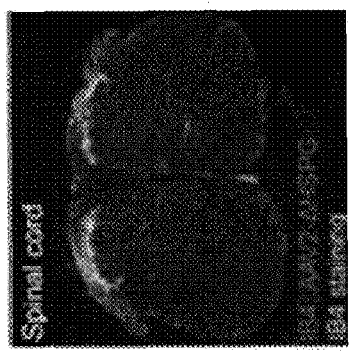
Figure 22B:
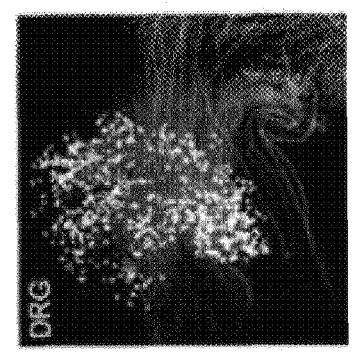
Figure 22A:

In the peripheral nervous system, IB4 is used as a marker of non-peptidergic sensory neurons. We thus first tested whether IB4::AAV2-• HSPG would transduce this population of neurons in vitro. As shown in FIG. 21 we observed robust tdTomato fluorescence in cultured DRG neurons that was confined to mainly small diameter cells, indicative of non-peptidergic sensory neurons. IB4 is also used as a marker of the vasculature in the periphery, and of microglia in the central nervous system. We therefore tested different injection routes in mice to determine whether IB4::AAV2-• HSPG would target these structures in vivo. Following subcutaneous injection of IB4::AAV2-• HSPG we detected tdTomato expression in endothelial and smooth muscle cells surrounding blood vessels (FIG. 22a). Upon injection of 3E+9 VG IB4::• HSPG-AAV2 into the left sciatic nerve we observed fluorescence in non-peptidergic neurons in the DRG (FIG. 22b) and their terminations in the spinal cord (FIG. 22c). To ascertain whether this expression coincided with IB4 positive neurons we stained spinal cord sections with fluorescently labelled IB4-488. As shown in FIG. 22c, we observed clear overlap in the ipsilateral spinal cord between 1B4::• HSPG-AAV2 transduced neurons and 1B4-488 staining that was absent in the contralateral cord. Finally, following injection of IB4::• HSPG-AAV2 into the spinal cord we detected robust expression of tdTomato in microglia (FIG. 22d).

Example 7d. Substantial Boosting with IB4::AAV2-HSPG and IB4::AAV9-HSPG

Methods
AAV Production

Recombinant AAV2 and AAV9 with a GFP cargo were produced either in SF21 or HEK293 respectively as described previously (Grieger 2006 and Wu 2018). Cells were harvested 5 days post infection, lysed with Triton X-100 at 0.5%, nuclease treated, concentrated by tangential flow filtration, and purified using isopycnic ultracentrifugation (Dias Florencio G, Precigout G, Beley C, Buclez P O, Garcia L, Benchaouir R. Simple downstream process based on detergent treatment improves yield and in vivo transduction efficacy of adeno-associated virus vectors. *Mol Ther Methods Clin Dev* 2015; 2:15024). Vector genome titration was performed using Q-PCR with primers targeting the promoter region of the viral cargo (Grieger 2006).

Chemical Modification and Coupling of IB4 to AAV2 or AAV9

IB4 was reacted with 20-fold molar equivalent of Azido-PEG4-NHS ester in PBS at pH7.2 for 3 hours at room temperature. Unreacted azido linker was removed using a 10 KDa molecular MWCO centrifugal filter. To conjugate to AAV, purified AAV2 or AAV9 was reacted with DBCO-PEG4-NHS at an apparent VG to DBCO-PEG4-NHS molar ratio of 3E+9 VG of virus to 1.73 nmol linker in PBS pH7.2 for 3 hours at room temperature. The reaction was purified using a 100 KDa MWCO centrifugal filter, and further incubated with 5 µM IB4-PEG4-Azide overnight at room temperature. Excess unreacted IB4 was removed by passing through a 100 KDa MWCO centrifugal unit twice, and 1B4-AAV2 or IB4-AAV9 were resuspended in PBS.

In Vitro Application to PC12 Cells

PC12 cells were maintained at 37° C. in DMEM/F12 medium containing 5% horse serum 5% fetal bovine serum, and 100•U of penicillin/streptomycin. Varying concentrations of wildtype AAV2, wildtype AAV9, IB4-AAV2 or IB4-AAV9 were incubated with PC12 cells in PBS for 2 hours. Media was then replaced and cells were maintained at 37° C. for 5 days before fixation in 4% PFA, labelling with DAPI and imaging with a Zeiss AxioObserver A1 microscope. Images were analyzed by measuring the GFP fluorescence in each DAPI positive cells and plotting as the mean+/−SEM for each titer.

Results

PC12 cells are difficult to transduce using wildtype AAV serotypes such as AAV2 or AAV9. We therefore asked whether conjugation of AAV2 or AAV9 to IB4 would increase AAV transduction efficiency in this cell type. As shown in the plot of FIG. 23 and the images of FIGS. 24a-f24f, we were unable to detect GFP fluorescence in cells treated with AAV2 at any concentration from 2E+7 to 5E+9 VG. However, conjugation of IB4 to AAV increased transduction efficiency substantially (FIGS. 24g-24l) such that scattered GFP positive cells were evident at 5E+8VG and this increased to more than 80% efficiency at 5E+9VG. Quantification of these values (measured as GFP fluorescence intensity across all cells) revealed that at 5E+8 VG, conjugation of IB4 to AAV2 increased efficiency by 15 fold, while at 1E+9 VG the increase was 38 fold, while at 5E+9 VG the increase in efficiency was 104 fold.

Similarly, GFP fluorescence in treated PC12 cells was not detected at any concentration with wildtype AAV9, see the plot FIG. 25 and FIGS. 26a-26f. In contrast, IB4-AAV9 treated cells exhibited increasing numbers of GFP positive cells from concentrations of 5E+8 VG with high efficiency at 5E+9VG, see the plot FIG. 25 and FIGS. 26g-26l. Notably, in PC12 cells treated with 1E+9 VG, conjugation of IB4 to AAV9 increased efficiency by 9 fold, while at 5E+9 VG the increase was 84 fold compared to wild type.

Example 8. Influence of Linker Length on Transduction Efficiency

Methods
AAV Production

Recombinant AAV2-• HSPG was prepared in accordance with the procedure described in Example 1.

Chemical Modification and Coupling of IB4 to AAV2-• HSPG

IB4 (8.8 nmol) was reacted with 20-fold molar equivalent of Azido-PEGn-NHS ester (176 nmol) in PBS at pH7.2 for 3 hours at room temperature. Unreacted azido groups were removed using a 10 KDa molecular MWCO centrifugal filter. To conjugate to AAV, 6E+12 purified AAV2-• HSPG was reacted with 0.17 nmol, 0.52 nmol, 1.73 nmol or 5.2 nmol DBCO in PBS pH7.2 for 3 hours at room temperature. The reaction was purified using a 100 KDa MWCO centrifugal filter, and further incubated with 0.1 nmol IB4-PEG4-Azide overnight at room temperature. Excess unreacted IB4 was removed by passing through a 100 KDa MWCO centrifugal unit twice, and modified AAV was resuspended in PBS.

The following linker combinations in Table 2 were investigated (and commercial source of molecule):

TABLE 2

|  | Azido-PEGn-NHS (L) | DBCO-PEGn-NHS (V) | Total PEGn | GFP fluorescence images |
|---|---|---|---|---|
| No spacer | 0 (from Thermo) | 0 (from Sigma) | 0 | FIGS. 26a-d |
| Short | 2 (from Broadpharm) | 1 (from Broadpharm) | 3 | FIGS. 27a-d |
| Medium | 4 (from Thermo) | 4 (from Sigma) | 8 | FIGS. 28a-d |
| Long | 8 (from Sigma) | 8 (from Broadpharm) | 16 | FIGS. 29a-d |

In Vitro Application to PC12 Cells

PC12 cells were maintained at 37° C. in DMEM/F12 medium containing 5% horse serum 5% fetal bovine serum, and 100•U of penicillin/streptomycin. IB4::AAV2-• HSPG particles conjugated at different molar ratios and varying linker lengths were incubated with PC12 cells in PBS for 2 hours. Media was then replaced and cells were maintained at 37° C. for 5 days before fixation in 4% PFA, labelling with DAPI and imaging with a Zeiss AxioObserver A1 microscope. Images were analyzed by measuring the GFP fluorescence in each DAPI positive cells and plotting as the mean+/−SEM for each titer. See FIG. 30.

Results and Interpretation

In these experiments we investigated the influence of linker length (i.e., no. ethylene glycol monomer spacers) on transduction efficiency. We selected PC12 cells as a target cell line because they are difficult to transduce using standard AAV vectors (thus reducing background), and IB4 as a targeting ligand because it binds strongly to these cells. We performed experiments for 4 different linker lengths, and measured efficiency of each linker using a range of molar ratios. The reasoning here was that each linker may react differently with the virus or ligand, and that by using a range of modification ratios we would be able to capture any variations in reaction efficiency and ultimately transduction efficiency of the final constructs.

From looking at the data plotted in FIG. 31, it is clear that having no spacer between AAV and ligand has a strong negative impact upon transduction efficiency. Very few cells were transduced with surface modified capsids produced with 0.17 nmol, 0.52 nmol and 1.73 nmol NHS-DBCO, and only at 5.2 nmol do we observe appreciable infection. This is interesting because it shows that even in the absence of any spacer between ligand and virus, it is still possible to transduce cells. However, this requires high concentrations of NHS-DBCO to AAV for preparation of the construct. Without being bound by theory, one possibility is that perhaps the crosslinking reaction between the targeting ligand-Azide and AAV-DBCO is limited by steric hindrance and that optimal deposition of DBCO groups on the virus is required for the reaction to proceed. The short total PEGn=3 PEG spacer performed better than no spacer at all, but again, at low molar ratios (0.17 nmol) efficiency was reduced. Interestingly, at higher modification ratios, this spacer length performed moderately better than all the others. Constructs with medium (n=8) and long (n=16) spacers performed similarly and showed higher transduction efficiencies when produced at the molar ratio of 3E+9 VG of virus to 0.17 nmol linker, of AAV:ligand. These data suggest that increasing spacer length within this range increases transduction efficiency, especially at sub-optimal modification ratios.

Example 9. Size Limits of PEG Linkers

The impact on AAV transduction efficiency in PC12 cells of AAV constructs comprising discrete PEG (dPEG) and disperse PEG (pPEG) spacers providing various linker lengths was investigated. To that aim, we surface modified the AAV2•HSPG capsid with WGA ligand by combining (i) the capsid functionalized with a capsid reactive linker selected from either DBCO-PEGn-NHS (where n is 4, 12, about 45 (dPEG 2K), about 114 (dPEG 5K), about 228 (dPEG10K), about 682 (dPEG 30K) or DBCO-PEGn-TFP (where n is 24), with (ii) the WGA ligand functionalized with a ligand reactive linker: Azide-PEGn-NHS (where n is 4, 12, 24 or about 114 (dPEG 5K)). The constructs corresponding to the various linkers/PEG spacers that were investigated are further illustrated in Table 3 where the capsid reactive linker is DBCO-PEGn-NHS unless denoted with "TFP".

nmol of the selected reactive linker in PBS pH7.2 for 3 hours at room temperature. Next, each obtained surface functionalized capsid was incubated with 0.1 nmol of WGA-PEGn-Azide (the functionalized targeting ligand) for one hour at room temperature and overnight at 4° C. to obtain the various WGA-AAV2• HSPG surface modified constructs.

In Vitro Application to PC12 Cells

PC12 cells were maintained at 37° C. in DMEM/F12 medium containing 5% horse serum 5% fetal bovine serum, and 100•U of penicillin/streptomycin. PC12 cells were incubated with 3E+9 VG of the various WGA-AAV2ΔHSPG constructs in PBS for 2 hours. Media was then replaced and cells were maintained at 37° C. for 5 days labelling with Hoechst and imaging with a Zeiss AxioObserver A1 microscope. Images were analyzed by measuring the GFP fluorescence in each Hoechst positive cell and plotted as the mean+/−SEM for each titer.

Results

Together, the data illustrated in FIGS. 32-36 demonstrate that the size of PEG linker used to modify the virus is

TABLE 3

Surface modified virus constructs prepared with various PEGn spacers present on the ligand reactive linker (L) and capsid reactive linker (V)

| FIG. 32: | | PEGn (L) | PEGn (V) | Total length (no. of ethylene glycol monomers) (approximate when underlined) |
|---|---|---|---|---|
| a | dPEG4 + dPEG4 | 4 | 4 | 8 |
| b | dPEG12 + dPEG4 | 12 | 4 | 16 |
| c | dPEG24 + dPEG4 | 24 | 4 | 28 |
| d | dPEG4 + dPEG12 | 4 | 12 | 16 |
| e | dPEG12 + dPEG12 | 12 | 12 | 24 |
| f | dPEG24 + dPEG12 | 24 | 12 | 36 |
| g | dPEG4 + dPEG24 | 4 | 24 (TFP) | 28 |
| h | dPEG12 + dPEG24 | 12 | 24 (TFP) | 36 |
| i | dPEG24 + dPEG24 | 24 | 24 (TFP) | 48 |
| j | dPEG4 + pPEG2K | 4 | 2KD (45)* | <u>49</u> |
| k | dPEG4 + pPEG5K | 4 | 5KD (114)* | <u>118</u> |
| l | dPEG4 + pPEG10K | 4 | 10KD (228)* | <u>232</u> |
| m | dPEG4 + pPEG30K | 4 | 30KD (682)* | <u>686</u> |
| n | pPEG5K + dPEG4 | 5KD (114)* | 4 | <u>118</u> |
| o | pPEG5K + pPEG2K | 5KD (114)* | 2KD (45)* | <u>159</u> |
| p | pPEG5K + pPEG5K | 5KD (114)* | 5KD (114)* | <u>228</u> |
| q | pPEG5K + pPEG10K | 5KD (114)* | 10KD (228)* | <u>342</u> |
| r | pPEG5K + pPEG30K | 5KD (114)* | 30KD (682)* | <u>796</u> |

*polydisperse PEG size is provided as an average molecular weight. In parenthesis is the corresponding average number of ethylene glycol monomers.

Methods

Recombinant AAV2-• HSPG was prepared in accordance with the procedure described in Example 1.

Chemical Modification and Coupling of WGA to AAV2• HSPG with Different Linkers

WGA (1.7 nmol) was functionalized by reaction with 20-fold molar equivalent of the ligand reactive linker Azide-PEGn-NHS (54 nmol) (where n is 4, 12, or 24) in 100 ul PBS at pH 7.2 for 3 hours at room temperature. Unreacted linker was removed using a 10 KDa molecular MWCO centrifugal filter. To conjugate the functionalized ligand to AAV, first a surface functionalized AAV capsid was prepared for each capsid reactive linker: DBCO-PEGn-NHS (where n is 4, 12, or 24) and DBCO-PEGn-TFP (where n is 4, 12, or 24). The transduction efficiency of each capsid/ligand construct was optimized by preparing each construct at a range of capsid to ligand ratios. Specifically, each surface functionalized AAV capsid was prepared by reacting 3E+9 VG purified AAV2• HSPG with 0.17 nmol, 0.52 nmol, 1.73 nmol and 5.2 important to control in order to achieve the desired boost in transduction efficiency and appears to be optimal in the tested system around PEG12. On the ligand side, longer linkers appear to be tolerated, including disperse PEG 5000, but are not ideal.

FIGS. 32a-s are images of the Hoechst labeled PC12 cells treated with each of the prepared WGA-AAV2• HSPG surface modified constructs. As shown in FIGS. 32a-s and in FIGS. 33-36, the brightest images, indicating most efficient transduction, were obtained in the experiments where the linkers comprise various PEG lengths (i.e., ethylene glycol monomers) having "n" in the range from 4-24 (or 4-12) and where the entire linker comprises a total "n" of 8 to 24 (or 8-16) PEG units. The optimal combination was DBCO-PEG4 on the virus and Azide-PEG4 on the ligand (total n=8) (FIG. 32a), followed by DBCO-PEG12 on the virus and Azide-PEG4 on the ligand (total n=16) (FIG. 32d), DBCO-PEG4 on the virus and Azide-PEG12 on the ligand (total n=8) (FIG. 32b), and DBCO-PEG12 on the virus and Azide-PEG12 on the ligand (total n=24) (FIG. 32e). The only condition using dispersed PEGs that showed some signal was WGA-Azide-PEG 5000 reacted with DBCO-PEG4 in the virus (FIG. 32n). The discrete PEG 4L+4V and 12L+12V combinations clearly perform better than longer disperse pPEG.

FIG. 33 and FIG. 34 further confirm the boost to individual and mean (respectively) cell transduction efficiency of PC12 cells treated with AAV2ΔHSPG virus constructs surface modified with WGA having discrete PEG linker spacers (i.e., ethylene glycol monomers) where total n (sum of PEG monomers in linker formed between the viral capsid and the ligand is between 8 and 24.

FIGS. 35 and 36 compare the mean transduction efficiency for selected discrete and dispersed PEG combinations compared to unmodified virus. In FIG. 35, it can be seen that the discrete PEG 4L+4V and 12L+12V combinations clearly perform better than longer disperse PEG spacers. FIG. 36 focuses on only the poorest performing discrete and dispersed PEG combinations. Interestingly, only 5KL+4V performs better than control, suggesting that limited spacer length on the virus side of the linker may be helpful to obtain the desired boosted transduction, while the spacer length on the ligand side of the linker may be more amenable to the use of longer spacers.

Example 10. DBCO-Azide Crosslinker Reactive Pair Performs Best for WGA-AAV2• HSPG Construct We next investigated whether different linker chemistries would improve AAV transduction efficiency in PC12 cells beyond the DBCO-Azide chemistry we have already explored. To this aim we prepared AAV2• HSPG-WGA constructs using TCO/Tetrazine ligation and, separately, Phosphine-NHS/Azide crosslinker reactive pairs that react via Staudinger ligation.

The TCO/tetrazine ligation chemistry is based on an inverse-demand Diels-Alder cycloaddition reaction between a trans-cyclooctene and tetrazine reaction pair, forming a dihydropyridazine bond and is known to possess ultrafast kinetics (>800 M-1 s-1) unmatched by any other bioorthogonal ligation pair.

NHS-Azide and NHS-Phosphine bi-functional linkers comprise the NHS ester that are amine-reactive and suitable for derivatizing primary amines of proteins. Once a protein (capsid or ligand) is azide- or phosphine-functionalized, the two components are mixed for effective and stable conjugation. Phosphine groups react with azides via a Staudinger reaction to produce an aza-ylide intermediate that is trapped to form a stable, covalent amide bond.

Methods

Recombinant AAV2-• HSPG was prepared in accordance with the procedure described in Example 1.

To prepare the functionalized targeting ligands used in these experiments, 150 mM stock solutions of Tetrazine-PEG5-NHS and Azido-PEG4-NHS were prepared in DMSO. WGA (27 uM, 1 mg/ml) was reacted with 20-fold molar equivalent of Tetrazine-PEG5-NHS (540 uM) or Azido-PEG4-NHS (540 uM) in PBS at pH7.2 for 3 hours at room temperature. Unreacted linkers were removed using a 10 KDa molecular MWCO centrifugal filter.

To prepare the surface functionalized viral capsids for use in these experiments: 20 mM TCO-PEG4-NHS or Phosphine-NHS stock solution were prepared in DMSO. To surface modify the AAV capsid, 3E+9 VG purified AAV2• HSPG was reacted with 0.17 nmol, 0.52 nmol, 1.73 nmol and 5.2 nmol TCO-PEG4-NHS or Phosphine-NHS in 20 ul PBS pH7.2 for 3 hours at room temperature. The TCO or Phos surface modified AAV is then incubated with 0.1 nmol of WGA-PEG5-Tetrazine or WGA-PEG4-Azide, respectively, for one hour at room temperature and then overnight at 4° C.

In Vitro Application to PC12 Cells

PC12 cells were maintained at 37° C. in DMEM/F12 medium containing 5% horse serum 5% fetal bovine serum, and 100•U of penicillin/streptomycin. PC12 cells were incubated with WGA-AAV2• HSPG constructs prepared at the various AAV:linker ratios described above in PBS for 2 hours. Media was then replaced and cells were maintained at 37° C. for 5 days labelling with Hoechst and imaging with a Zeiss AxioObserver A1 microscope. Images were analyzed by measuring the GFP fluorescence in each Hoechst positive cells and plotting as the mean+/−SEM for each titer.

Results

Figure 37:
Figure 40:
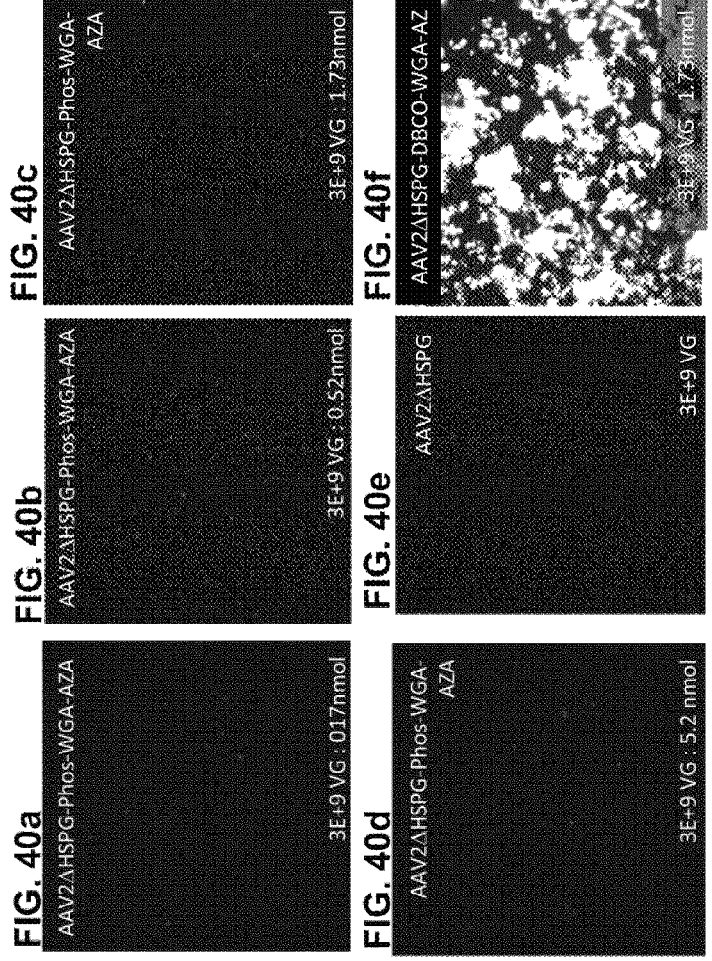

As shown in FIGS. 37a-37f and FIGS. 38-39, a very low level of tdTomato fluorescence was detected in cells treated with AAV2• HSPG conjugated with WGA using TCO/Tetrazine ligation, indicating inefficient transduction. Slightly more transduction was evident in cells treated with AAV2• HSPG conjugated with WGA using Phosphine-NHS/Azide (FIG. 40a-40d and FIGS. 41-42); however, observed transduction was only minimally improved when compared to unmodified AAV2• HSPG (FIGS. 37e and 40e). The chemical modification that shows the highest transduction efficiency remains the AAV constructs prepared using the DBCO-Azide crosslinker reactive pair (FIGS. 37f and 40l).

Example 11. Quantification of AAV Particles and Chemical Modification on the Virus Surface Background In order to quantify the extent of surface modification of an AAV capsid, we used a standard AAV9 (purchased from Innovavector) with known concentration of capsids. Using this standard we then quantified the extent of modification using two strategies: (1) We reacted NHS-PEG4-DBCO with the virus, and from the absorbance of the DBCO chromophore calculated the number of DBCO molecules per capsid. We then conjugated WGA-PEG4-Azide to the modified AAV9, and from the reduction in DBCO absorbance, calculated the number of ligands per capsid. (2) We conjugated a fluorescently labelled Azido ligand (WGA-SNAP-TMR-PEG4-Azide) to the virus to assess the number of ligands per virus, again using absorbance measurements.

Methods

Modification of AAV9 with DBCO and then Crosslinked with WGA Azido 3.6E+10 VG AAV9 were incubated with 52 nmol of DBCO-PEG4-NHS in a final volume of 97 ul for 3 hours on the shaker at RT. This quantity of linker was selected because it gave optimal transduction efficiencies when conjugated to AAV9 and applied to PC12 cells.

In order to modify the virus with a WGA-Azido ligand, 2.8 nmol of WGA were reacted with 20-fold molar equivalent of Azido-PEG4-NHS ester (56 nmol) in a final volume of 100 ul of PBS at pH7.2 for 3 hours at room temperature (RT). Following, the unreacted Azido groups were removed using a 10 KDa molecular MWCO centrifugal filter. Afterwards, 242.5 nmol of WGA-Azido were added and incubated for 1 hour at RT. After the modification, the samples were rinsed three times using Pluronic F68 0.001% NaCl 200 mM in PBS with 100 KDa molecular MWCO in order to remove the excess unbound reagents. The 20 ul collected from the columns were concentrated by speed vacuum and resuspended in 10 ul Pluronic F68 0.001% NaCl 200 mM in PBS. In addition to reacting with WGA-Azido, we had another two groups 1) AAV9 alone and 2) AAV9 incubated only with DBCO. To correct for loss of virus during the reaction and cleanup, 5 ul of sample were used to run a ddPCR analysis.

Assessment of Degree of PEG4-DBCO and WGA-PEG4-Azido Chemical Modification on the Virus Absorbance was measured at a wavelength of 307 nm, which is the peak of absorbance of the chromophore embedded in the DBCO. Reaction between AAV9-PEG4-DBCO and WGA-PEG4-Azido should lead to a loss of the chromophore present in the DBCO, thus the difference from the total number of PEG4-DBCO molecules in the sample PEG4-DBCO and PEG4-DBCO+ WGA-PEG4-Azide should provide the number of ligand molecules bound to the virus.

The raw data were processed as following:
calculation of the total number of PEG4-DBCO molecules based on sample absorbance (corrected for absorbance of AAV9 alone and residual absorbance of unreacted NHS-PEG4-DBCO after reaction cleanup) using a standard curve of absorbance vs concentration of PEG4-DBCO;
calculation of the number of PEG4-DBCO molecules on each capsid by dividing the number of total DBCO molecules by the number of total capsids;
calculation of the number of ligand molecules bound to the virus by subtracting the number of PEG4-DBCO molecules present in the sample PEG4-DBCO+WGA-PEG4-Azido from the sample PEG4-DBCO only.

Modification of Virus with Fluorescently Labelled Ligands

In order to modify the virus with a fluorescently labelled ligand, 2.8 nMol of WGA-SNAP were reacted with 20-fold molar equivalent of Azido-PEG4-NHS ester (56 nMol) in a final volume of 100 ul of PBS at pH7.2 for 3 hours at room temperature (RT). Unreacted Azido groups were removed using a 10 KDa molecular MWCO centrifugal filter. Fluorescent BG-Tetramethylrhodamine (BG-TMR, from NEB) was then incubated at equimolar concentrations with WGA-SNAP Azido for 1 hour at RT to obtain WGA-SNAP-TMR-PEG4-Azide.

To modify the virus with WGA-SNAP-TMR-PEG4-Azide, 3.6E+10 VG AAV9 were incubated with 52 nmol of DBCO-PEG4-NHS in a final volume of 97 ul for 3 hours on the shaker at RT. Afterwards, 242.5 nmol of WGA-SNAP-TMR-PEG4-Azide were added and incubated for 1 hour at RT. As controls we used 1) AAV9 alone; 2) AAV9 incubated only with TMR-WGA-Azido without any DBCO-PEG4-NHS linker; and 3) AAV9 incubated with WGA-Azido. After the modification, the samples were rinsed three times using Pluronic F68 0.001% NaCl 200 mM in PBS with 100 KDa molecular MWCO in order to remove the excess unbound reagents. The 20 ul collected from the columns were collected for absorbance measurements and ddPCR analysis.

Assessment of number of fluorescent ligands per AAV9 capsid.
Absorbance was measure at a wavelength of 544 nm, which is the peak of absorbance of TMR. The raw data were processed as following:
calculation of total number of TMR molecules based on absorbance and extinction coefficient of TMR by subtracting absorbance values of AAV9 alone from the total absorbance values of AAV9-PEG4-DBCO:: WGA-SNAP-TMR-PEG4-Azide;
calculation of number of TMR molecules (thus ligand molecules) on the capsid, dividing the number of total TMR molecules by the number of total capsids;

Results

Based on the absorbance of DBCO, we calculated the number of PEG4-DBCO molecules per virus to be around 210, while the number of WGA-PEG4-Azide ligands was approximately 150 molecules per capsid (FIG. 43). From measurements with the fluorescent WGA-SNAP-TMR-PEG4-Azide, we estimated the number of ligands to be 170 molecules per capsid (FIG. 44). The numbers obtained with both strategies fit with the fact that the most abundant AAV capsid protein VP3 (50 copies of VP3 per virion), has 10 lysines exposed, which means approx. 500 binding sites for the linker DBCO-PEG4-NHS, therefore for the ligand.

Example 12. Increased Infectivity of Clinically Relevant Capsids

Methods
AAV Production

Recombinant AAV3 and AAV8 with a GFP cargo were purchased from Innovavector, while AAV5 with a tdTomato cargo, was purchased from Addgene (plasmid #59462). AAV6 with a tdTomato cargo was produced in HEK293T as described previously (Grieger 2006, Wu 2018). Cells were harvested 5 days post infection, lysed with Triton X-100 at 0.5%, nuclease treated, concentrated by tangential flow filtration, and purified using isopycnic ultracentrifugation (Dias 2015). Vector genome titration was performed using Q-PCR with primers targeting the promoter region of the viral cargo (Grieger 2006).

Chemical Modification and Coupling of WGA to AAV3, AAV5, AAV6 and AAV8

WGA (1.7 nmol) was reacted with 20-fold molar equivalent of Azido-PEG4-NHS reactive linker (54 nmol) in 100 ul PBS at pH7.2 for 3 hours at room temperature to produce the functionalized targeting WGA ligand. Unreacted reactive linker was removed using a 10 KDa molecular MWCO centrifugal filter. To conjugate to AAV, 3E+9 VG each of purified AAV3, AAV5, AAV6, and AAV8 were reacted with 0.17 nmol, 0.52 nmol, 1.73 nmol and 5.2 nmol DBCO-PEGn-NHS in 20 ul PBS pH7.2 for 3 hours at room temperature to identify the optimized capsid to linker ratio to form the surface functionalized viral capsids. Each obtained surface functionalized viral capsid products was then incubated with 0.1 nmol of WGA-PEG4-Azide for one hour at room temperature and overnight at 4° C. to produce a corresponding WGA surface modified viral capsid.

In Vitro Application to PC12 Cells

PC12 cells were maintained at 37° C. in DMEM/F12 medium containing 5% horse serum 5% fetal bovine serum, and 100•U of penicillin/streptomycin. PC12 cells were incubated with 3E+9 VG of each of the WGA surface modified viral capsid products prepared as described above in PBS for 2 hours. Media was then replaced and cells were maintained at 37° C. for 5 days before fixation in 4% PFA, labelling with DAPI and imaging with a Zeiss AxioObserver A1 microscope. Images were analyzed by measuring the GFP fluorescence in each DAPI positive cells and plotting as the mean+/−SEM for each titer.

Results

PC12 cells are difficult to transduce using wildtype AAV serotypes such as AAV3, AAV6 and AAV8. We therefore asked whether conjugation of these AAVs serotypes to WGA would increase AAV transduction efficiency in this cell type, boosting the virus infection compared to unmodified wild-type virus. As shown in FIGS. 45a, 51a and Ma, we were unable to detect GFP or RFP/tdTomato fluorescence in cells treated with unmodified wild type AAV serotypes AAV3, AAV6 and AAV8. In contrast, surface modification of serotypes AAV3, AAV6 and AAV8 with WGA increased transduction efficiency substantially (FIGS. 45b-45e, FIGS. 46-47, FIGS. 51b-51e, FIGS. 52-53, FIGS. 54b-54e, and FIGS. 55-56) such that transduced positive cells were evident for all serotypes at different reactive linker molar quantities.

PC12 cells treated with wildtype AAV5 displayed a higher transduction level (FIG. 48a) than AAV3, AAV6 and AAV8. Surface modification of AAV5 with WGA according to the present disclosure increased transduction efficiency substantially (FIGS. 48b-48e). Cells exhibited increasing numbers of tdTomato positive cells for all surface modified viral capsid products that were prepared with different molar quantities of reactive linker (FIGS. 49-50).

Example 13. Requirement of AAVR for Internalization of Modified Vectors

Methods
Generation of AAVR KO HEK293 cells
The AAV receptor (AAVR) gene (KIAA0319L) was knocked out in HEK293 cells using the CRISPR-Cas9 technology. Briefly, HEK293 cells were transfected with spCas9 and gRNA (ATAGGTGTAACTACGTCACT) (SEQ ID NO: 1) plasmids containing puromycin and hygromycin selection cassettes. Cells were grown in HEK293 medium with puromycin and hygromycin. After expansion, AAVR2 knock out (KO) HEK293 cells were selected by Fluorescence Activated Cell Sorting (FACS) upon infection with AAV2 eGFP. The cells negative for eGFP fluorescence were enriched and further expanded in puromycin and hygromycin-medium. HEK293 cells were infected with AAV2 eGFP, FACS purified, and expanded for four times in total.
Surface Modification and Crosslinking of WGA to AAV2
Targeting ligand WGA (1.7 nmol) was reacted with 20-fold molar equivalent of reactive linker Azide-PEG4-NHS (54 nmol) in 100 ul PBS at pH7.2 for 3 hours at room temperature to form the functionalized targeting ligand. Unreacted reactive linker was removed using a 10 KDa molecular MWCO centrifugal filter. To conjugate the functionalized targeting ligand to AAV2, 1E+9 VG purified AAV2 was reacted with 0.17 nmol DBCO-PEG4-NHS in 20 ul PBS pH7.2 for 3 hours at room temperature. The obtained surface functionalized viral capsid was incubated with 0.1 nmol of WGA-PEG4-Azide for one hour at room temperature and overnight at 4° C. to produce the "WGA-AAV2" surface modified viral capsid.
In Vitro Application to AAVR KO HEK293 Cells
WGA-AAV2 or unmodified AAV2 was added to AAVR KO HEK293 at a titer of 1E+9 VG. 5 days post transduction, the cells were imaged and quantified with ImageJ open source software.
Results
In these experiments we wished to investigate whether AAV vectors having surfaces modified in accordance with the present disclosure can bypass the requirement of the AAVR receptor for cell entry and transduction. To achieve this, we generated a HEK293 cell line in which the AAVR gene was deleted. In normal HEK293 cells, we observed robust transduction by AAV2 as shown by the FACS analysis (FIG. 57) and microscopy (FIG. 58a). In AAVR KO HEK293 cells transduction by AAV2 tdTomato was dramatically reduced (FIG. 58b).

We further investigated whether the ligand WGA is sufficient to rescue AAV2 entry into the AAVR KO cells. We found that WGA-AAV2 infection led to a significantly higher number of both percentage and mean fluorescence intensity (MFI) of tdTomato positive cells compared to the control (AAV2 unmodified) (FIGS. 59a-b and FIGS. 60a-b). This indicates that modification of AAV2 with WGA enables the vector to enter cells even in the absence of AAVR, suggesting that it is bypassing AAVR mediated internalization.

Example 14. ScFv Targeting with Nemolizumab-SNAP-AAV2• HSPG

Methods
AAV Production
Recombinant AAV2-• HSPG was prepared in accordance with the procedure described in Example 1.
Production of Nemolizumab-SNAP
The amino acid sequence of nemolizumab was obtained from the IMGT/3D structure database (imgt.org/3Dstructure-DB/cgi/details.cgi?pdbcode=10064) (SEQ ID NO: 2). The CDRs were cloned into a scFv backbone containing an upstream GP64 signal sequence, and downstream Sortag, SNAP-tag and 6×His tag (SEQ ID NO: 3), illustrated in (FIG. 61). This was cloned into pFastBac for production using the baculovirus expression system. Protein was produced in SF9 insect cells using standard methods and purified from cell media using affinity chromatography.
Surface Modification and Crosslinking of AAV2-• HSPG and Nemolizumab-SNAP
3E+10 VG of purified AAV2-• HSPG was reacted with 17.3 nmol BG-PEG13-NHS (custom synthesis) in 200.1 PBS pH7.2 for 3 hours at room temperature to produce the BG-functionalized viral capsid. The reaction was purified using a 100 KDa MWCO centrifugal filter, and further incubated with 1 nmol Nemolizumab-SNAP functionalized ligand overnight at room temperature to produce the "Nemolizumab-SNAP::AAV2-• HSPG" surface modified viral capsid. Excess unreacted ligand was removed by passing through a 100 KDa MWCO centrifugal unit twice, and the surface modified viral capsid was resuspended in PBS.
In Vivo Injections and Tissue Processing
For in vivo injection experiments, wildtype mice were anesthetized with 2-2.5% Isoflurane, and then 3E+10 VG of Nemolizumab-SNAP::AAV2-• HSPG in 10 ul of PBS was injected subcutaneously into the ear. 3 weeks later, skin was harvested, fixed in 4% paraformaldehyde overnight and sectioned at 40 m. Sections were stained overnight at 4° C. with rabbit anti-K14 (Covance 1:200 dilution) in PBS containing 5% goat serum+0.3% Triton-X. Secondary anti-rabbit Alexa488 antibody was diluted 1:1000 and incubated for 2 h at room temperature in the dark. Slides were mounted with prolong gold and Images were taken with a Leica SP5 confocal microscope and analyzed in ImageJ software.
Results
Nemolizumab was selected as a scFv because it is specific for IL31RA receptors and has shown some promise in clinical trials for moderate to severe atopic dermatitis (1). Nemolizumab-SNAP::AAV2-• HSPG was injected subcutaneously in mice and skin sections examined for overlap with K14, a marker of keratinocytes. As shown in FIGS. 62a, 62b and 62c, we observed substantial overlap between virally infected cells and K14 positive keratinocytes around hair follicles. Importantly, because fluorescence persisted for longer than the 8-10 day epidermal turnover in mice (2), our data indicate that epidermal stem cells are also being targeted in this experiment. Indeed, transcriptomics studies indicate that IL31RA is expressed in basal keratinocytes in the interfollicular and follicular epidermis, many of which are epidermal stem cells (3).

REFERENCES

1. Nemoto O, Furue M, Nakagawa H, Shiramoto M, Hanada R, Matsuki S, et al. The first trial of CIM331, a humanized antihuman interleukin-31 receptor A antibody, in healthy volunteers and patients with atopic dermatitis to evaluate safety, tolerability and pharmacokinetics of a single dose in a randomized, double-blind, placebo-controlled study. The British journal of dermatology 2016; 174:296-304
2. Potten C S, Saffhill R, Maibach H I. Measurement of the transit time for cells through the epidermis and stratum corneum of the mouse and guinea-pig. Cell Tissue Kinet 1987; 20:461-72
3. Joost S, Zeisel A, Jacob T, Sun X, La Manno G, Lonnerberg P, et al. Single-Cell Transcriptomics Reveals that Differentiation and Spatial Signatures Shape Epidermal and Hair Follicle Heterogeneity. Cell Syst 2016; 3:221-37 e9

Example 15. Investigation of Immune Stealth—Evasion of Neutralizing Antibodies

Neutralizing antibodies recognizing AAV capsid proteins are major hurdles in AAV-mediated gene therapy. Currently, patients testing positive for even low titers of anti-AAV neutralizing antibodies are excluded from clinical trials using AAV as gene therapy vectors. Since approximately 50% of the population has neutralizing antibodies against AAV from a young age, finding a way to evade/circumvent humoral immunity would constitute a significant benefit by enlarging the pool of eligible patients. Currently much research in the field focuses on the aspect of immune evasion (Wang M, et al. Prediction of adeno-associated virus neutralizing antibody activity for clinical application. *Gene Ther.* 2015 December; 22(12):984-92). We hypothesized that surface modification of AAV with the reactive linkers described herein, or linkers and ligands together, could lead to reduced recognition by neutralizing antibodies.

The impact of (i) functionalizing the virus with different amounts of reactive linker and (ii) the length of linker on either the Virus side only or on both the Ligand and the Virus side on humoral immunity to AAV was investigated in vitro. To test the first, human IgG binding to and neutralization of wild type AAV2 functionalized with different molar quantity of linker with a fixed length spacer, but in the absence of ligand, was tested. For the second, human IgG binding to and neutralization of AAV2 functionalized with a fixed amount of discrete PEG (dPEG) and disperse PEG (pPEG) spacers, and either left unconjugated or conjugated to WGA also functionalized with a fixed amount of discrete PEG (dPEG) and disperse PEG (pPEG) spacers was tested. Neutralization was tested on cells lines or primary cells differently permissive to wild type AAV2 infection.

Materials

AAV Vectors

Recombinant AAV2 with a tdtomato cargo was produced in HEK293T cells. Cells were harvested 3 days post transfection, lysed with Triton X-100 in the presence of RNase. Recombinant AAV2 was concentrated by tangential flow filtration, and purified using isopycnic ultracentrifugation (Grieger 2006). AAV titration was performed using qPCR with primers targeting the ITR region of the viral cargo (Dias 2015).

Human Pooled Serum and Mouse Serum

Human pooled serum was purchased from Sigma (Cat. Nr.: H4522-20ML). Human serum was heat-inactivated to inactive complement or other non-antibody viral inhibitory factors, and stored frozen for further use. Mouse serum was collected from mice 4 weeks after a systemic injection of AAV2. Blood was collected from the tail vein and left at room temperature for 30 min to clot. The clot was removed by a centrifugation step at 2000 g for 10 min in a pre-cooled centrifuge. The supernatant, which consists of serum, was collected and heat-inactivated for 30 min at 56° C. Serum was stored at −20° C. until use.

Methods

Surface Modification of Virus (AAV2) with BCO-PEG(12)-NHS Linkers Using Different Virus to Reactive Linker Ratios As done in previous experiments, 0.52 nmol, 1.73 nmol, 5.2 nmol, 17.3 nmol, 52 nmol or 173.3 nmol DBCO-PEG (12)-NHS linkers were conjugated to 3E+9 VG AAV2 in 20 ul PBS, pH7.2 for 3 hours at room temperature.

Crosslinking PEG(n)-Azide-NHS Functionalized WGA with DBCO-PEG(n) Functionalized AAV2 Exploring PEG Lengths Similar to Example 9, wild AAV2 capsid was functionalized with a capsid reactive DBCO-PEGn-NHS linker where n is either 4 or 2k to produce the "4 virus" or the "5k virus" construct respectively. WGA ligand functionalized with a ligand reactive Azide-PEGn-NHS linker where n is 4 or 5K to produce the "4 ligand" or "5k ligand" respectively. Specifically, WGA (1.7 nmol) was reacted with 20-fold molar equivalent of Azide-PEGn-NHS (54 nmol) in 100 ul PBS at pH7.2 for 3 hours at room temperature. Unreacted linker was removed using a 10 KDa molecular MWCO centrifugal filter. 0.1 nmol of WGA-PEG(n)-Azide were combined with the surface modified virus in the crosslinking reaction for 1 hour at room temperature and further overnight at 4° C.

ELISA

AAV2-specific IgG antibodies were detected using an enzyme-linked immunosorbent assay (ELISA). 96-well ELISA plates were coated with AAV2 particles diluted in coating buffer (37 mM $Na_2CO_3$, 63 mM $NaHCO_3$ in $H_2O$; pH 9.6) at a concentration of 1×10^9 vg/well for 2 hours at room temperature or overnight at 4° C. Plates were washed three times with washing buffer (PBS with 0.05% Tween20). Blocking solution (PBS with 0.05% Tween20 and 5% non fat dry milk) was added sand plates were incubated for 2 hours at 37° C. After blocking plates were washed once with washing buffer. Serum dilutions were added to the wells and incubated for 2 hours at room temperature or overnight at 4° C. Plates were washed with washing buffer three times and incubated with an HRP-conjugated secondary antibody against IgG diluted in dilution buffer (PBS with 0.05% Tween20 and 1% non fat dry milk) for 1 hour at 37° C. Plates were washed three times with washing buffer and TMB, a substrate for HRP, was added. To stop the reaction a stop solution containing acidic acid was added and absorbance (expressed as optical density units, OD) was measured at 450 nm with a spectrophotometer. OD values are reported after subtracting background and correlate with degree of binding of antibodies to the immobilized antigen (AAV).

Neutralization Assay with HEK293T Cells (Permissive Cell Line)

HEK293T cells were maintained in DMEM+ Glutamax, supplemented with 5% FBS and 100 U of penicillin/streptomycin, at 37° C. and 5% $CO_2$. For the assay, cells were seeded at 3×10^4 cells per 96-well and AAV virus, pre-incubated for 1 hour at 37° C. with 2-fold serial dilutions of human or mouse serum, was added at a MOI of 1000. After 72 hours the fluorescence of the transduced cells was analyzed by flow cytometry with a S3e Cell Sorter from BioRad.

Neutralization Assay with PC12 Cells (Poorly Permissive Cell Line)

PC12 cells were maintained in DMEM/F12 medium, supplemented with 10% horse serum, 5% FBS and 100 U of penicillin/streptomycin, at 37° C. and 5% $CO_2$. For the assay, cells were seeded at 3×10^4 cells per 96-well and AAV virus, pre-incubated for 1 hour at 37° C. with 2-fold serial dilutions of mouse serum, was added at a MOI of 1000. After 5 days the fluorescence of the transduced cells was acquired with a Zeiss AxioObserver A1 microscope.

Neutralization Assay with Primary Dorsal Root Ganglia (DRG) Neurons

Glass-bottom dishes were coated with a 15 •1 drop of poly-L-lysine solution (stock conc.: 1 mg/ml, diluted 1:10 with $H_2O$) for 1 hour at 37° C. After 1 hour the drop was removed and the dishes were washed twice with PBS. Then, 15 •1 of Matrigel, diluted 1:50 in PBS were added to the dishes and incubated at 37° C. Before seeding the cells the Matrigel drop was removed and the dishes were air-dried. Subsequently DRGs were isolated from adult mice. Primary cells (primarily neurons and satellite cells) were further isolated by collagenase treatment of DRG at 37° C. for 25 min followed by washing and an incubation step with trypsin. The reaction was stopped with 500 •1 of complete medium and the cell suspension was filtered, centrifuged and resuspended in cell culture medium. 10 •1 of the cell suspension were added to each dish. After 1 hour 100 •1 of medium was gently. On the next day the medium was removed and 200 •1 of fresh medium were added to the dishes. The next day the medium was changed to 100 •1 of DMEM+Pen/Strep without FBS. After 15 min the serum-free medium was removed and the unmodified and PEG4-DBCO:Azide-PEG4-WGA modified virus, which were pre-incubated with serum, were added to the cells and 15 min later 50 •1 of medium was added. On the next day 2 ml of DMEM/F12 medium was added to each dish. Imaging of the transduced cells was performed after five days with a confocal microscope.

Results

In FIGS. 63a and 63b, we chemically modified AAV2 with different amount of linkers DBCO-PEG4 and performed an ELISA with human pooled serum, which contains antibodies against AAV2 (FIG. 63a). In accordance with our hypothesis, increasing the amount of linker per virus results in reduced recognition of the virus by IgG antibodies as shown by an almost 80% reduction in OD signal comparing the highest amount of linker (173.3 nmol) to the lowest amount (0.52 nmol). However, at these increased linker amounts, the transduction efficiency of the virus is strongly reduced. These data indicate that, at linker to virus ratios used to produce constructs that have been shown to provide enhanced transduction efficiency as established Examples 8 and 9 herein, virus recognition by antibodies is affected with an inverse correlation between spacer length and binding.

We also performed a neutralization assay in HEK293T cells to further elucidate if the reduced IgG binding to AAV2 with DBCO-PEG12 linkers observed at increased linker amounts correlated with a loss of neutralizing activity (FIG. 63b). As shown in FIG. 63b, the neutralizing capacity of the antibodies was not affected by constructs prepared at linker amounts of 0.52 nmol, 1.73 nmol, 5.2 nmol, 17.3 nmol, 52 nmol or 173.3 nmol per 3E+9 VG of the virus (notably, amounts that are still compatible with enhanced transduction). Therefore, despite a reduction in antibody binding, virus functionalization with amounts of linkers compatible with enhancing transduction is not likely to result in escape from neutralization.

Further we investigated whether increasing the PEG spacer length on either the linker portion that is attached to the virus only, or both on the virus and ligand affects recognition by antibodies. We modified the virus with DBCO-PEG4-NHS ("4-Virus"), DBCO-PEG2000-NHS ("2K-Virus") as well as modified virus that was first surface functionalized with the DBCO-PEG4-NHS linker and then crosslinked with WGA-PEG5000-Azide ("4-Virus 5K ligand"), and modified virus that was first surface functionalized with the DBCO-PEG2000-NHS linker and then crosslinked with WGA-PEG4-Azide ("2K-Virus 4 Ligand") (FIG. 64a). By increasing the PEG spacer length, we observed no difference in the recognition of AAV by antibodies by ELISA (FIG. 64a). Accordingly, there was no difference in the neutralization capacity upon increasing the PEG length of the DBCO-PEGn-NHS linker, neither in changing the PEG length of the WGA-PEG-Azide (FIGS. 64b-c64c).

Since we did not observe any changes in the neutralization assay by using the highly permissive HEK293T cell line we changed to the less permissive neuronal cell line PC12 cells (FIG. 65) and to primary DRGs (FIG. 66). In these experiments we surface modified the virus with DBCO-PEG4-NHS and then crosslinked with WGA-PEG4-Azide and incubated the surface modified virus with serial dilutions of mouse serum containing antibodies against AAV2. As shown in FIG. 65, in PC12 cells the transduction by the unmodified AAV is blocked at all serum dilutions tested, while the WGA-modified virus escapes the recognition by neutralizing antibodies starting at dilution 1:16, suggesting, without being bound by theory, the possibility that the WGA surface modified virus might use a different route to enter PC12 cells, thereby circumventing inhibition by antibodies. We also applied this neutralization assay to DRG cultures and also here we showed the escape of the WGA surface modified virus at serum dilutions that completely neutralized the unmodified. AAV2 (FIG. 66).

SEQ ID NO: 1

ATAGGTGTAACTACGTCACT amino acid sequence of nemolizumab

SEQ ID NO: 2

ATGGTTTCTGCTATCGTGCTGTACGTGCTGCTGGCTGCTGCAGCTCAC

TCCGCTTTCGCTCAAGTGCAGCTGGTGCAGTCCGGTGCTGAAGTGAAG

AAACCCGGTGCTTCCGTGAAGGTGTCCTGCAAGGCTTCCGGTTACACT

TTCACCGGCTACATCATGAACTGGGTCCGACAGGCTCCTGGACAGGGA

CTCGAATGGATGGGCCTGATCAACCCCTACAACGGTGGCACCGACTAC

AACCCTCAGTTCCAGGACCGTGTGACCATCACCGCTGACAAGTCCACC

TCCACCGCTTACATGGAACTGTCCAGCCTGCGTTCCGAGGACACCGCT

GTTTACTACTGCGCTCGTGACGGTTACGACGACGGTCCCTACACTCTG

GAAACCTGGGGACAGGGTACTCTGGTCACCGTGTCATCTGGTGGTGGC

GGTTCTGGCGGTGGTGGTAGCGGAGGTGGTGGTTCTGACATCCAGATG

ACCCAGTCTCCATCCTCTCTGTCCGCTTCAGTGGGCGACCGTGTCACT

ATCACTTGCCAGGCTTCCGAGGATATCTACTCCTTCGTGGCTTGGTAT

CAGCAGAAGCCCGGCAAGGCTCCCAAGCTGCTGATCTACAACGCTCAG

ACTGAGGCTCAGGGTGTCCCCTCTCGTTTCTCCGGTTCCGGTTCTGGA

ACCGACTTTACCCTGACCATCAGCTCCCTGCAGCCTGAGGACTTCGCT

ACCTACTACTGCCAGCACCACTACGACTCCCCACTGACTTTCGGTGGT

GGCACCAAGGTCGAGATCAAGTCCTCCTCCTCCGGATCTTCCTCCTCT

GGTTCTGCTGCTCTGCCCGAGACTGGTGGTACCCATCACCATCATCAT

CACTAA synthesized amino acid Sequence of
Nemolizumab SNAP
SEQ ID NO: 3
MVSAIVLYVLLAAAAHSAFAQVQLVQSGAEVKKPGASVKVSCKASGYTFT

GYIMNWVRQAPGQGLEWMGLINPYNGGTDYNPQFQDRVTITADKSTSTAY

MELSSLRSEDTAVYYCARDGYDDGPYTLETWGQGTLVTVSSGGGGSGGGG

SGGGGSDIQMTQSPSSLSASVGDRVTITCQASEDIYSFVAWYQQKPGKAP

KLLIYNAQTEAQGVPSRFSGSGSGTDFTLTISSLQPEDFATYYCQHHYDS

PLTFGGGTKVEIKSSSSGSSSSGSAALPETGGTMDKDCEMKRTTLDSPLG

KLELSGCEQGLHEIKLLGKGTSAADAVEVPAPAAVLGGPEPLMQATAWLN

AYFHQPEAIEEFPVPALHHPVFQQESFTRQVLWKLLKVVKFGEVISYQQL

AALAGNPAATAAVKTALSGNPVPILIPCHRVVSSSGAVGGYEGGLAVKEW

LLAHEGHRLGKPGLCTHHHHHH

9. EQUIVALENTS AND INCORPORATION BY REFERENCE

While the invention has been particularly shown and described with reference to a preferred embodiment and various alternate embodiments, it will be understood by persons skilled in the relevant art that various changes in form and details can be made therein without departing from the spirit and scope of the invention.

All literature references, issued patents and patent applications cited within the body of the instant specification are hereby incorporated by reference in their entirety for all purposes.

PCT/EP2020/062713 is incorporated herein by reference in its entirety for all purposes.

---

SEQUENCE LISTING

```
Sequence total quantity: 4
SEQ ID NO: 1            moltype = DNA  length = 20
FEATURE                 Location/Qualifiers
misc_feature            1..20
                        note = Description of Artificial Sequence: Synthetic
                        oligonucleotide
source                  1..20
                        mol_type = other DNA
                        organism = synthetic construct
SEQUENCE: 1
ataggtgtaa ctacgtcact                                                20

SEQ ID NO: 2            moltype = DNA  length = 870
FEATURE                 Location/Qualifiers
misc_feature            1..870
                        note = Description of Artificial Sequence: Synthetic
                        polynucleotide
source                  1..870
                        mol_type = other DNA
                        organism = synthetic construct
SEQUENCE: 2
atggtttctg ctatcgtgct gtacgtgctg ctggctgctg cagctcactc cgctttcgct   60
caagtgcagc tggtgcagtc cggtgctgaa gtgaagaaac ccggtgcttc cgtgaaggtg  120
tcctgcaagg cttccggtta cactttcacc ggctacatca tgaactgggt ccgacaggct  180
cctggacagg gactcgaatg gatgggcctg atcaacccct acaacggtgg caccgactac  240
aaccctcagt tccaggaccg tgtgaccatc accgctgaca gtccacctc caccgcttac  300
atggaactgt ccagcctgcg ttccgaggac accgctgttt actactgcgc tcgtgacggt  360
tacgacgacg gtccctacac tctggaaacc tggggacagg gtactctggt caccgtgtca  420
tctggtggtg gcggttctgg cggtggtggt agcggaggtg gtggttctga catccagatg  480
acccagtctc catcctctct gtccgcttca gtgggcgacc gtgtcactat cacttgccag  540
gcttccgagg atatctactc cttcgtggct tggtatcagc agaagcccgg caaggctccc  600
aagctgctga tctacaacgc tcagactgag gctcagggtg tcccctctcg tttctccggt  660
tccggttctg gaaccgactt taccctgacc atcagctccc tgcagcctga ggacttcgct  720
acctactact gccagcacca ctacgactcc ccactgactt tcggtggtgg caccaaggtc  780
gagatcaagt cctcctcctc cggatcttcc tcctctggtt ctgctgctct gcccgagact  840
ggtggtaccc atcaccatca tcatcactaa                                   870

SEQ ID NO: 3            moltype = AA  length = 472
FEATURE                 Location/Qualifiers
REGION                  1..472
                        note = Description of Artificial Sequence: Synthetic
                        polypeptide
```

-continued

```
source          1..472
                mol_type = protein
                organism = synthetic construct
SEQUENCE: 3
MVSAIVLYVL LAAAAHSAFA QVQLVQSGAE VKKPGASVKV SCKASGYTFT GYIMNWVRQA    60
PGQGLEWMGL INPYNGGTDY NPQFQDRVTI TADKSTSTAY MELSSLRSED TAVYYCARDG   120
YDDGPYTLET WGQGTLVTVS SGGGGSGGGG SGGGGSDIQM TQSPSSLSAS VGDRVTITCQ   180
ASEDIYSFVA WYQQKPGKAP KLLIYNAQTE AQGVPSRFSG SGSGTDFTLT ISSLQPEDFA   240
TYYCQHHYDS PLTFGGGTKV EIKSSSSGSS SSGSAALPET GGTMDKDCEM KRTTLDSPLG   300
KLELSGCEQG LHEIKLLGKG TSAADAVEVP APAAVLGGPE PLMQATAWLN AYFHQPEAIE   360
EFPVPALHHP VFQQESFTRQ VLWKLLKVVK FGEVISYQQL AALAGNPAAT AAVKTALSGN   420
PVPILIPCHR VVSSSGAVGG YEGGLAVKEW LLAHEGHRLG KPGLCTHHHH HH           472

SEQ ID NO: 4            moltype = AA  length = 6
FEATURE                 Location/Qualifiers
REGION                  1..6
                        note = Description of Artificial Sequence: Synthetic 6xHis
                        tag
source                  1..6
                        mol_type = protein
                        organism = synthetic construct
SEQUENCE: 4
HHHHHH                                                                6
```

What is claimed is:

1. A surface modified viral capsid, comprising one or more of:
   a ligand covalently conjugated to a viral capsid protein via
      a linker, the linker comprising:
         a crosslinked moiety, wherein the crosslinked moiety is formed by a reaction between first and second members of a crosslinker reactive pair; and
         optionally one or more spacers;
      wherein the linker is covalently attached to a primary amino group of the capsid protein primary sequence.

2. The surface modified viral capsid according to claim 1, wherein the first and second members of the crosslinker reactive pair participate in a reaction selected from: a Cu(I)-catalyzed azide-alkyne cycloaddition (CuAAC) reaction, a strain-promoted alkyne-azide cycloaddition (SPAAC) reaction, a strain-promoted alkyne-nitrone cycloaddition (SPANC) reaction, an inverse electron demand Diels-Alder (IEEDD) reaction, and a Staudinger ligation and a [4+1] cycloaddition reaction.

3. The surface modified viral capsid according to claim 1, wherein the crosslinked moiety comprises at least one of: an eight membered ring and a triazole ring.

4. The surface modified viral capsid according to claim 2, wherein the reaction is a strain-promoted alkyne-azide cycloaddition (SPAAC) reaction.

5. The surface modified viral capsid according to claim 1, wherein the crosslinker reactive pair comprises a cyclooctyne and an azide.

6. The surface modified viral capsid according to claim 5, wherein the cyclooctyne is selected from dibenzylcyclooctyne (DIBO), dibenzoazacyclooctyne (DBCO), and biarylazacyclooctynone (BARAC), or a derivative thereof.

7. The surface modified viral capsid according to claim 6, wherein the cyclooctyne is a DBCO.

8. The surface modified viral capsid according to claim 1, wherein the linker comprises one or more spacers.

9. The surface modified viral capsid according to claim 8, wherein the one or more spacers comprise from 1 to 20 monomers of polyethylene glycol.

10. The surface modified viral capsid according to claim 9, wherein the one or more spacers comprise from 2 to 8 monomers of polyethylene glycol.

11. The surface modified viral capsid according to claim 10, wherein at one of the one or more spacers comprise 4 monomers of polyethylene glycol.

12. The surface modified viral capsid according to claim 1, wherein the ligand is a cell-type specific ligand.

13. The surface modified viral capsid according to claim 1, wherein the ligand is selected from cytokines, growth factors, lectins, toxins, single chain antibodies, multiple chain antibodies or antigen binding antibody fragments, peptides and combinations thereof.

14. The surface modified viral capsid according to claim 1, wherein the primary amino group is selected from an N-terminal amino group, a lysine epsilon amino group and an arginine amino acid group.

15. The surface modified viral capsid according to claim 14, wherein the primary amino group is the epsilon amino group of a lysine amino acid residue.

16. The surface modified viral capsid according to claim 1, wherein the linker is covalently attached to the ligand via a primary amino group of the ligand.

17. The surface modified viral capsid according to claim 1, wherein the protein sequence of the viral capsid has been mutated to attenuate or abrogate binding of the capsid to mammalian cell polysaccharides or proteoglycans.

18. The surface modified viral capsid according to claim 1, wherein the viral capsid is selected from an adenovirus capsid, adeno-associated virus capsid, retro virus capsid, lentivirus capsid, herpes simplex virus capsid, and a baculovirus capsid.

19. The surface modified viral capsid according to claim 18, wherein the viral capsid is an adeno-associated virus (AAV) capsid.

20. The surface modified viral capsid according to claim 19, wherein the viral capsid is an adeno-associated virus (AAV) capsid wherein at least one of the arginine residues at 585 and 588 of VP1, or analogous positions in VP2 or VP3, have been mutated.

21. The surface modified viral capsid according to claim 20, wherein the arginine residues at 585 and 588 of VP1, have been mutated to alanine residues.

22. A surface modified viral capsid according to Formula I:

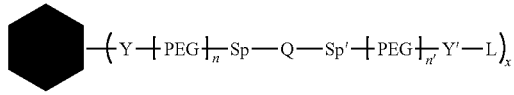

wherein:

is a viral capsid;
Y and Y' are independently an attachment moiety;
n and n' are independently 0 or an integer from 1 to 50;
Sp and Sp' are independently an optional spacer;
L is a ligand; and
x is a ligand per capsid ratio that is in a range from 1 to 500; and Q is selected from:

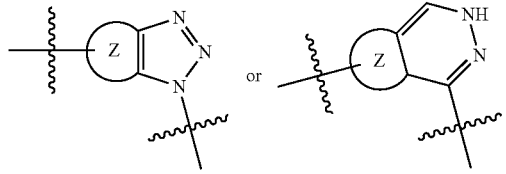

wherein, Z is a 7 or 8 membered cyclic or heterocyclic structure.

23. The surface modified viral capsid according to claim 22, wherein x ranges from 100-200.

24. The surface modified viral capsid according to claim 22, wherein x ranges from 130-170.

* * * * *